United States Patent
Trudeau et al.

(10) Patent No.: US 8,409,213 B2
(45) Date of Patent: Apr. 2, 2013

(54) INSERTION INSTRUMENT FOR ARTIFICIAL DISCS

(75) Inventors: Jeffrey L. Trudeau, Marquette, MI (US); Jason Thomas Berry, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 378 days.

(21) Appl. No.: 12/727,211

(22) Filed: Mar. 18, 2010

(65) Prior Publication Data

US 2010/0249797 A1    Sep. 30, 2010

Related U.S. Application Data

(63) Continuation-in-part of application No. 11/836,234, filed on Aug. 9, 2007, now Pat. No. 7,976, 550.

(60) Provisional application No. 61/161,277, filed on Mar. 18, 2009, provisional application No. 60/822,027, filed on Aug. 10, 2006, provisional application No. 60/846,859, filed on Sep. 22, 2006, provisional application No. 60/909,285, filed on Mar. 30, 2007.

(51) Int. Cl.
*A61B 17/58* (2006.01)
*A61B 17/60* (2006.01)
*A61F 2/00* (2006.01)

(52) U.S. Cl. ........................................ 606/99
(58) Field of Classification Search .................... 606/99; 604/528

See application file for complete search history.

(56) References Cited

U.S. PATENT DOCUMENTS

| | | |
|---|---|---|
| 4,374,523 A | 2/1983 | Yoon |
| 4,566,466 A | 1/1986 | Ripple et al. |
| 4,899,761 A | 2/1990 | Brown et al. |
| 5,084,057 A | 1/1992 | Green et al. |
| 5,542,949 A | 8/1996 | Yoon |

(Continued)

FOREIGN PATENT DOCUMENTS

WO    9100713    1/1991

OTHER PUBLICATIONS

Bao, Q. et al., Artificial Disc Technology, Neurosurg. Focus, vol. 9, Oct. 2000, 7 pp.

(Continued)

*Primary Examiner* — Kevin T Truong
*Assistant Examiner* — David Bates
(74) *Attorney, Agent, or Firm* — Fitch, Even, Tabin & Flannery LLP

(57) ABSTRACT

An insertion instrument for inserting an implant in an intervertebral space is provided. The instrument includes an elongate shaft having proximate and distal ends with a longitudinal axis therebetween. On the distal end of the elongate shaft is a gripping device capable of shifting from a holding configuration for securing a portion of the implant relative the distal end and a releasing configuration to permit removal of the implant portion from the elongate shaft. The instrument also includes an actuating mechanism coupled between the gripping device and the handle that is operable to configure the gripping device in the holding configuration upon an initial actuation thereof and the releasing configuration upon a subsequent actuation thereof. An actuator may be resiliently coupled to the gripping device or other moveable components in order to limit the force applied by the actuator to a preset amount.

13 Claims, 53 Drawing Sheets

U.S. PATENT DOCUMENTS

| | | | |
|---|---|---|---|
| 5,562,736 | A | 10/1996 | Ray et al. |
| 6,478,801 | B1 | 11/2002 | Ralph et al. |
| 6,533,799 | B1 | 3/2003 | Bouchier |
| 6,607,559 | B2 | 8/2003 | Ralph et al. |
| 6,652,533 | B2 | 11/2003 | O'Neil |
| 6,669,730 | B2 | 12/2003 | Ralph et al. |
| 6,673,113 | B2 | 1/2004 | Ralph et al. |
| 6,824,565 | B2 | 11/2004 | Muhanna et al. |
| 6,863,689 | B2 | 3/2005 | Ralph et al. |
| 6,984,246 | B2 | 1/2006 | Huang |
| 2002/0065560 | A1 | 5/2002 | Varga et al. |
| 2002/0111683 | A1 | 8/2002 | Ralph et al. |
| 2002/0111687 | A1 | 8/2002 | Ralph et al. |
| 2002/0151979 | A1 | 10/2002 | Lambrecht et al. |
| 2003/0009227 | A1 | 1/2003 | Lambrecht et al. |
| 2003/0014113 | A1 | 1/2003 | Ralph et al. |
| 2003/0014115 | A1 | 1/2003 | Ralph et al. |
| 2003/0040802 | A1 | 2/2003 | Errico et al. |
| 2003/0069586 | A1 | 4/2003 | Errico et al. |
| 2003/0069642 | A1 | 4/2003 | Ralph et al. |
| 2003/0069643 | A1 | 4/2003 | Ralph et al. |
| 2003/0078590 | A1 | 4/2003 | Errico et al. |
| 2003/0078662 | A1 | 4/2003 | Ralph et al. |
| 2003/0093155 | A1 | 5/2003 | Lambrecht et al. |
| 2003/0130667 | A1 | 7/2003 | Lin |
| 2003/0149438 | A1 | 8/2003 | Nichols et al. |
| 2003/0204362 | A1 | 10/2003 | Beresford et al. |
| 2003/0208203 | A1 | 11/2003 | Lim et al. |
| 2003/0216810 | A1 | 11/2003 | Ralph et al. |
| 2003/0229358 | A1 | 12/2003 | Errico et al. |
| 2004/0010316 | A1 | 1/2004 | William et al. |
| 2004/0024462 | A1 | 2/2004 | Ferree et al. |
| 2004/0030390 | A1 | 2/2004 | Ferree |
| 2004/0030391 | A1 | 2/2004 | Ferree |
| 2004/0034426 | A1 | 2/2004 | Errico et al. |
| 2004/0049280 | A1 | 3/2004 | Cauthen |
| 2004/0068321 | A1 | 4/2004 | Ferree |
| 2004/0093088 | A1 | 5/2004 | Ralph et al. |
| 2004/0098129 | A1 | 5/2004 | Lin |
| 2004/0133132 | A1 | 7/2004 | Chappuis |
| 2004/0133278 | A1 | 7/2004 | Marino et al. |
| 2004/0133280 | A1 | 7/2004 | Trieu |
| 2004/0143331 | A1 | 7/2004 | Errico et al. |
| 2004/0143332 | A1 | 7/2004 | Krueger et al. |
| 2004/0148028 | A1 | 7/2004 | Ferree et al. |
| 2004/0153065 | A1* | 8/2004 | Lim .................................. 606/53 |
| 2004/0153158 | A1 | 8/2004 | Errico et al. |
| 2004/0153159 | A1 | 8/2004 | Cauthen |
| 2004/0167534 | A1 | 8/2004 | Errico et al. |
| 2004/0167626 | A1 | 8/2004 | Geremakis et al. |
| 2004/0167628 | A1 | 8/2004 | Foley |
| 2004/0176843 | A1 | 9/2004 | Zubok et al. |
| 2004/0176845 | A1 | 9/2004 | Zubok et al. |
| 2004/0176848 | A1 | 9/2004 | Zubok et al. |
| 2004/0186577 | A1 | 9/2004 | Ferree |
| 2004/0225295 | A1 | 11/2004 | Zubok et al. |
| 2005/0027360 | A1 | 2/2005 | Webb et al. |
| 2005/0033305 | A1 | 2/2005 | Schultz |
| 2005/0033437 | A1 | 2/2005 | Bao et al. |
| 2005/0033438 | A1 | 2/2005 | Schultz et al. |
| 2005/0038445 | A1 | 2/2005 | Errico et al. |
| 2005/0038515 | A1 | 2/2005 | Kunzler |
| 2005/0038516 | A1 | 2/2005 | Spoonamore |
| 2005/0055097 | A1 | 3/2005 | Grunberg et al. |
| 2005/0060035 | A1 | 3/2005 | Errico et al. |
| 2005/0071012 | A1 | 3/2005 | Serhan et al. |
| 2005/0085917 | A1 | 4/2005 | Marnay et al. |
| 2005/0096745 | A1 | 5/2005 | Andre et al. |
| 2005/0113842 | A1 | 5/2005 | Bertagnoli et al. |
| 2005/0119752 | A1 | 6/2005 | Williams et al. |
| 2005/0131541 | A1 | 6/2005 | Trieu |
| 2005/0143820 | A1 | 6/2005 | Zucherman et al. |
| 2005/0143824 | A1 | 6/2005 | Richelsoph et al. |
| 2005/0154463 | A1 | 7/2005 | Trieu |
| 2005/0154464 | A1 | 7/2005 | Humphreys et al. |
| 2005/0154466 | A1 | 7/2005 | Humphreys et al. |
| 2005/0154468 | A1 | 7/2005 | Rivin |
| 2005/0192670 | A1 | 9/2005 | Zubok et al. |
| 2005/0192671 | A1 | 9/2005 | Bao et al. |
| 2005/0203538 | A1 | 9/2005 | Lo et al. |
| 2006/0069436 | A1 | 3/2006 | Sutton et al. |
| 2006/0241761 | A1 | 10/2006 | Gately |
| 2007/0213461 | A1 | 9/2007 | Hu et al. |
| 2007/0233153 | A1* | 10/2007 | Shipp et al. ..................... 606/99 |
| 2008/0091211 | A1 | 4/2008 | Gately |

OTHER PUBLICATIONS

International Searching Authority, International Search Report, corresponding to International Patent Appln. No. PCT/US2007/07517, Apr. 23, 2008, 1 pg.

International Searching Authority, International Search Report, corresponding to International Patent Appln. No. PCT/2007/075693, Jul. 3, 2008, 1 pg.

* cited by examiner

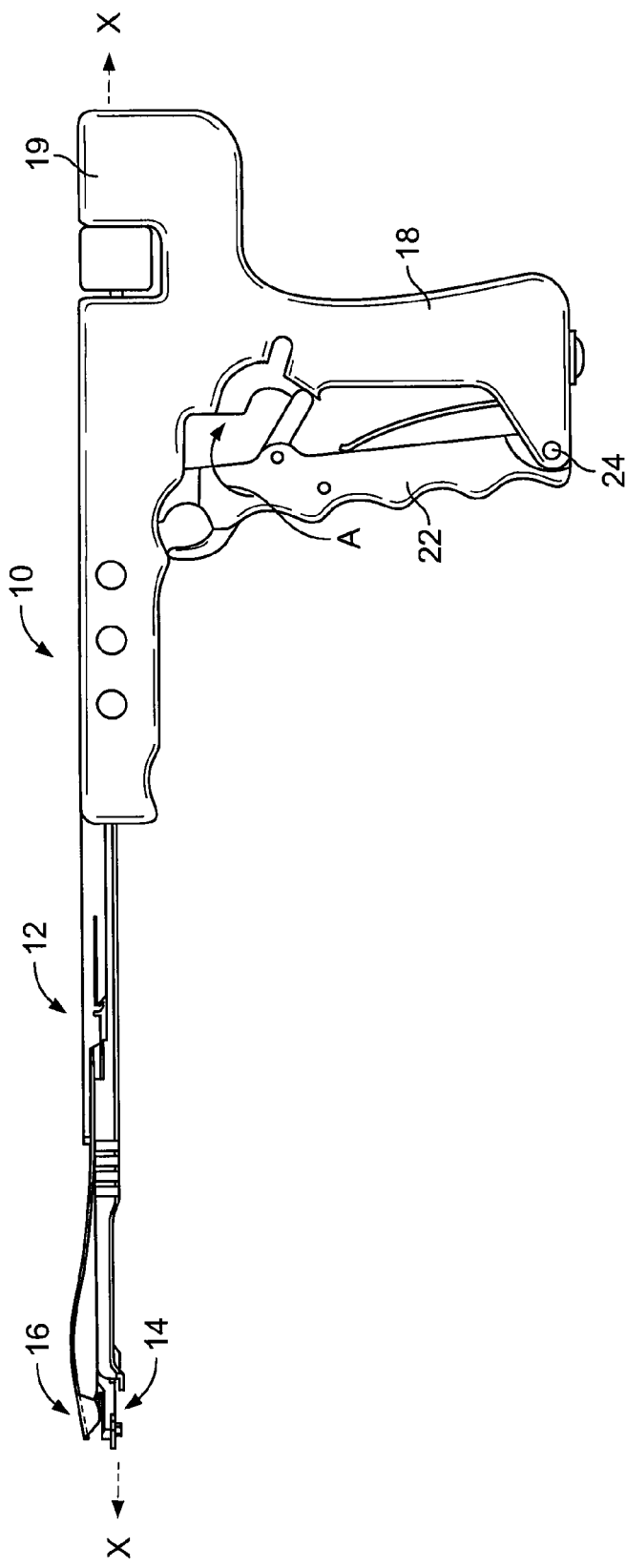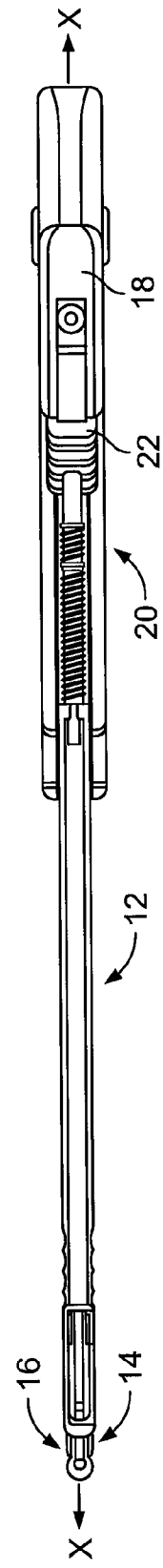
FIG. 4
FIG. 5

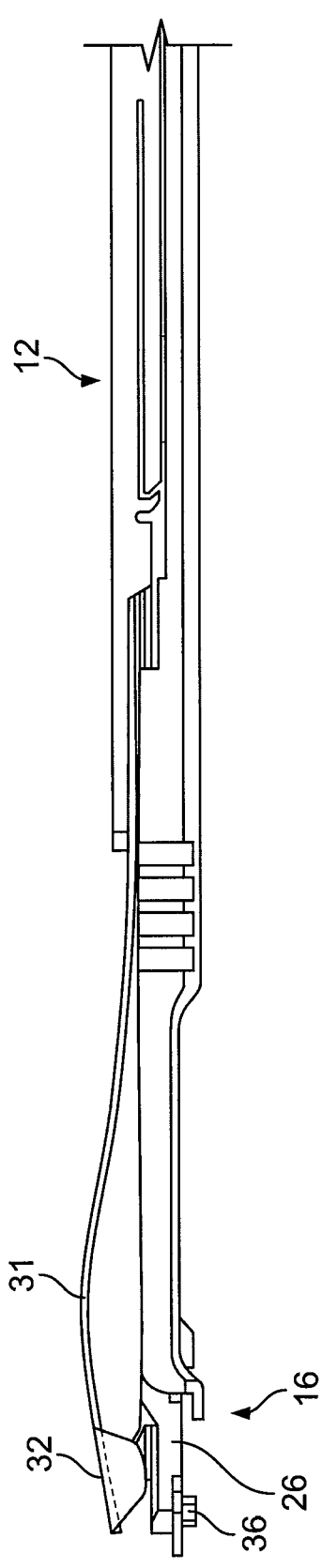
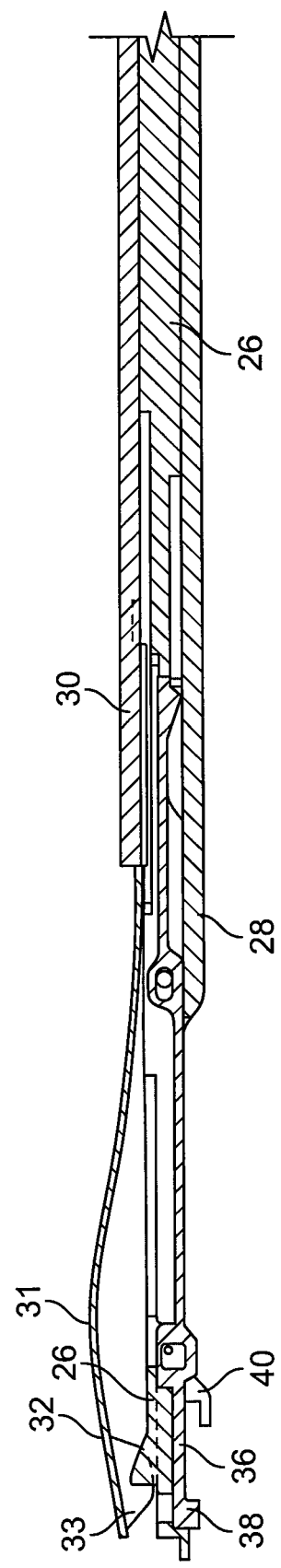
FIG. 7
FIG. 8

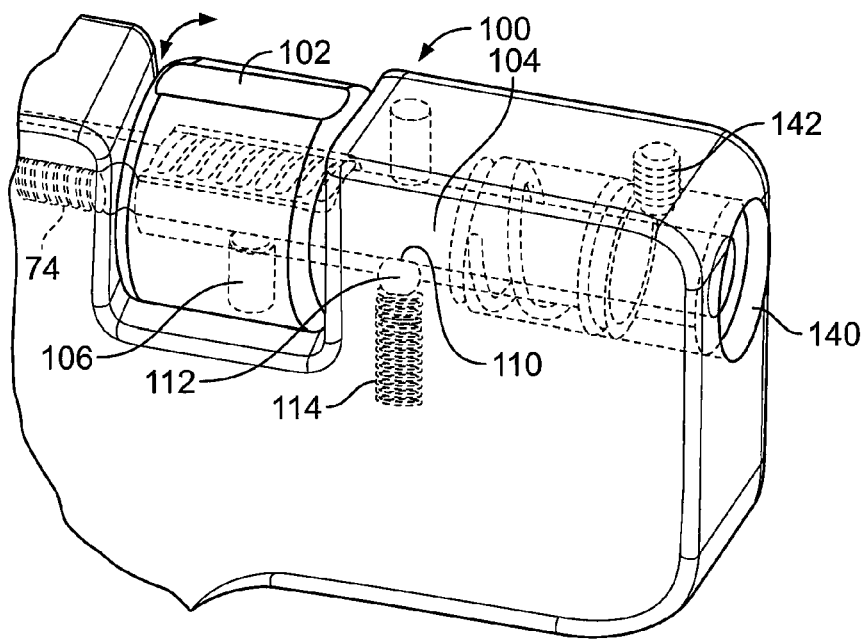
FIG. 27
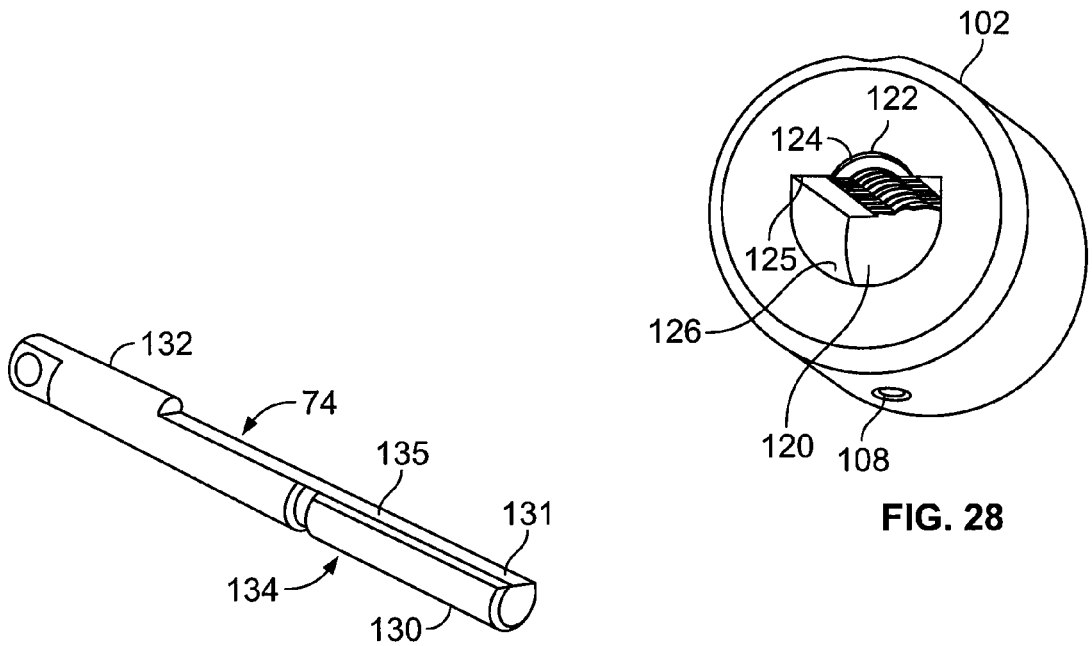
FIG. 29
FIG. 28

INSERTION INSTRUMENT FOR ARTIFICIAL DISCS

CROSS-REFERENCE TO RELATED APPLICATIONS

This application claims the benefit of U.S. Provisional Application No. 61/161,277, filed Mar. 18, 2009, and is a continuation-in-part of U.S. patent application Ser. No. 11/836,234, filed Aug. 9, 2007, which claims benefit of U.S. Provisional Application No. 60/822,027, filed Aug. 10, 2006, U.S. Provisional Application No. 60/846,859, filed Sep. 22, 2006 and U.S. Provisional Application No. 60/909,285, filed Mar. 30, 2007, all of which are hereby incorporated by reference as if reproduced herein in their entirety.

FIELD

This invention relates to insertion instruments for artificial disc devices and other implants used in the vertebrae, and in particular, insertion instruments used to hold multiple piece implants for insertion into the vertebrae.

BACKGROUND

The most common orthopedic condition for which professional medical treatment is sought is lower back pain. Although many factors may be responsible for causing lower back pain, a principal factor is damage or degeneration of an intervertebral spinal disc resulting in impingement on the nerve system, specifically the spinal cord, located within the spine. Such impingement may result in, for instance, loss of mobility, urinary and fecal incontinence, and sciatica or pain experienced in the extremities.

Damage to or degeneration of a spinal disc can result from a number of factors such as abuse or age. The disc itself is composed primarily of an annulus and a nucleus contained therein. The annulus is a fibrous annular piece that attaches to the adjacent vertebrae and contains the nucleus, which is in turn a gel like viscous material capable of shock absorption and flowable to permit poly axial rotation and resilient compression of the vertebrae and spine. Most frequently, disc degeneration results from damage occurring to the annulus such that the flowable nucleus material may leak or seep out of the annulus. Disc degeneration also can occur in other ways, such as by being deprived of nutrient flow leading to a dried disc susceptible to damage. Because the nuclear material is flowable, extensive damage to the annulus is not necessary for leakage to occur.

Currently, approaches to treatment of spinal problems directly affecting the spinal cord are numerous. For instance, immobilization and high doses of corticosteroids may be employed. The dominant surgical procedures for treatment of these problems are spinal fusion and discectomy. Fusion is a method where adjacent vertebrae are immobilized so that they permanently secure to each other by having bone growth between and to the vertebrae, while discectomy involves removal of a portion or an entirety of a spinal disc.

However, the current practice of each of these procedures typically has certain limitations. With fusion, making a portion of the spine generally rigid produces a reduction in mobility, and drastically alters normal load distribution along the spinal column. Due to these factors, the non fused portions of the spine experience stress and strain that are significantly increased over normal physiological motions. The increased stress and strain on the non fused portions may lead to accelerated disc degeneration of the non fused portions, particularly the adjacent levels of the spine.

Discectomy is effective for relieving sciatic pain by removing the damaged or herniated disc tissue compressing the spinal nerves. However, current discectomy often may lead to a reduction of the disc space between adjacent vertebrae, as well as instability in the affected portion of the spine. Such long term effects with current discectomy often result in further surgery several years after the initial discectomy surgery.

A recent, though not new, development for spinal surgery of this type is a procedure known as disc arthroplasty for restoring or reconstructing the disc using a prosthesis to replace a portion or entirety of the damaged disc. The primary objective of disc arthroplasty is to restore or maintain the normal disc anatomy and functions, while addressing and treating the causes of the pain.

Two types of prostheses for disc arthroplasty are currently believed to merit further development by medical science and research. One type is a total disc prosthesis, or TDP, where the entire spinal disc is replaced after radical discectomy. A typical TDP includes structures that together attempt to mimic the properties of a natural disc.

The other type is a disc nucleus prosthesis, or DNP, that is used to replace only the nucleus of a spinal disc after a nucleotomy while retaining the annulus of the disc and, possibly, the end plates intact. As discussed above, failure of the natural disc does not require extensive damage to the annulus, and the annulus would often be capable of retaining a non flowing prosthetic nucleus. Implantation of a DNP involves clearing of the natural nucleus from the annulus through the procedure known as nucleotomy, and inserting the DNP within the annulus. Accordingly, DNPs are typically smaller and require less extensive surgery than TDPs while still mimicking some of the biomechanical properties of a natural intervertebral disc. Herein, the term artificial disc, device, or implant can refer to either a TDP or a DNP.

In using disc implants, one problem relates to the preparation for the surgical procedure for implanting either the TDPs or DNPs. The time required for preparing for surgery, and specifically preparing the implants and inserters for use, can be important for both patient welfare and in terms of cost efficiency. For instance, if only one of the ends of the implant is configured for gripping by an inserter tool, this requires the medical personnel to locate the proper end of the implant and then connect it to the inserter. Extra time is wasted when an implant has otherwise similarly configured ends such that it is difficult to easily determine which end of the implant attaches to the inserter. The problem is compounded when the implant has multiple components (such as a top and bottom portion), and the medical personnel need to first properly match the disc components to each other so that the ends of each component configured to connect to each other are properly aligned with each other before attachment of the disc to the inserter. This can waste time during preparation for the surgical procedure. Accordingly, an artificial disc would be desirable that has portions that do not only connect with each other in one configuration and require that the disc be mounted on an inserter tool in a single orientation.

Other improvements specifically for the DNP procedure would be desirable. As mentioned above, a DNP requires less extensive surgery than for a TDP since it replaces only part of the disc. Implantation of most known DNPs with pre formed dimensions generally requires a 5 to 6 mm, or larger, incision in the annulus for implantation. The incision, however, should be kept as small as possible to hold the DNP within the annulus without using anchors on the DNP that extend into the end plates of the vertebrae for securing the DNP. The minimal invasiveness of the procedure results in minimal recovery and post surgical pain, and interbody fusion remains a viable revision surgery. Thus, maintaining a small incision and keeping damage to the annulus to a minimum is a high priority. Therefore, it would be desirable to provide a DNP and inserter that does not require an enlarged incision and does not significantly damage the annulus or other tissue during insertion and placement of the DNP.

Another problem with DNP structure and the surgical procedures involving DNP relate to the positioning of the artificial disc within the nuclear space. For some DNPs, once the implant is positioned in the nuclear space, it must be rotated in order to position it properly for providing its full range of motion and its full shock absorption capabilities to the patient. Thus, a DNP and an inserter that manipulates the DNP within the nuclear space without causing damage to the annulus are also desired.

Current insertion instruments for artificial disc devices further complicate the surgical procedures due to the requirement that the surgeon manipulate multiple controls to grasp, hold, and release the implant as well as require the surgeon to hold such instruments using a generally un-natural wrist position. One such example is the insertion tool described in U.S. Pat. No. 6,478,801 to Ralph et al. The tool of the '801 patent is a generally elongate member having a handle on one end thereof aligned with a longitudinal axis of the handle. On a lower portion of the handle is a first control to mechanically hold the implant to a compression assembly on an opposite end of the elongate member. On an upper portion of the handle is a second, separate control to release the implant. In use, with the handle aligned along the longitudinal axis of the instrument, the surgeon is required to hold the instrument with some degree of wrist flexion, extension, ulnar deviation, or radial deviation in order to insert a connected implant into the vertebral space of a patient. Moreover, while grasping the instrument with such wrist positioning, the surgeon is also required to manipulate multiple controls to both hold and release the implant, which further complicates the operation of the instrument.

Other instruments, such as those described in US Patent Publication Nos. 2003/0149438A1 to Nichols et al. and 2005/0060035A1 to Errico et al. also employ instruments having handles aligned with the longitudinal axis of the tool shafts. These instruments, however, also have controls that require both hands of the surgeon to operate the instrument. That is, one hand of the surgeon holds the instrument while the other hand operates a control to grasp and release the implant on the opposite end of the shaft.

Accordingly, there is a desire for an insertion instrument to hold an artificial disc device for insertion into a vertebral disc space with simplified operations to grasp and release the implant, and instruments that permit comfortable wrist positioning for the surgeon during use.

SUMMARY

In one form, an insertion instrument is provided that is configured for controllably inserting an artificial disc device, such as a DNP or TNP spinal implant, a dynamic spacer device, a trial spacer device, or other implant device, between adjacent, superior and inferior vertebrae. The instrument includes an elongate shaft having proximate and distal ends with a longitudinal axis therebetween. Adjacent a distal end of the elongate shaft, the instrument includes a gripping device or mechanism having a holding configuration for securing a portion of the artificial disc device (e.g., an inferior member of the disc device) thereon for insertion into the vertebral space and also a releasing configuration that permits removal of the artificial disc device portion from the instrument. Preferably, the artificial disc device includes an inferior member and a superior member where the inferior member is the portion secured to the gripping mechanism. In one aspect, the instrument may include a handle portion spaced from the distal end that is configured to be comfortably held with a generally neutral wrist position. For purposes herein, a generally neutral wrist position means substantially free of wrist flexion, extension, ulnar deviation, or radial deviation. In one embodiment, the handle portion can be used with a generally neutral wrist position because it is in the form a pistol-grip handle, which is preferably adjacent the proximate end of the instrument.

With such a handle configuration, the instrument provides advantages over prior instruments that include a handle portion aligned along the longitudinal axis of the instrument, such as the prior instruments of Ralph et al., Nichols et al., and Errico et al. described in the background. In use, the prior instruments with handles extending along the longitudinal axis typically require some un-natural wrist positioning in order to secure the artificial disc device thereon or to insert the disc device in a patient during surgery. The instruments provided herein, on the other hand, can be comfortably used generally without un-natural wrist positioning. By using a generally neutral wrist position to hold and use the instrument, the disclosed instruments permit better control thereof when inserting a disc device into a vertebral space, which generally means less damage to surrounding tissue.

In another form, the instrument also includes an actuating mechanism that is coupled between the gripping mechanism and the handle. The actuating mechanism is operable to configure the gripping mechanism adjacent the distal end of the instrument in one of the holding configuration and the releasing configuration. Similar to the handle, the actuating mechanism is also configured to be operated comfortably using a generally neutral wrist position. To this end, the actuating mechanism preferably includes a trigger portion that is configured to move relative to the handle such as being comfortably squeezed by a surgeon to operate the actuating mechanism in order to shift the gripping device between the holding and releasing configuration.

Preferably, the actuating mechanism also includes a pivot connection between the handle and trigger so that the trigger may be actuated by squeezing or pivoting the trigger towards the handle. Such configuration is advantageous because the actuating mechanism, and in particular, the trigger thereof, can also be operated comfortably with the same neutral positioning of the wrist that enables the surgeon to hold the instrument.

In one particular form, the actuating mechanism is preferably capable of switching between the holding and releasing configuration of the gripping device using the same actuating motion of the trigger. In other words, only the single trigger portion is preferably needed to both hold and release the artificial disc device on the distal end of the instrument. Prior instruments, on the other hand, require multiple controls to both hold and release the instrument, which complicates the use of the instrument or necessitates both hands of the surgeon to secure and release the implant.

In another embodiment, the instrument also includes a locking device to substantially restrict movement of the artificial disc device about the distal end of the elongate shaft. In another form, an insertion instrument is provided that includes a handle, at least one elongate shaft member having a distal end for engaging a portion of the artificial disc device with the elongate shaft member configured to be shifted between a holding configuration for securing the artificial disc device portion relative the shaft distal end and a releasing configuration to permit movement of the artificial disc device portion with respect to the shaft distal end, an actuator operable to shift the shaft member between the holding configuration and the releasing configuration, and a resilient coupling between the actuator and the elongate shaft member configured to limit the force applied by the elongate shaft member to the artificial disc device. The resilient coupling may include, for instance, a spring or combination of springs that is preloaded with a predetermined amount of force in order to limit the amount of force applied to the implant upon manipulation of the actuator. The spring or other resilient coupling may be configured as desired in order to determine the maximum amount of force applied. In addition, a resilient coupling linked to the actuator automatically adjusts for part variations due to machining tolerances.

BRIEF DESCRIPTION OF THE DRAWINGS

FIG. 4 is an elevational view of the insertion instrument showing a pistol grip configuration of the handle portion including a trigger coupled thereto and the distal end of the elongate shaft assembly in an initial configuration prior to receiving a disc device;

FIG. 5 is a bottom plan view of the insertion instrument showing a spring mechanism coupled to the trigger;

FIG. 7 is an elevational view of the elongate shaft assembly showing the fixed portion, the lower slidable portion, and the upper pivotable portion having a biased holding member;

FIG. 8 is a cross-sectional view of the distal end of the insertion instrument showing the gripping mechanism thereon;

FIG. 27 is a perspective view of the locking device showing a coil spring member and a selective engagement between the lock knob and coupling member; the lock knob and coupling member are shown disengaged;

FIG. 28 is a perspective view of the lock knob showing a bore extending therethrough having internal threads defined on a portion of an inner surface thereof that has a generally D-shaped profile;

FIG. 29 is a perspective view of the coupling member showing external threading extending completely around the coupling member in one portion thereof and only extending partially around the coupling member in another portion thereof;

DETAILED DESCRIPTION OF THE PREFERRED EMBODIMENTS

Figure 1:
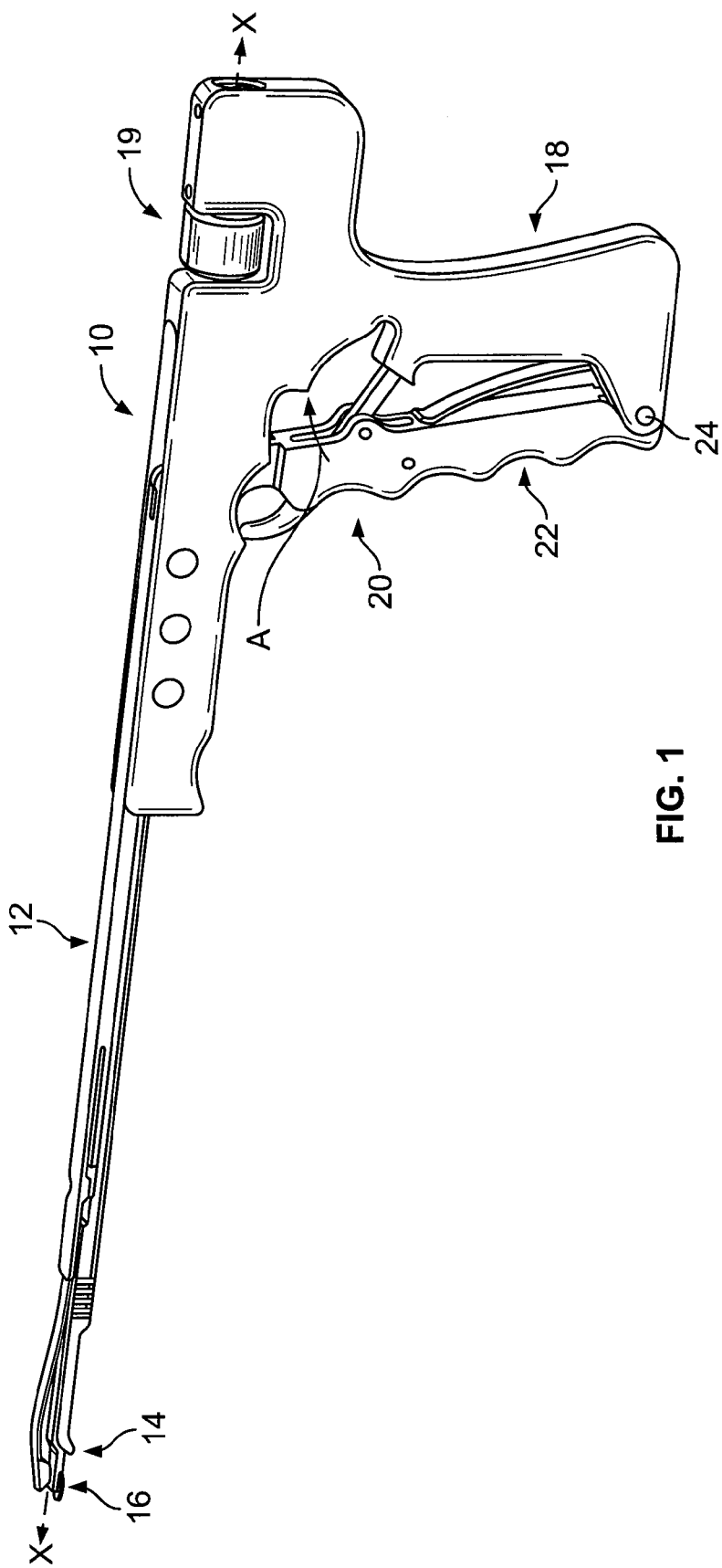
FIG. 1 is a perspective view of one embodiment of an insertion instrument for use with artificial disc devices (not shown) illustrating an elongate shaft assembly having a distal end portion including a gripping mechanism thereon and a handle portion spaced from the distal end that is oriented relative to the elongate shaft such that the handle portion may be held with substantially neutral wrist positioning.
Figure 2:
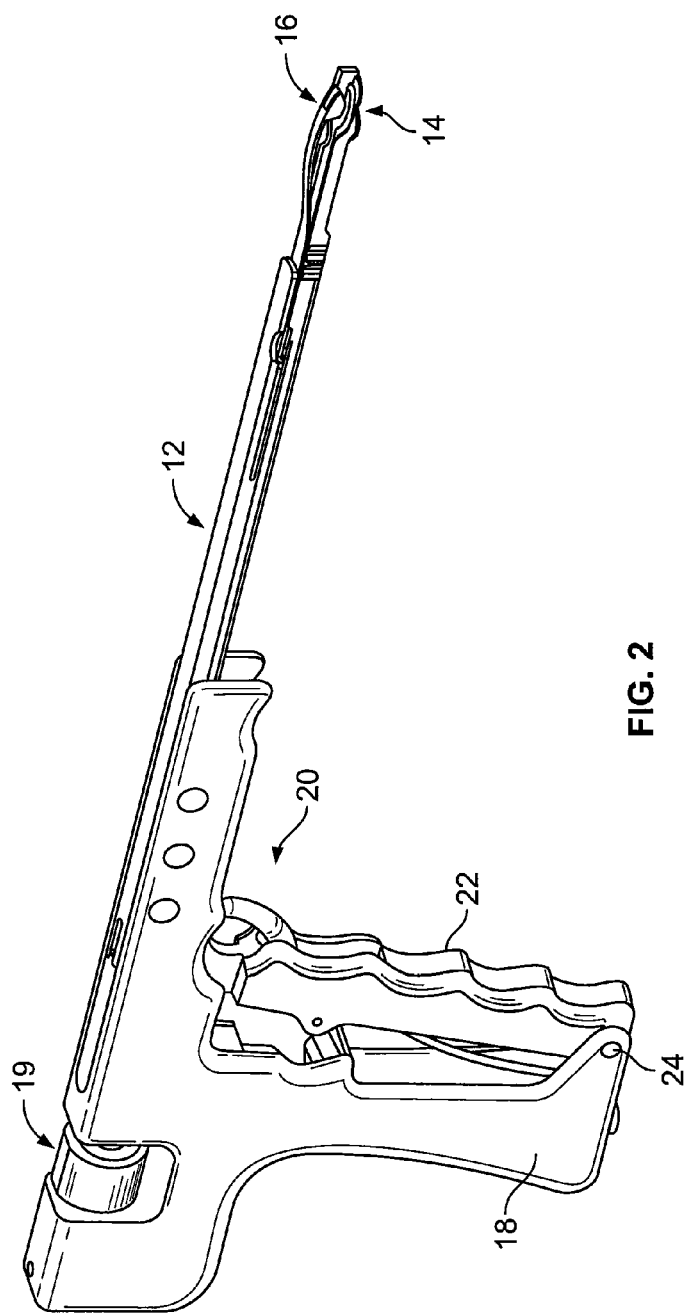
FIG. 2 is a perspective view of the insertion instrument showing the distal end portion thereof for holding the artificial disc device (not shown)
Figure 3:
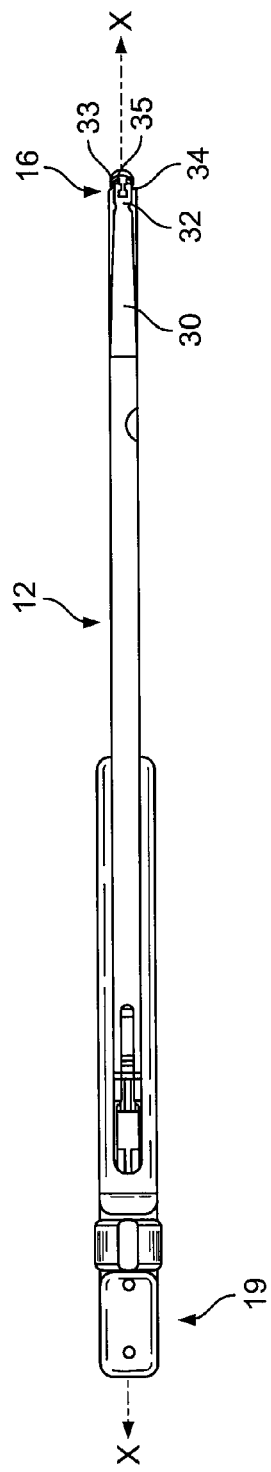
FIG. 3 is a top plan view of the insertion instrument showing the elongate shaft assembly.

Referring to the figures, an insertion instrument 10 for use with artificial disc devices and implants is illustrated. Preferably, the instrument 10 is configured for grasping, orienting, and controllably inserting a disc device between adjacent, superior and inferior vertebrae of a patient. As used herein, disc device refers to a DNP or TNP spinal implant, a dynamic spacer device, a trial spacer device, or other suitable implant device configured for insertion between adjacent vertebrae.

Referring initially to FIGS. 1 to 5, the instrument 10 generally includes an elongate shaft assembly 12 having a distal end portion 14 with a gripping mechanism 16 thereon capable of shifting between a holding configuration for securing the disc device thereon and a releasing configuration for removal of the disc device from the instrument. The instrument 10 also includes a handle portion 18, which is spaced from the gripping mechanism 16, oriented relative to a longitudinal axis X extending along the elongate shaft assembly 12 such that the handle portion 18 may be held with substantially neutral wrist positioning during use thereof.

For purposes herein, a generally neutral wrist position means a wrist substantially free of flexion, extension, ulnar deviation, or radial deviation. In one embodiment, the handle portion 18 can be comfortably used with a generally neutral wrist position because it is in the form of a pistol-grip adjacent a proximate end portion 19 of the elongate shaft 12. In this manner, the instrument 10 provides the surgeon or other user better control thereof when inserting an implant into a vertebral space, which generally means less damage to the surrounding tissue and less time in the operating room.

To operate the gripping mechanism 16, the instrument includes an actuator 20 that is coupled between the gripping mechanism 16 and the handle portion 18. The actuator 20 is operable for shifting the gripping mechanism 16 between the holding and releasing configuration. Preferably, the actuator 20 is capable of shifting the gripping mechanism 16 between the holding and releasing configurations via the same actuation motion of the actuator 20. Similar to the handle portion 18, the actuator 20 is also preferably configured to be comfortably operated using the same generally neutral wrist position.

By one approach, the actuator 20 includes a trigger 22 that is configured to move relative to the handle portion 18 such as being comfortably squeezed by a surgeon using a single hand. Upon one or more actuations of the trigger 22, it is operable to configure the distal end 14 of the elongate shaft assembly 12 or gripping mechanism 16 to grasp and/or release a disc device therefrom. In one form, the trigger 22 is mounted to the handle portion 18 through a pivot connection 24 so that it may be squeezed in the direction of Arrow A to operate the gripping mechanism 16 (FIG. 1). Such combination of the trigger 22 and handle portion 18 in the form of a pistol grip is advantageous because the actuator 20, and in particular the trigger portion 22 thereof, can be operated comfortably with the same neutral positioning of the wrist that enables a user to hold the instrument 10.

In one particular form, the actuator 20 is preferably capable of switching between the holding and releasing configuration of the gripping mechanism 16 using the same actuating motion of the trigger (i.e., squeezing along direction A generally along the longitudinal axis X). In other words, only the single trigger 22 is preferably needed to both hold and release the disc device to the instrument without the need for additional controls as typically found in prior instruments. That is, the instrument 10 can secure and release a disc device through the same actuating motion of the single trigger, such as squeezing, which permits instrument operation with only a single hand of the surgeon. As further described below, a first actuation (i.e., squeeze) of the trigger 22 configures the gripping mechanism 16 into the holding configuration and a second actuation (i.e., squeeze) of the trigger 22 configures the gripping mechanism 16 into the releasing configuration. To facilitate operation of the instrument, the actuator 20 also preferably includes a number of bias elements to shift the actuator between gripping and release an implant. Operation of these bias elements will also be further described below.

Figure 6:
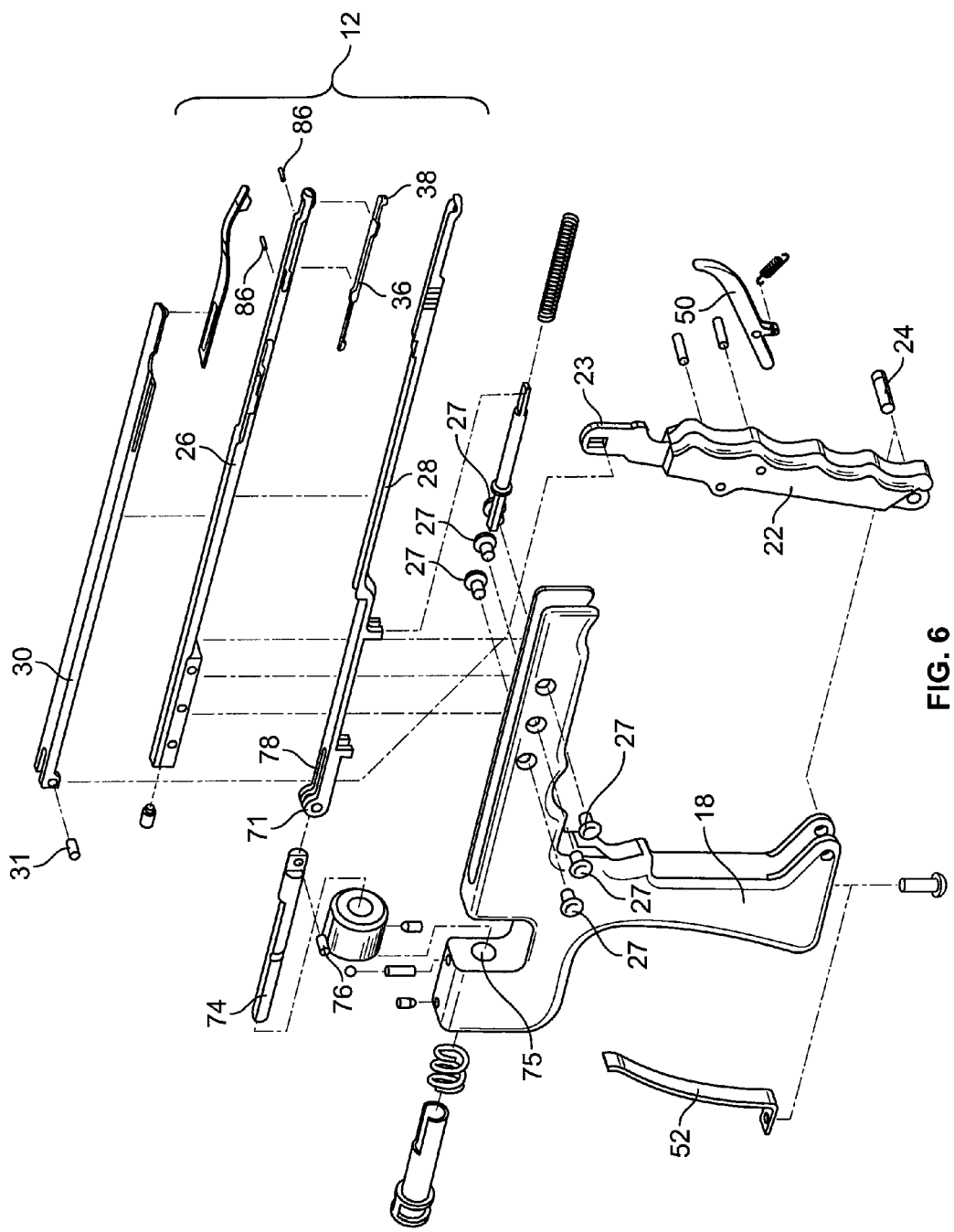
FIG. 6 is an exploded view of the insertion instrument showing an actuation mechanism that includes the trigger connected to the handle portion through a pivot connection and further showing the elongate shaft assembly having a central, fixed portion (fixed to handle portion), a lower slidable portion (slidable relative to the fixed portion), and an upper pivotable portion (pivotable relative to the fixed portion)

Turning to FIG. 6, the elongate shaft assembly 12 of the instrument 10 preferably includes a plurality of members that include both fixed and movable components. In one embodiment, the shaft assembly 12 includes a central, fixed member 26 that is secured to handle portion 18 via one or more fasteners 27. The shaft assembly 12 also includes a lower, slidable member 28 that is configured to shift along the longitudinal axis X relative to the fixed shaft 26 upon actuation of the trigger 22. The shaft assembly 12 also includes an upper, pivotable member 30 that is pivotable relative to the fixed shaft 26 via a pivot 31 mounted to the trigger 22. As illustrated, the upper shaft 30 is coupled to an upper end 23 of the trigger 22 and is also configured to translate along the longitudinal axis X with the pivoting of the trigger 22.

The distal end 14 of the elongate shaft assembly 12, which has the gripping mechanism 16 thereon, is illustrated in FIGS. 7 and 8 in more detail. As mentioned above, the gripping mechanism 16 shifts between a gripping configuration where it holds a disc device thereon and a release configuration where it releases a previously held disc device. In the gripping configuration, it holds a superior member of a disc device on the upper pivotable member 30 of the shaft assembly 12 and holds an inferior member of a disc device due to the cooperation of the slidable member 28 and the fixed member 26.

More specifically, the gripping mechanism 16 includes a first portion of a resilient strip member 31 forming a yoke grip that is biased to be bowed upwardly relative to the central fixed shaft 26 of the elongate shaft assembly 12. Preferably, the resilient member 31 is connected to a distal end of the upper pivotable shaft 30. As further described below, the bowed configuration of the resilient member 31 helps orient the superior member of a disc device to extend in a generally transverse or inclined direction relative to the instrument longitudinal axis X in a wedge configuration. In order to grasp the disc device superior member, the resilient member 31 has a grasping claw 32 for engaging a neck or post on the superior member of the disc device (i.e., FIG. 3). In one form, the claw 32 has two laterally, spaced fingers 33 and 34 that form a groove 35 therebetween to secure a disc device post in the groove 35 (i.e., FIGS. 3 and 22).

Figure 16:
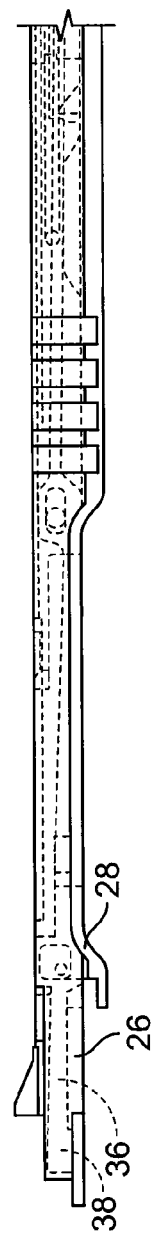
FIG. 16 is an elevational view of the distal end of the elongate shaft showing the gripping mechanism configured to receive an implant (not shown) with a latch member having a post thereon being retracted for receipt of the implant.

To hold an inferior member of a disc device, the elongate shaft assembly includes a latch member 36 having a depending post 38 on a distal end thereof. The latch member 36 is in the form of an elongate strip configured to shift between a latching position shown in FIGS. 7 and 8 and a retracted position shown in FIG. 16. In general, the gripping mechanism 16 holds the inferior implant member because the latch post 38 is sized to be received in an aperture defined in the inferior member of the implant. Thereafter, the lower slidable shaft 28 of the shaft assembly 12 then slides forward to abut an outer edge or at least a portion of an outer region of the inferior member of the disc device with a hooked end 40 (FIG. 8) capturing the implant between the post 38 and slidable shaft 28. Operation of the gripping mechanism 16 will be described in more detail below, but the gripping mechanism 16 and operation thereof is similar to that described in U.S. Patent Application Ser. No. 60/822,027, which this application claims priority to and is also incorporated by reference as if reproduced herein in its entirety.

Figure 9:
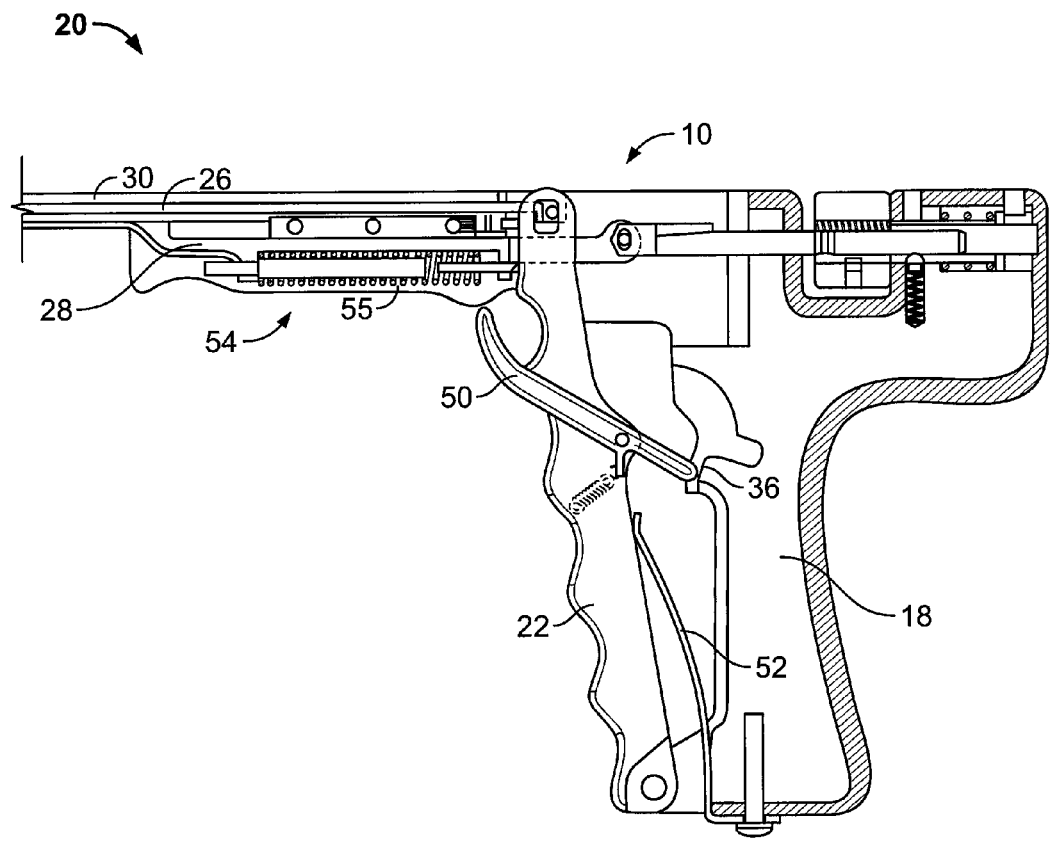
FIG. 9 is a detailed, elevational view of the handle portion showing the trigger portion for being activated or pivoted inwardly towards the handle and a release member in a locked configuration.
Figure 10:
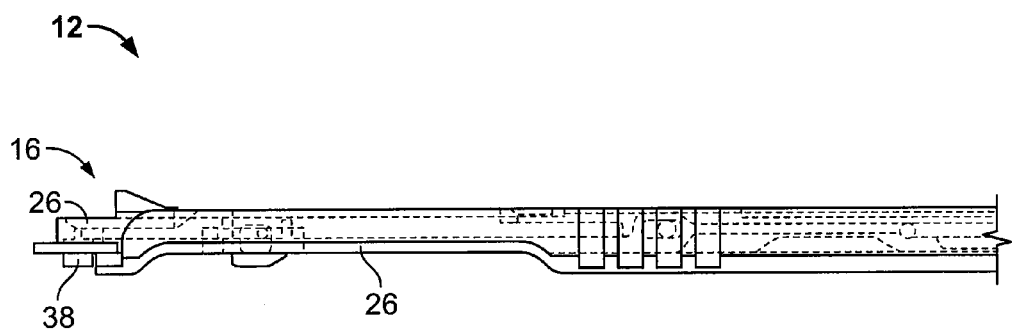
FIG. 10 is an elevational view of the distal end of the insertion instrument showing the gripping mechanism thereon and a latch member for coupling with a disc device (not shown)
Figure 11:
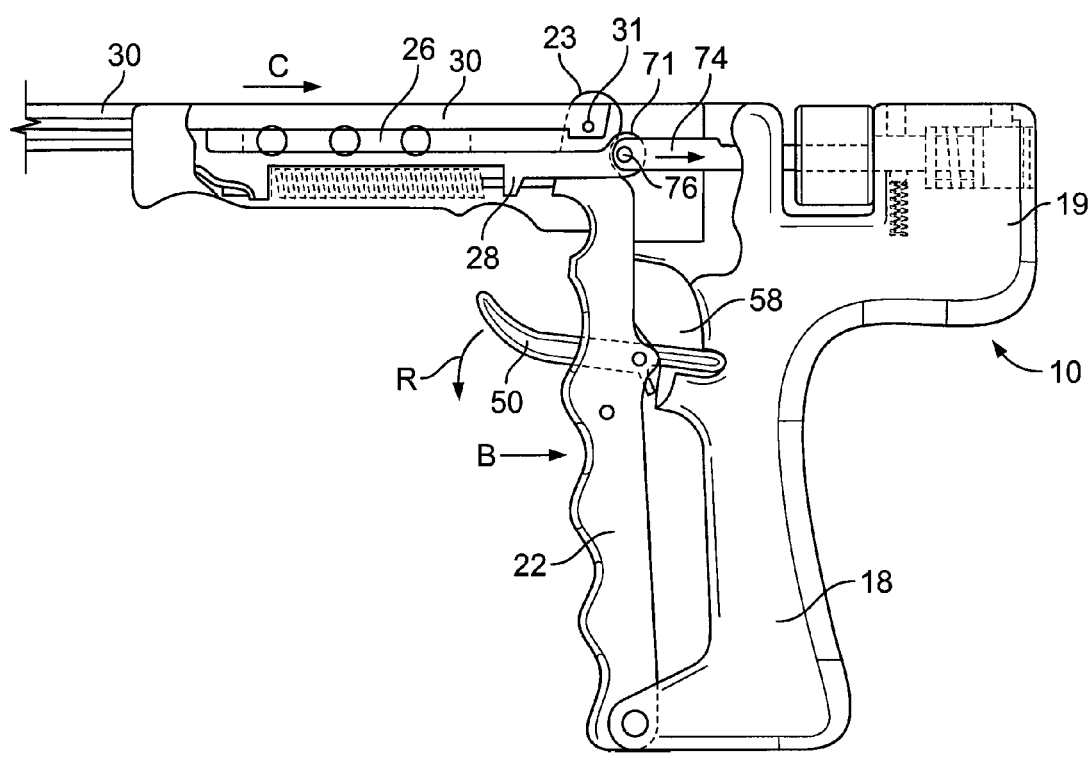
FIG. 11 is a partial, cut-a-way view of the handle portion showing the trigger for being activated or pivoted inwardly towards the handle and the release member in an half-open configuration so that a trigger may be squeezed toward the handle.

Referring to FIGS. 9-11, one embodiment of the actuator 20 is illustrated in more detail. In FIG. 9, the actuator 20 is illustrated as including the trigger 22, a release member 50 that stops or allows actuation of the trigger 22, and a bias element 52 in the form of a leaf spring positioned between the handle portion 18 and the trigger 22 that normally biases the trigger 22 away from the handle portion 18. It will be appreciated, however, that other forms of the actuator 20 are also possible so long as they can be actuated using a generally neutral wrist position.

The actuator 20 further includes a connecting linkage 54 including a bias element 55 in the form of a coil spring coupling the actuator portion in the handle 18 to the lower slidable shaft 28 of the elongate shaft assembly 12. As best shown in FIG. 9, the instrument 10 is in an initial position as it would be received by a surgeon prior to an operation. In this position, the release member 50 is interfering with operation of the actuator 20 because it is abutting a stop surface 56 of the handle 18. In this configuration, the trigger 22 is prevented from being operated by a user. FIG. 10 illustrates the distal end of the elongate shaft 12. In this view, the gripping mechanism 16 is also shown in its initial or stage one position prior to receiving a disc device.

Referring to FIG. 11, to operate the gripping mechanism 16 to grasp a disc device, the release member 50 is first moved to an orientation (Arrow R) that permits operation of the trigger 22. That is, the release member 50 is shifted to a half-open position where it is aligned to be received in a pocket 58 defined in the handle portion 18 so that the trigger 22 may be moved without obstruction. Then, to operate the actuator, the trigger 22 is pivoted (i.e., squeezed) relative to the handle 18 by a user's hand in the direction of Arrow B towards the handle 18.

Figure 12:
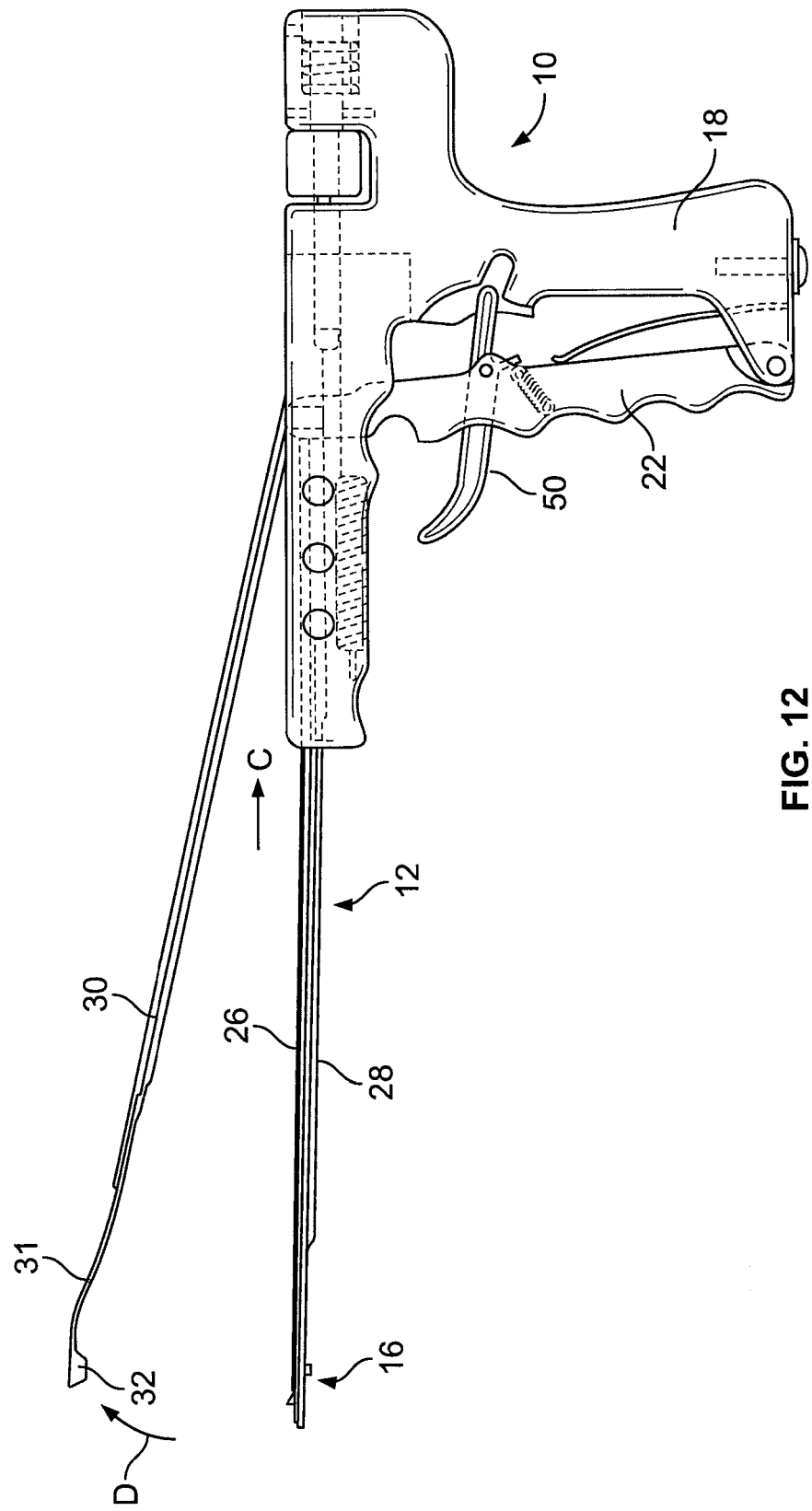
FIG. 12 is an elevational view of the instrument showing the elongate shaft assembly after an initial actuation of the trigger where the upper, shaft portion is pivoted away from the fixed shaft portion.

With such operation, because the upper pivotable shaft 30 of the shaft assembly 12 is connected to the trigger 22 through the pivot 31, it is also shifted rearwardly (Arrow C) upon the squeezing of the trigger 22. With such rearward movement of the shaft 30, it is released from the fixed central shaft 26 and is then free to pivot upwardly (Arrow D) away from the shaft assembly 12 as best shown in FIG. 12. As a result, the claw 32 on the resilient member 31 of the upper shaft 30 is spaced from the shaft assembly 12 and positioned to load a superior portion of an artificial disc device (not shown) on the upper shaft 30.

Figure 13:
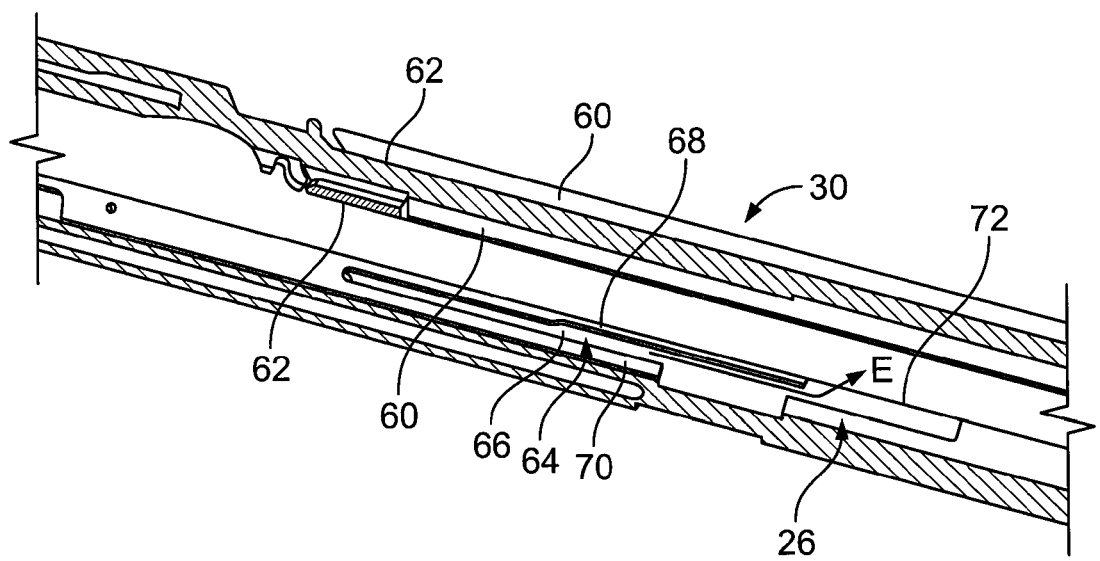
FIG. 13 is an exploded view showing a coupling between an upper, pivotable shaft portion and a fixed shaft portion, the coupling including a track on the fixed shaft portion and a resilient tab portion on the pivotable shaft portion.

Referring to FIG. 13, the pivotable shaft 30 functions as described above because it includes resilient holding arms 60 on opposite sides thereof that have tabs 62 extending orthogonal to the longitudinal axis X of the shaft 12. The tabs 62 are positioned to be received in a recessed track 64 on sides of the fixed shaft 26. Normally, when the pivotable shaft 30 is coupled to the fixed shaft 26 (i.e., prior to actuation of the trigger 22), the tabs 62 are received in a first track portion 66 wherein upper and lower shaft walls 68 and 70, respectively, hold the shaft 30 coupled to the shaft 26 because the tabs 62 are held within the track 64. However, upon the initial actuation of the trigger 22, the upper shaft 30 is retracted rearwardly so that the tabs 62 slide in a corresponding rearwardly direction and eventually are released upwardly via track openings 72 at a rear end of the track 64. As a result, the tabs 62 generally follow Arrow E upon actuation of the trigger 22 to permit the release of the upper shaft 30 from the fixed shaft 26 as previously described and illustrated in FIG. 12.

Figure 14:
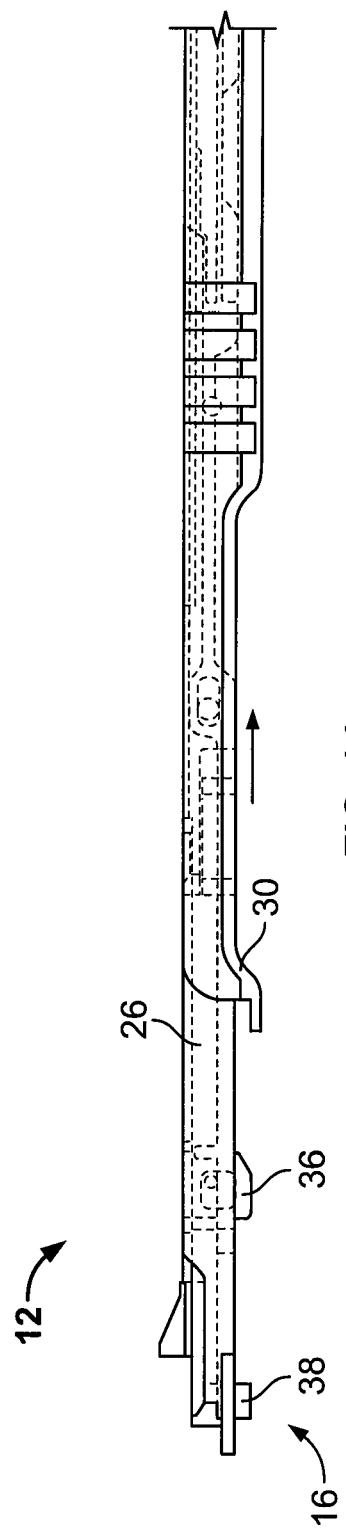
FIG. 14 is an elevational view of the distal end of the insertion instrument showing the gripping mechanism thereon in a second configuration (after a first or initial actuation of the trigger) that is arranged to receive the inferior portion of an artificial disc device (not shown) thereon where the lower, slidable portion of the elongate shaft assembly has been retracted rearwardly relative to the central, fixed shaft by operation of the trigger.

After the first or initial actuation of the trigger 22 as described above, the distal end 14 of the insertion instrument 10 shifts the gripping mechanism 16 thereon to a second or stage two configuration, which is arranged to receive the inferior portion of an artificial disc device (not shown) thereon as best shown in FIG. 14. In this configuration, the lower, slidable shaft 28 of the elongate shaft assembly 12 has been retracted or shifted rearwardly relative to the central, fixed shaft 26 a predetermined amount via the operation of the trigger 22 as described above.

More specifically, the lower shaft 28 is shifted rearwardly due to the interaction of the trigger 22 and a locking shaft 74, which is best described in regard to FIGS. 6 and 11. That is, a proximate end 71 of the slidable shaft 28 is coupled to the locking shaft 74 via a linkage or lock pin 76. The locking shaft 74 is configured to slide along the axis X of the shaft assembly 12 within a bore 75 extending through the proximate end portion 19 of the handle portion 18. The upper end 23 of the trigger 22 extends through a slot 78 formed in the proximate end 71 of the shaft 28. Therefore, upon operation of the trigger 22, the upper end 23 of the trigger 22 abuts the locking shaft 74 and shifts it rearwardly. Because the locking shaft 74 is coupled to the lower shaft 28 via the linkage 76, the rearwardly shifting of the locking shaft 74 also shifts the shaft 28 in the same direction to the retracted position generally illustrated in FIG. 14 described above.

Figure 15:
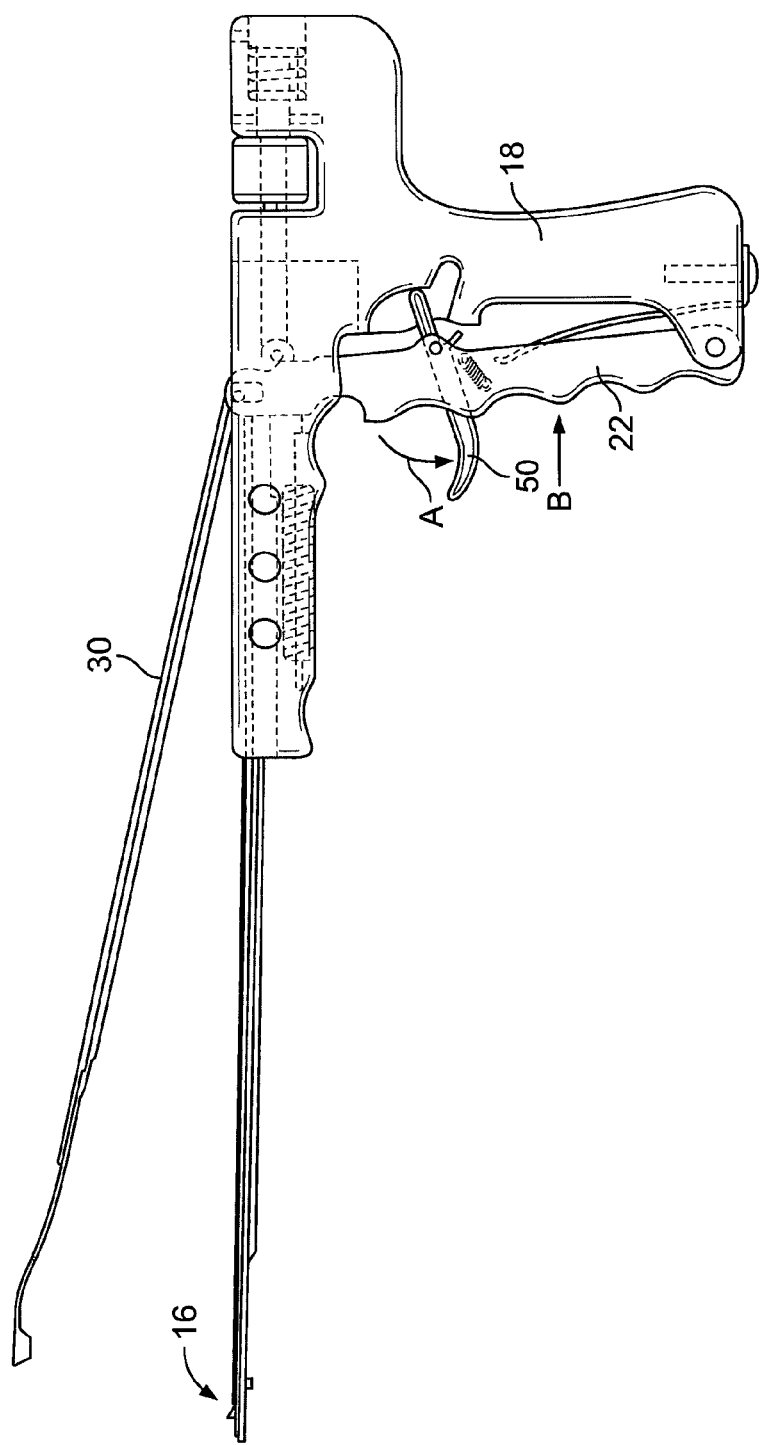
FIG. 15 is an elevational view of the instrument showing the instrument in a configuration for loading the inferior implant portion (not shown) to the gripping mechanism where the release has been moved to a full open position and the trigger is configured for further squeezing.

In one embodiment, to load the inferior portion of an implant to the gripping mechanism 16, the release member 50 is pivoted to a full open position where it is further shifted along the direction of Arrow A (FIG. 15). The trigger 22 is then squeezed further or a second time to configure the instrument 10 to a third or stage three configuration best shown in FIGS. 15 and 16 where the latch member 36 is retracted in the shaft assembly 12 to permit easy insertion of the disc device inferior member to the gripping mechanism 16.

Figure 17:
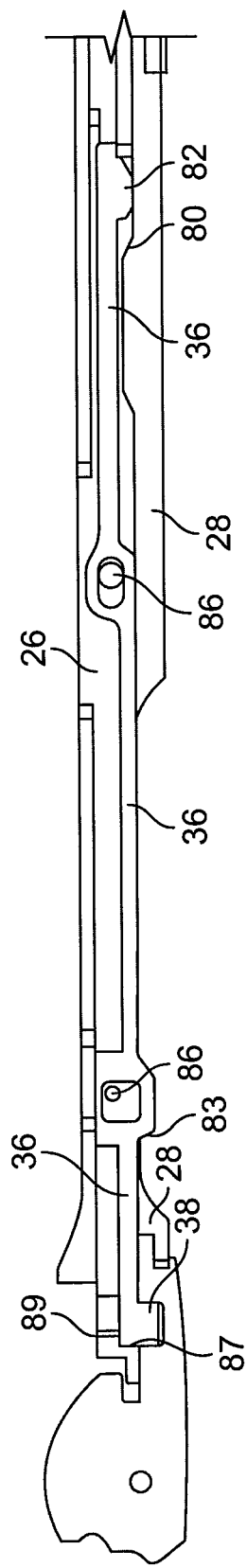
FIG. 17 is cross-sectional view of the distal end of the instrument showing the latch member in a received configuration after an implant has been inserted on the distal end of the elongate shaft assembly.
Figure 18:
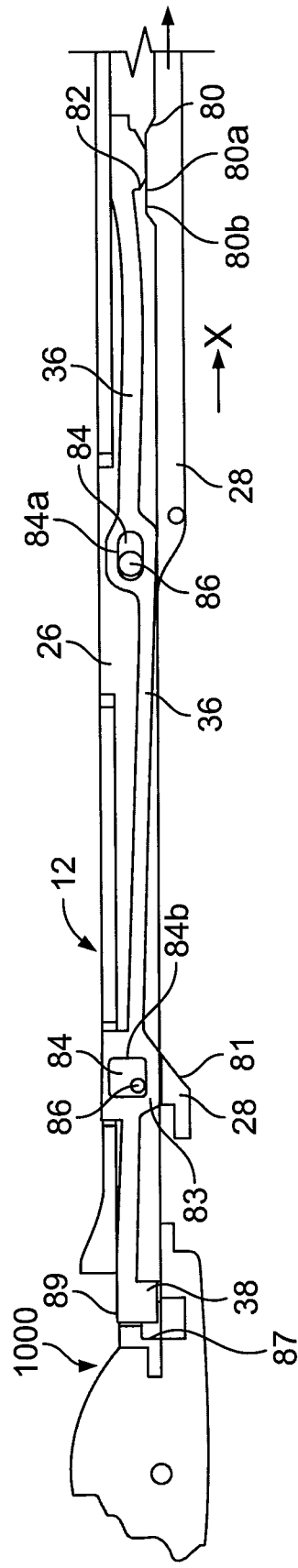
FIG. 18 is cross-sectional view of the distal end of the instrument showing the latch member in a retracted configuration.

By one approach, the latch member 36 is retracted relative to the shaft assembly 12 due to the rearwardly sliding of the lower shaft 28 upon operation of the trigger 22 as best shown in the views of FIGS. 17 and 18. For example, the latch 36 is shown in a down position and the lower shaft 28 positioned forwardly prior to the operation of the trigger 22 in FIG. 17. Upon operation of the trigger 22, the lower shaft portion 28 slides rearwardly so that inclined shaft engagement surfaces 80 and 81 abut inclined latch contact surfaces 82 and 83, which generally cams the latch 36 rearwardly and upwardly so that the post 38 is withdrawn in the shaft assembly 12 as shown in FIG. 18. In a preferred approach, inclined surfaces 80 and 81 do not abut their corresponding latch surfaces 82 and 83 at the same time, but contact each other sequentially through a series of steps. First, the surface 80 of keel 80a cams and lifts surface 82 to position the latch 36 to be retracted where the surface 82 is riding on the top 80b of keel 80a (FIG. 18). As a result, surface 81 will then cam against surface 83 resulting in the latch 36 being moved in the X direction once an upper edge 89 of post 38 clears a step 87 in the tip of the fixed member 26, which permits the post 38 to retract into the fixed member 26. To facilitate such motion, the latch 36 may flex or bend, as exemplified in FIG. 18. When the latch 36 is in the down position of FIG. 17, the abutment of the upper edge 89 of the post 38 into the step 87 generally prevents inadvertent movement of the post 38. To facilitate such camming of the latch 36, it preferably includes openings 84 that extend orthogonal to the direction of the elongate shaft axis X though which alignment pins 86 extend. As shown, a rearward opening 84a is generally elongate to permit shifting of the latch 36 along the elongate shaft axis X while the forward opening 84b is generally rectangular or square to permit both shifting and camming of the latch 36. The size of the openings 84 generally permit the amount of shifting of the latch 36.

Figure 19:
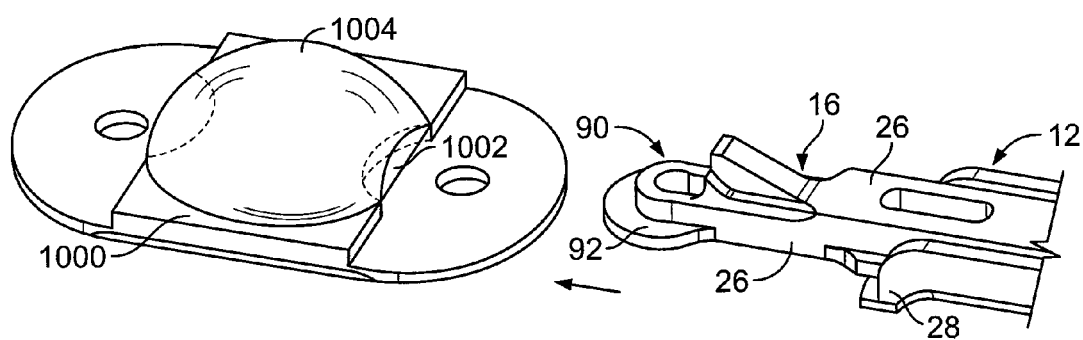
FIG. 19 is a perspective view showing an exemplary inferior implant portion being positioned to engage a tip of the gripping mechanism where an annular flange on the tip of the gripping mechanism is configured for receipt in an undercut slot in a central dome portion of the implant.
Figure 20:
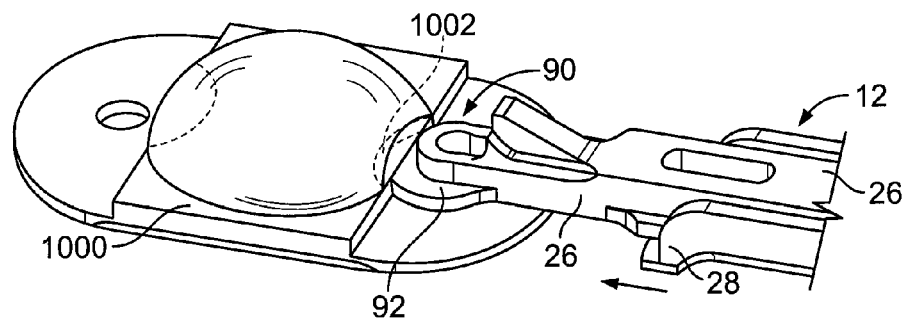
FIG. 20 is a perspective view showing the annular flange fully engaged with the inferior implant undercut slot.

Turning to FIGS. 19-21 and 21A, an exemplary inferior member 1000 of a disc device is shown being secured or mounted to a tip 90 of the gripping mechanism 16. In FIG. 19, the actuator 20 has been activated by operation of the trigger 22 through stages one and two to prepare the gripping mechanism 16 for receipt of the disc device member 1000. In this form, the tip 90 of the gripping mechanism 16 includes an annular flange 92 for being received in an undercut slot 1002 of a central dome portion 1004 of the implant 1000. Because the latch 36 has been retracted to the position of FIG. 18, the implant 1000 is easily coupled to the tip 90 of the gripping mechanism 16 as shown in FIG. 20, where the annular flange 92 is fully engaged with the inferior implant undercut slot 1002. At this point, the lower shaft 28 is still disengaged from the implant 100. The initial positioning of the implant 1000 is preferably undertaken while the trigger 22 is continually being squeezed; however, if desired, the trigger 22 can be squeezed once to release the upper shaft 30 and then squeezed a second time to position the lower shaft 28 for holding the implant 1000.

Figure 21:
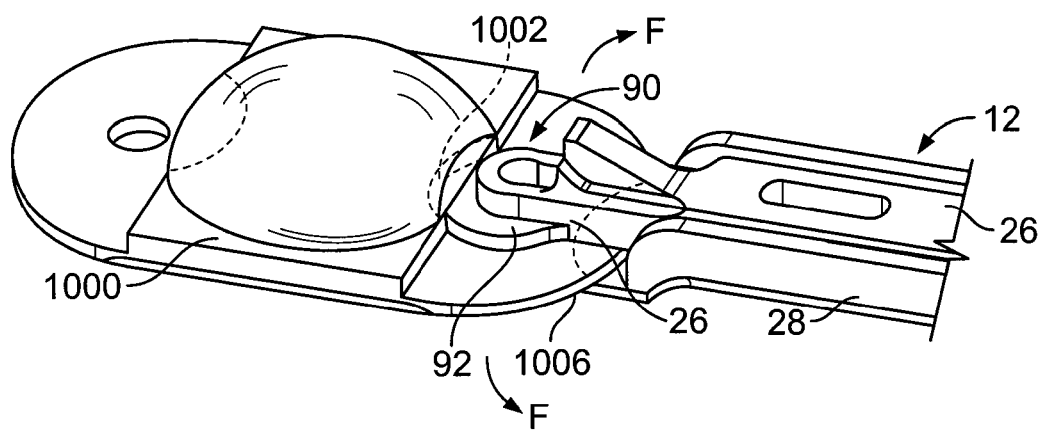
FIG. 21 is a perspective view showing the gripping member after release of the trigger that allows the latch to be inserted into a bore in the implant.
Figure 21A:
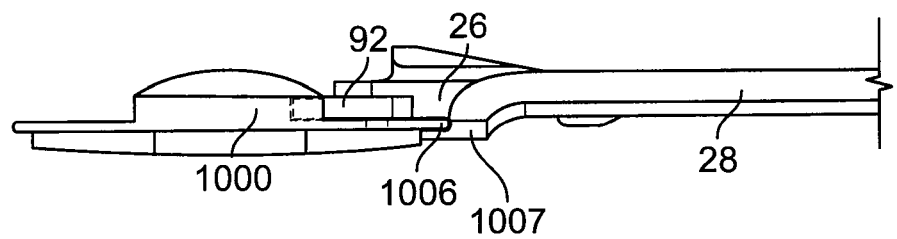
FIG. 21A is an elevational view of the gripping member and implant of FIG. 21.

Once the annular flange 92 is positioned in the undercut slot 1002, the trigger 22 is released to allow the lower, shaft 28 to slide forwardly generally due to the compression of the coil spring 55 by the trigger 22 being pivoted away from the handle 18 by the leaf spring 52. As a result, the lower shaft 28 also slides forwardly where the hook portion 40 abuts against an outer edge 1006 of the implant 1000 as best shown in FIG. 21, and preferably abuts an undercut groove 1007 below the implant outer edge 1006 (FIG. 21A). The forward sliding of the shaft 28 also cams the latch 36 back to its original position where the post 38 is then received in a hole defined in the implant member 1000.

At this point, the implant 1000 is still positionable relative to the tip 90 and can be translated left or right relative to the tip 90 (i.e., Arrows F) for passive steering of the implant if so desired in order to orient the implant for insertion into a patient. Alternatively, the instrument 10 can also be combined with an active steering mechanism, such as the active steering systems described in Application Ser. No. 60/822,027, which is hereby incorporated by reference as if reproduced herein in its entirety.

Figure 22:
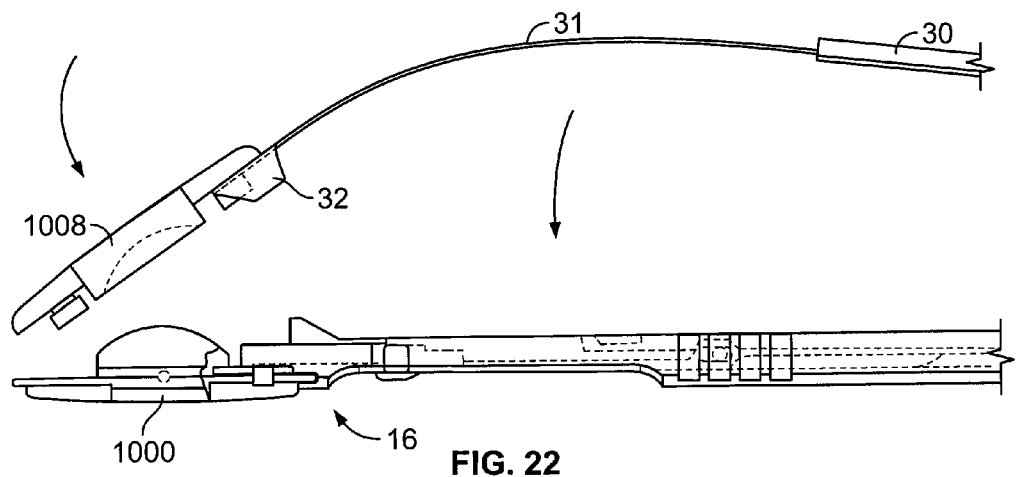
FIG. 22 is a perspective view showing the distal end of the instrument with the upper shaft portion being pivoted downwardly towards the fixed shaft with an exemplary superior implant secured to the distal end of the upper shaft.
Figure 23:
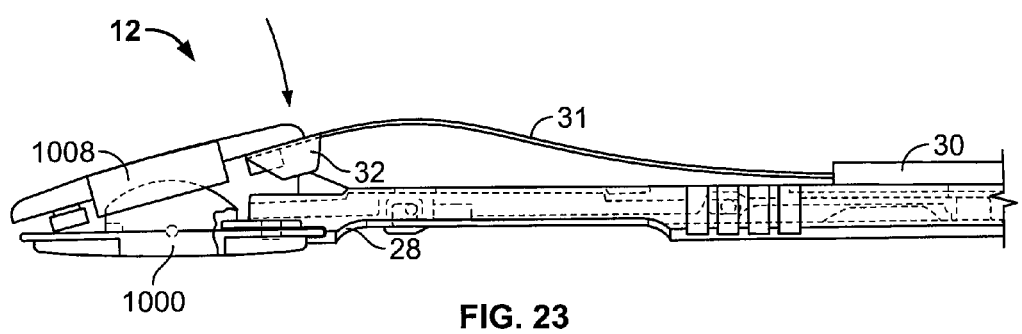
FIG. 23 is a perspective view showing the distal end of the instrument with the upper shaft portion secured to the fixed shaft portion to position the superior implant in a wedge configuration relative to the inferior implant.
Figure 24:
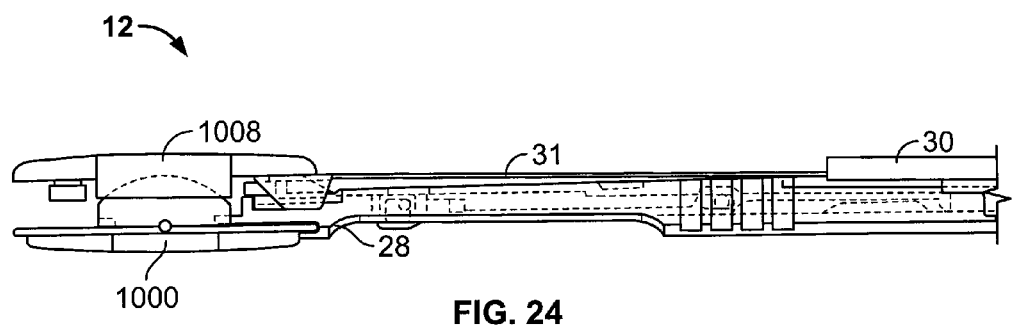
FIG. 24 is a perspective view of the distal end of the instrument showing the positioning of the implant portions after being inserted into a vertebral space between two adjacent vertebrae (not shown) with the superior and inferior implant portions being generally parallel to each other.

Thereafter, the upper shaft 30 is then pivoted downwardly toward the shaft assembly 12 in order to couple the inferior 1000 and superior 1008 implant members into the preferred wedge configuration for implantation as best shown in FIGS. 22 and 23. Once pivoted down towards the shaft assembly 12, the upper shaft 30 is secured to the fixed shaft 26 because the tab portions 62 of the shaft 30 (FIG. 13) are snap-fit into a forward portion 66 of the elongate track recess 64 in the fixed shaft 26. To this end, the tabs 62 are formed on resilient strips configured to shift or flex outwardly orthogonal to the longitudinal axis X to permit the tabs 62 to clear the upper track wall 68 and then shift back to its original position when the tabs 62 are received in the track 64. Once the upper shaft 30 and the fixed shaft 26 are coupled in such a manner, the biased strip member 31 will position the upper implant member 1008 in the wedge configuration relative to the lower implant member 1000 as best shown in FIG. 23. The implant members 1000 and 1008 are then configured for insertion into a vertebral space. Once inserted, the implant portions 1000 and 1008 are oriented generally parallel to each other as shown in FIG. 24 due to the compression forces from the superior and inferior vertebrae (not shown). Once inserted, the trigger 22 can be actuated again to remove the gripping mechanism 16 from the implant as the surgeon pulls back on the handle 18.

Figure 25:
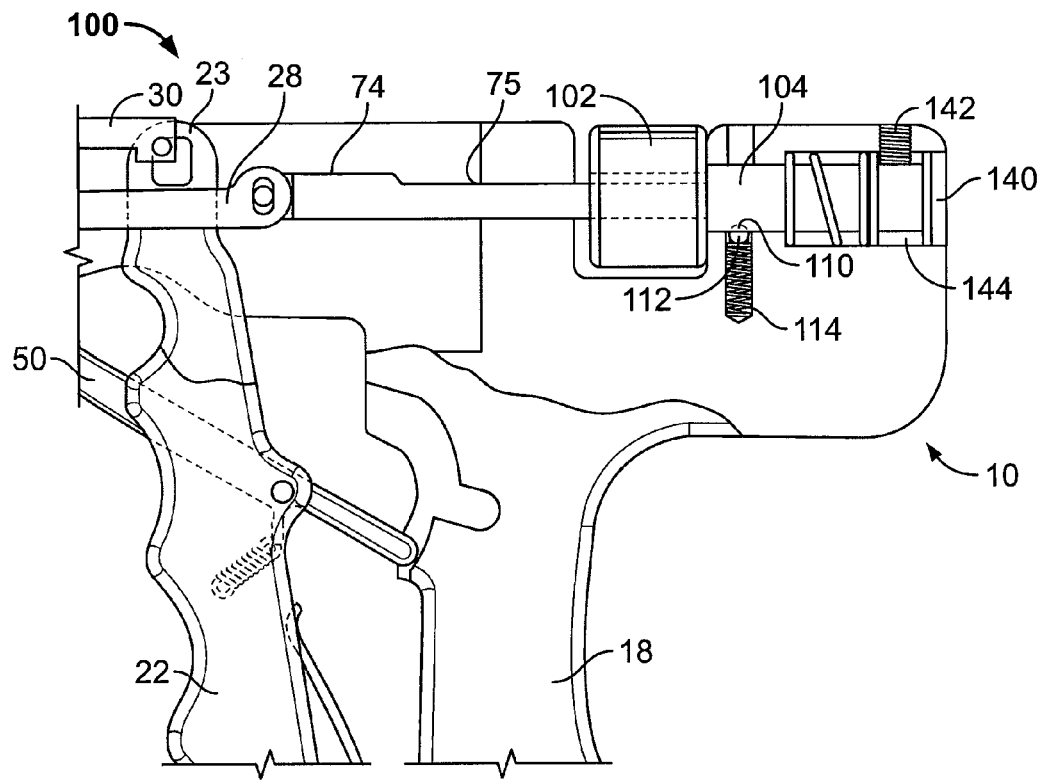
FIG. 25 is a partial cut-a-way view of the locking device showing a lock knob, a coupling member, and a guide tube that is configured to limit the turning or rotation of the lock knob.
Figure 26:
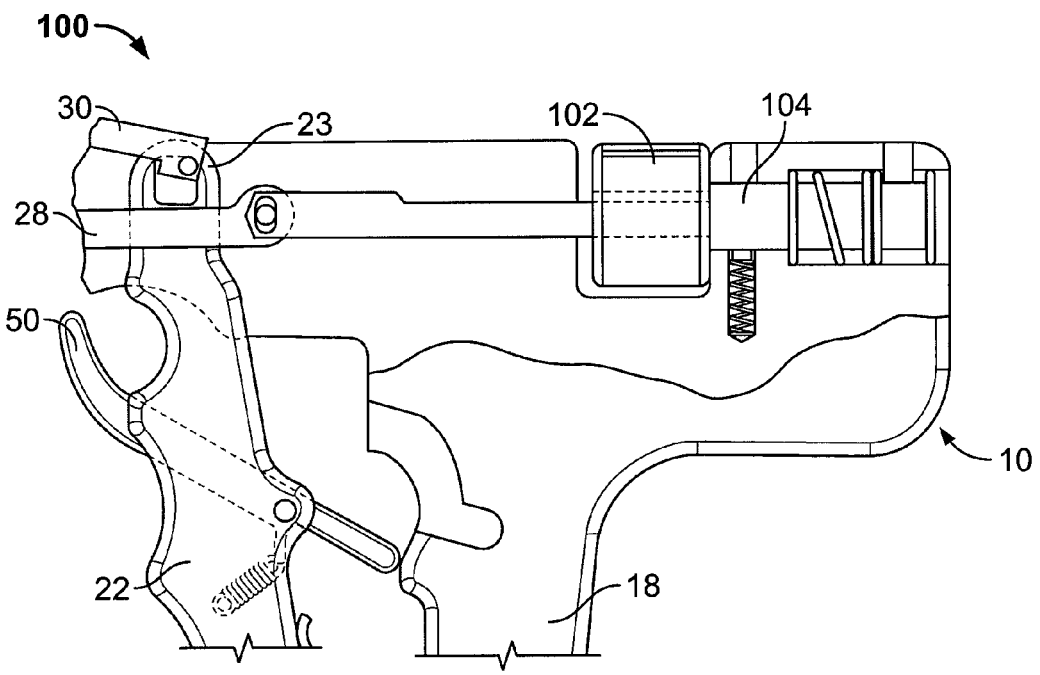
FIG. 26 is a partial cut-a-way view showing portions of the actuating mechanism and a locking device thereof.

Once the implant 1000 is coupled to the tip 90 of the gripping mechanism 16 as described above and optionally oriented left or right (if desired), the disc device is then preferably locked to the instrument 10 prior to insertion into a patient. In a preferred approach, the implant 1000 is locked generally straight along the shaft axis X. Turning to FIG. 25, one form of a locking device 100 is illustrated in more detail.

Preferably, the locking device 100 is positioned and configured so that it can also be operated while the user continues to hold the instrument handle 18 using the generally neutral wrist position. For example, the locking device 100 is positioned so that in some cases the thumb of the users' hand that is grasping the handle 18 can also be used to shift the locking device 100 between a locked and unlocked configuration. (However, the user's other hand may also be used for assistance if the locking force are high.) When locked the locking device 100 prevents further operation of the actuator 20, generally prevents further rotation or steering of the disc device relative to the elongate shaft 12, and also generally fixes the disc device to the instrument 10. In one form, the locking of the instrument 10 is accomplished by turning a lock knob 102 about the shaft longitudinal axis X so that the locking shaft 74 extending between the locking device 100 and the actuating mechanism 20 is restrained from movement. By one approach, the locking is accomplished by turning the lock knob 102 less than one revolution, preferably, less than about 270°.

Referring to FIGS. 25-32, one embodiment of the locking device 100 is illustrated in more detail. As mentioned above, the locking device 100 includes the lock knob 102 for being turned relative to the longitudinal axis X to both lock and unlock the instrument. The locking device 100 also includes the previously described lock shaft 74, which is restrained against translation upon the lock knob 102 being turned. The locking device 100 further includes a guide member 104 that is configured to limit the turning or rotation of the lock knob 52 to less than one revolution. As best shown in FIG. 27, the guide member 104 is a generally elongate cylindrical tube extending along the shaft longitudinal axis X and is coupled to the lock knob 102 via a set screw 106 extending through a bore 108 in the lock knob (FIG. 28) to fixes the lock knob 102 to the guide tube 104. In this manner, the guide tube 104 moves or turns together with the lock knob 102.

To provide indication that the lock knob 102 is in the un-locked configuration, the guide tube 104 preferably includes a recess 110 (FIG. 31) on one side thereof that is configured to positively receive a detent 112, which is biased upwardly into contact with the guide tube 104 by a bias element 114, such as a coil spring. Therefore, when a user is turning the lock knob 102 in the unlocking direction, they will generally know how far to turn the knob 102 because as the detent 112 is positively received in the recess 110, the user will receive an audible or tactile indication that the knob/guide tube assembly is in the unlocked position.

The lock device 100 is operable to lock the gripping mechanism 16 because it has a selective engagement with the lock shaft 74, which when in a locked engagement pushes the lower shaft 28 tightly against the inferior implant lower edge 1006 and, preferably, undercut groove 1007. To this end, as best shown in FIG. 28, the lock knob 102 defines a bore 120 extending therethrough. The bore 120 has internal threading 122 defined on a portion 124 of an inner surface 126 of the bore 120. As shown, the bore 120 has a generally D-shaped profile that is configured to cooperate with a similar D-shaped profile on the lock shaft 74 as will be further described below. The internal threading 122 forms part of the selective engagement between the knob 102 and the lock shaft 74.

Turning to FIG. 29 the lock shaft 74 and another portion of the selective engagement is illustrated in more detail. Preferably, the lock shaft 74 is a generally cylindrical, elongate member having external threading 130 on at least a portion thereof and no threading on another portion 132 thereof. As shown, the lock shaft 74 has a D-shaped profile with a curved or arcuate portion 134 and a flat portion 131. In particular, the external threading 130 extends partially around the lock shaft 74 such as on the curved D-shaped portion 134. With such configuration, the partial threading 130 of the lock shaft 74 permits the selective engagement with the partial threading 122 of the lock knob bore 120 in order to lock the instrument when both partial threadings 122 and 130 are mated. That is, for example, when the lock knob 102 is turned about the longitudinal axis X of the instrument 10 (with a user's thumb for example) so that the threading 122 of the knob 120 is threadably mated with the threading 130 of the partial threading portion 134 of the lock shaft the instrument is locked. In this configuration, the instrument 10 is locked because the mating of the threads 122 and 130 prevents further operation of the trigger 22. The implant coupled to the distal end of the shaft 12 is also restrained from movement because the lock shaft 74 is translated towards the distal end of the shaft assembly 12, which also translates the shaft 28 into a tight engagement with the implant inferior member 100 to restrain it from motion relative to the elongate shaft 12.

To unlock the instrument 10, the lock knob 102 is turned about the longitudinal axis X in a reverse direction. When unlocking the lock device 100, the threading 122 of the knob bore 120 is unmated from the threading 130 of the lock shaft portion 132 so that the flat portion 131 of the D-shaped lock shaft 74 and flat portion 125 of the lock knob bore 120 correspond with each other to permit the shaft 74 to translate through the bore 120. The artificial disc device in the gripping mechanism 16 is then generally free to move or pivot relative the elongate shaft and be removed therefrom because the shaft 28 is no longer tightly compressed against the implant lower edge 1006 and, preferably, against undercut groove 1007. Such movement is possible because, in the unlocked position, the lock shaft 74 is generally free to translate or slide along the longitudinal axis X through the lock knob bore 120 because there is no mating between the corresponding threading 122 and 130.

Figure 30:
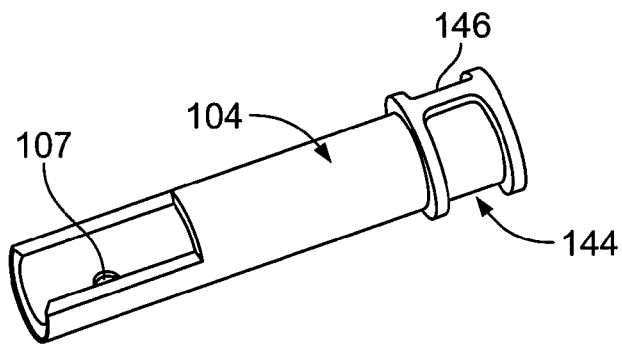
FIG. 30 is perspective view of the guide member that is arranged and configured to limit the turning of the lock knob showing a bore positioned to receive a set screw for securing the guide member to the handle.
Figure 31:
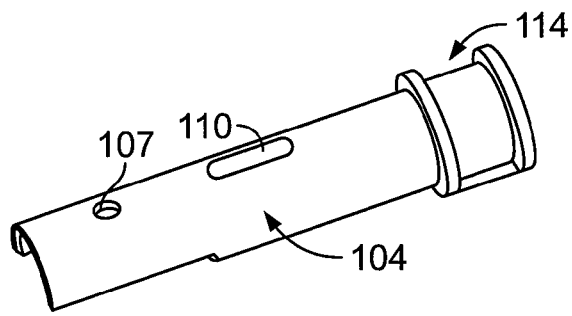
FIG. 31 is a perspective view of the guide member showing an annular channel on a distal end thereof that has a stop portion thereon that engages a protrusion extending through the handle upon rotation of the guide member and lock knob assembly to limit turning or rotation thereof.

In one aspect, the lock knob 102 is turned less than about one revolution or less than about 270° to mate and un-mate the threads 122 and 130. To this end, the turning of the lock knob 102 is preferably limited by the cooperation of the guide tube 104 with the locking knob 102. FIGS. 30 and 31 are perspective views of the guide tube; comparing these views to FIGS. 25 and 27, it can be seen how the guide tube 104 limits turning of the lock knob 104. It will be appreciated, however, that other mechanisms can be employed to limit turning or rotation of the lock device.

As previously discussed, the guide tube 104 is joined to the lock knob 102 via the set screw 106, which is received through a bore 107 in the guide tube 104 so that the guide tube 104 turns as an assembly along with the lock knob 102. The guide tube 104 is inserted through an opening 140 in the instrument handle 18 so that it is generally positioned along the shaft axis X. In this manner, the guide tube 104 is configured for being turned within the opening 140 in cooperation with the turning of the lock knob 102. However, the guide tube 104 is preferably restricted from turning a full revolution via a stop mechanism. For example, a protruding member 142, such as a set screw, pin, protrusion, or the like extends through the handle portion 18 and into an annular channel 144 in the guide tube 104. The channel 144 includes a stop 146 thereon (FIG. 30) that is positioned to engage the protrusion 142 upon a predetermined turning or rotation of the guide tube 104 and lock knob 52 assembly to limit turning or rotation thereof. That is, when the protrusion 142 contacts the guide tube stop 146, the lock knob 102 is substantially hindered from further rotation. In this manner, the locking device 100 limits over rotation thereof that could potentially damage the instrument 10.

Figure 32:
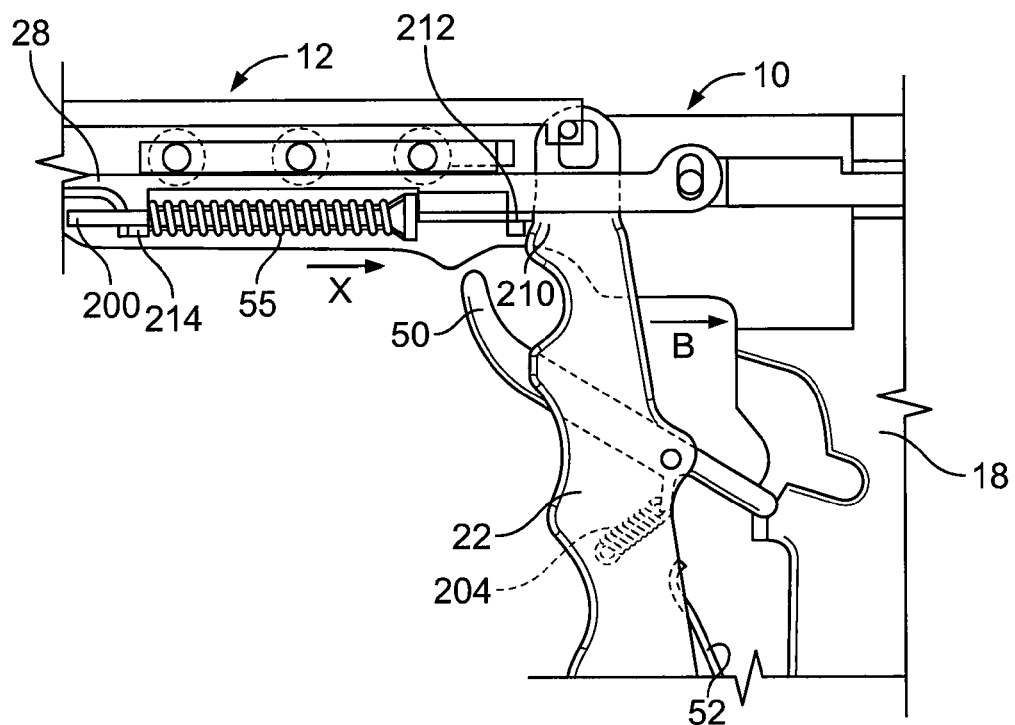
FIG. 32 is an elevational view of the instrument showing the actuating mechanism with the coupling member joined to the lower shaft portion and a bias member that biases the lower shaft portion forwardly.

The instrument also preferably includes a number of additional bias elements to facilitate ease of instrument operations. For instance, as best shown in FIG. 32, a plunger shaft 200 and the bias element 55 are illustrated as being operative for providing a forward motion of the sliding shaft 28 along the shaft axis X. That is, the plunger shaft 200 and the compression of the spring 55 are configured upon release of the trigger 22 to apply a forwardly directed force along axis X to the sliding shaft 28 that shifts the shaft 28 forwardly. For example, upon releasing the trigger 22, the bias element 52 helps bias the trigger into an un-activated direction. At the same time, an upper end 210 of the trigger 22 abuts an end 212 of the plunger shaft 200 which loads or applies a compression force to the spring 55 that shifts the sliding shaft 28 forwardly when the spring 55 applies the force to abutments 214 of the sliding shaft 28. Optionally, the actuator 20 also includes a bias element 204 coupled to the release member 50. The bias element 204 is configured to bias the release member 50 into the locked position as shown in FIG. 32, when not being activated by the user.

As discussed above, the instrument 10 is advantageous because it provides for grasping an implant, locking the implant relative to the instrument, inserting the implant into an intervertebral space, un-locking the instrument, and removing the implant using a generally neutral wrist position and, preferably, only a single actuation control that can also be operated using a generally neutral wrist position. Because the instrument 10 preferably includes the handle portion 18 in the form of a pistol grip and includes the locking device 100 adjacent the pistol grip, the user can operate and lock the instrument 10 in some instances using the same hand, which frees the other hand for other surgical tasks.

Figure 33:
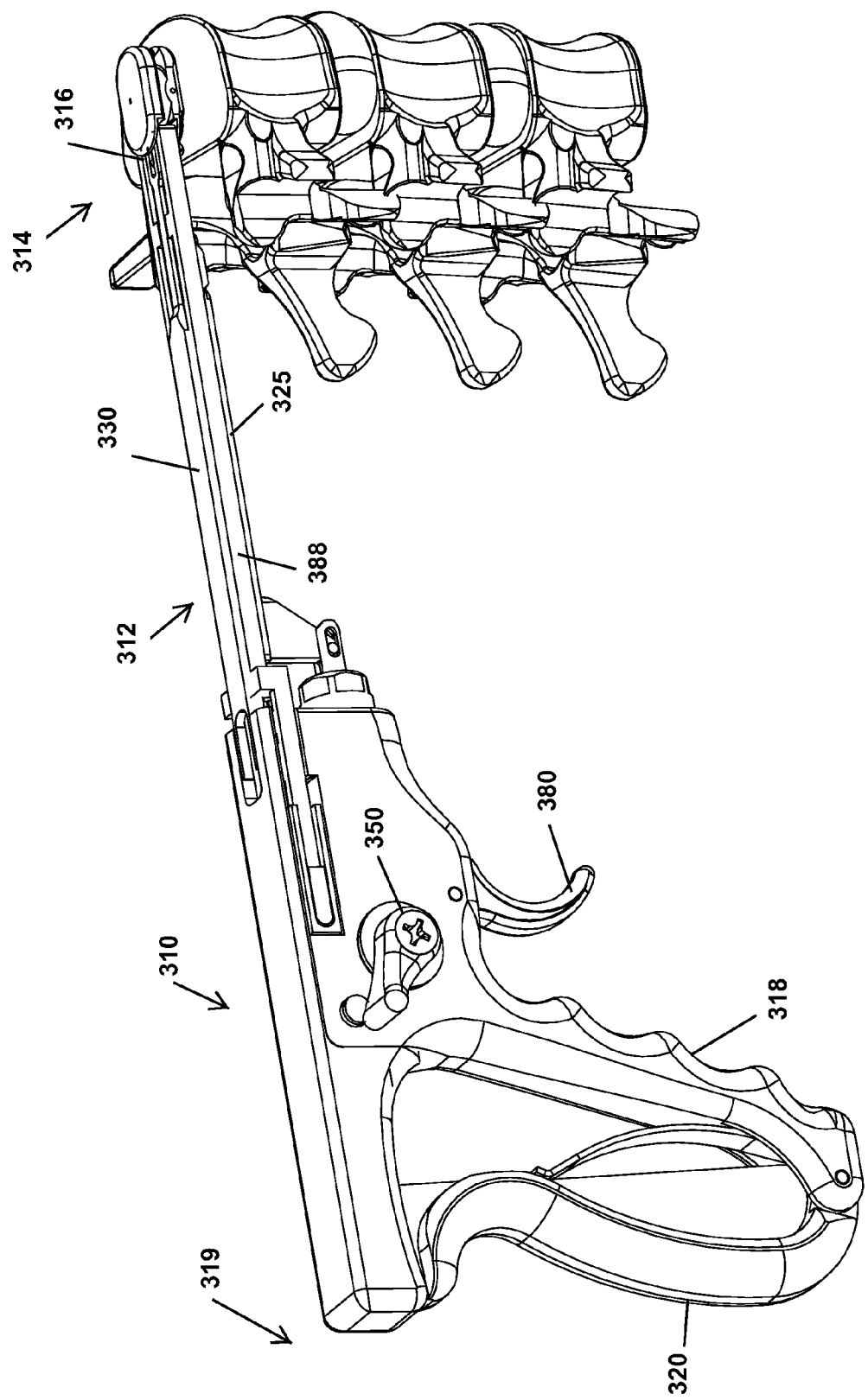
FIGS. 33 and 34 are perspective views of another instrument according to the invention.

A further example of an insertion instrument 310 is shown in FIGS. 33-47. As with the previous embodiment (FIGS. 1-32), the instrument 310 shown in FIG. 33 is a pistol-grip inserter for insertion of a two-part implant, allowing the instrument to be held in a wrist-neutral position as the implant is inserted into a patient's spine. The instrument 310 has an elongate shaft assembly 312 at the distal end 314 of the instrument and a handle actuator 320 at the proximal end 319 of the instrument, and the instrument secures and releases an implant using a single actuator 320 coupled to the handle. However, this instrument includes additional actuators to operate features not included in the previous instrument of FIGS. 1-32. The instrument is shown in FIGS. 33 and 34 introducing an implant into the space between two vertebrae.

The handle actuator 320 is pivoted toward and away from a fixed handle portion 318 in order to operate a gripping mechanism. As will be further described below, movement of the handle actuator 320 shifts a main or central shaft 326 of the instrument (FIG. 35) linearly relative to an upper shaft 330 and lower shaft 328 of the instrument's shaft assembly 312, and shifts a latch portion 337 of a gripping mechanism 316 of the central shaft between locked and unlocked positions to secure and release the lower member of a spinal implant. As will be described further below, squeezing of the handle actuator 320 allows a surgeon to both receive and release the implant from the gripping mechanism 316 of the instrument, and release of the handle actuator 320 secures the implant to the instrument.

A separate actuator, for instance knob actuator 350 shown in FIG. 33, may be provided to limit pivoting of the implant once it is secured to the gripping mechanism 316 of the elongate shaft assembly 312. For instance, turning of the knob actuator 350 a small amount applies a forward force on the instrument's lower shaft 328, causing the lower shaft 328 to engage and brace against the lower surface of the implant as it is held by the gripping mechanism 316. The lower shaft 328 has a distal end configured to engage with the implant in a manner that stabilizes the connection between the implant and the insertion instrument.

Figure 34:
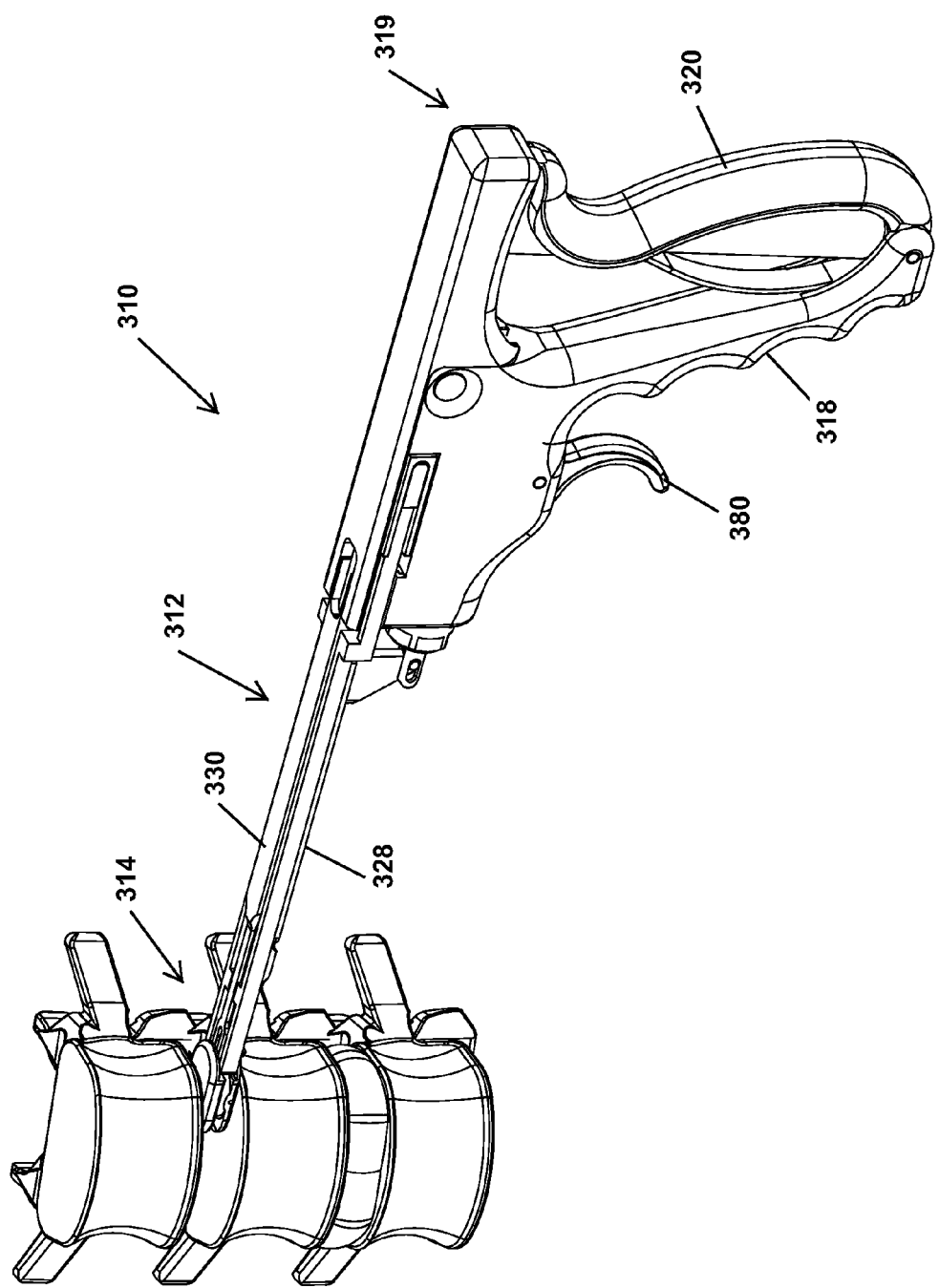

The instrument may also be provided with a member that causes pivoting of an implant held by the gripping mechanism 316, such as the elongate steering shafts 388 shown in FIGS. 33 and 34. In the illustrated instrument, two steering shafts may be releasably connected to the instrument, and only one is connected at any given time to pivot the implant either to the left or right as desired. Securing a steering shaft 388 to the right side of the elongate shaft assembly 312 causes pivoting of the implant to the left when the steering shaft 388 is shifted forward. Alternately, securing a steering shaft 388 to the left side of the elongate shaft assembly 312 causes pivoting of the implant to the right. A trigger mechanism 380 or other actuator may be provided to drive the steering shaft 388 into contact with the implant. Of course, instead of having two removable pivot inducer members, the trigger mechanism or other actuator may be configured to selectively engage one or the other of the steering shafts, or separate actuators for each steering shaft may be provided.

Figure 35:
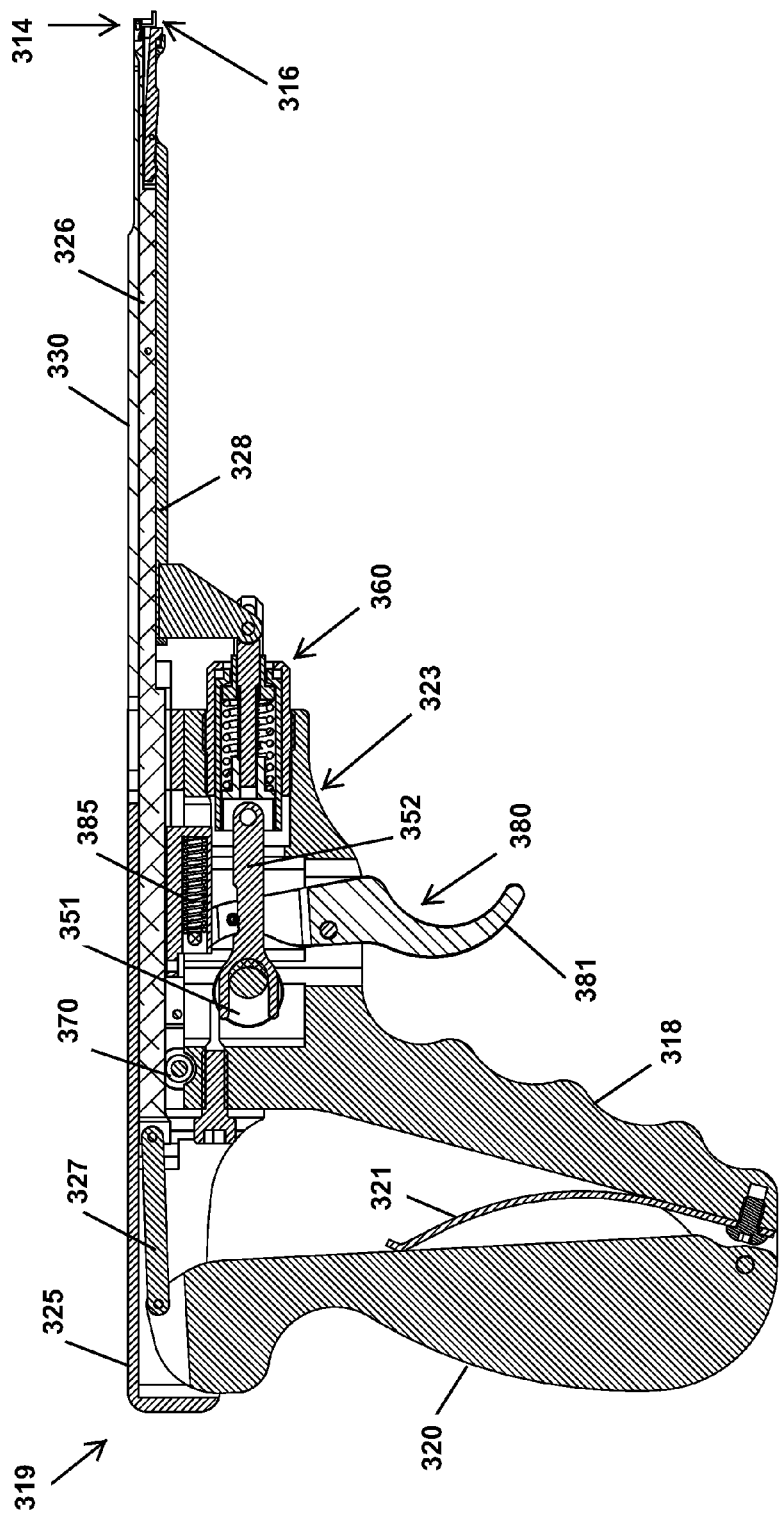
FIG. 35 is a side cross-sectional view of the instrument from FIG. 33.
Figure 36:
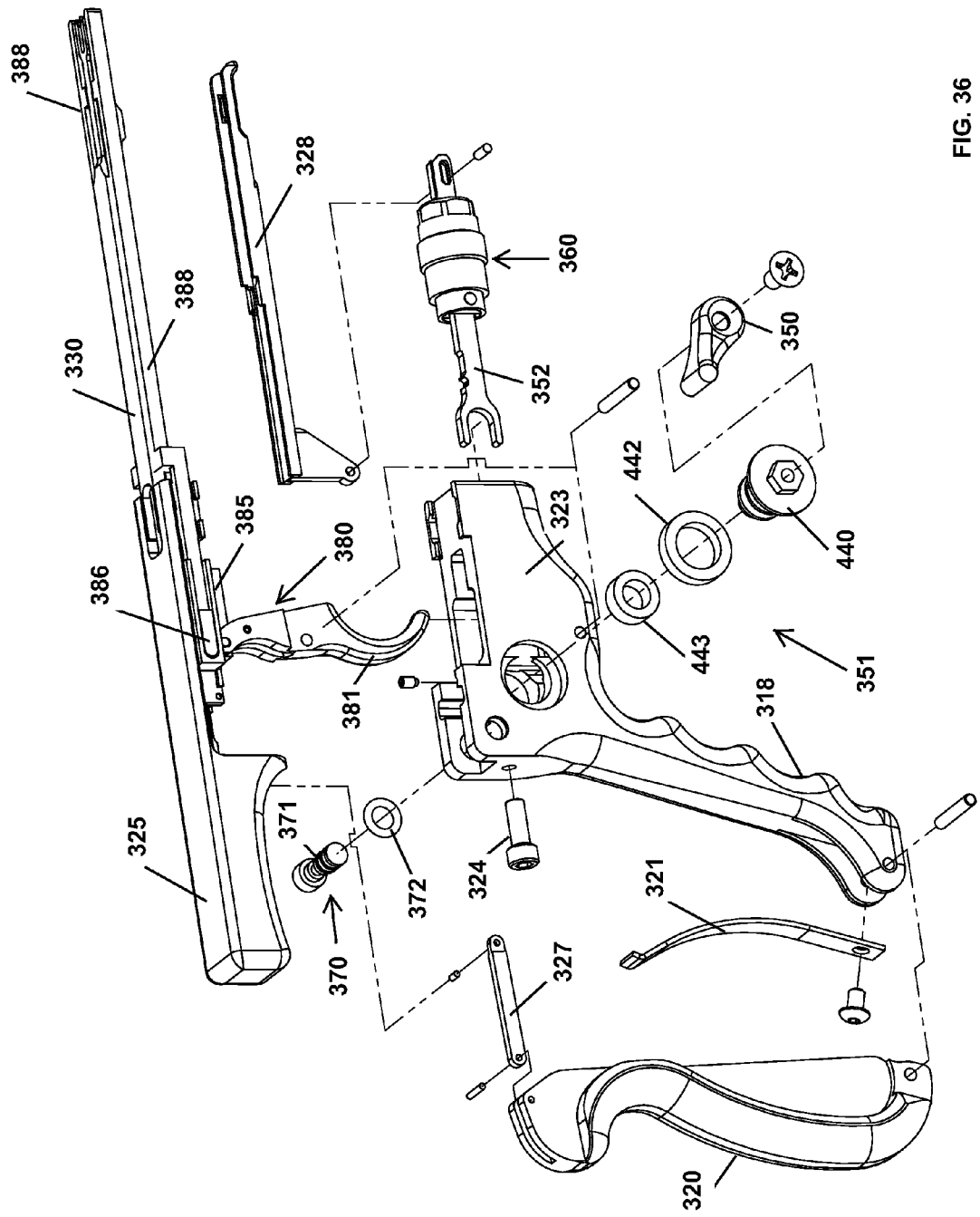
FIG. 36 is an exploded view of the instrument from FIG. 33.

A cross-sectional view of the instrument of FIG. 33 is shown in FIG. 35 and an exploded view is shown in FIG. 36. From these views, it can be seen that the main or central shaft member 326 that secures the implant is coupled to the handle actuator 320 by a linkage member 327. The central shaft member 326 is slidably disposed between a cover member 325 and upper shaft member 330 on its upper side and the fixed handle 318 and lower shaft member 328 on its lower side. The fixed handle portion 318 also forms a housing 323 for several moveable components, including actuator components coupled to the lower shaft member 328. The cover member 325 forms the top of the instrument and is mounted to the fixed handle member 318 by a bolt 324. The upper shaft member 330 is pivotably coupled to the cover member 325 so that it is capable of pivoting away from the central shaft member 326.

The handle actuator 320 is pivotably connected to the fixed handle portion 318 so that pivoting of the handle actuator toward the fixed handle shifts a linkage member 327, and consequently the central shaft member 326 coupled thereto, forward. Forward shifting of the central shaft member 326 allows it to engage and disengage implants, as further explained below. A leaf spring 321 or similar mechanism may be provided to bias the handle actuator 320 away from the fixed handle portion 318 so that it returns to an initial position when released, shifting the central shaft 326 toward the proximal end 319 of the instrument. Squeezing the handle actuator 320 a first time shifts the central shaft member 326 forward to receive an implant member, and releasing the actuator 320 allows the force of the leaf spring 321 to shift the central shaft member 326 backward to secure the implant. Squeezing the handle actuator 320 a second time advances the central shaft 326 to release the implant member.

A locking or safety mechanism 370 to permit or inhibit shifting of the central shaft member. In the illustrated form, the safety mechanism 370 includes a safety piston 371 that selectively engages the underside of the central shaft member 326. An annular spring member 372 surrounds one end of the safety piston 371 to provisionally hold it in the locked or unlocked position until adequate force is provided by the user to shift the safety piston 371 to the other position. When the safety mechanism is engaged, the central shaft member 326 and handle actuator 320 are locked in place, preventing accidental disengagement of an implant member.

The lower shaft member 328 is shifted linearly by an exterior knob actuator 350 that is connected to a rotating cam device 351. Rotation of the cam device 351 by turning of the knob actuator 350 shifts the position of a cam linkage 352 that is coupled to the lower shaft member 328 through a spring pack 360 that dampens the force exerted by the rotating cam device 351 and cam linkage 352. Turning of the knob advances the lower shaft member 328 in order to abut an implant held by the gripping mechanism 316 at the distal end 314 of the instrument, stabilizing the implant for insertion into the patient.

As further explained below, the spring pack 360 is preloaded to apply a preset amount of force for shifting the lower shaft member 328, with compression of the springs in the spring pack ensuring that the preset amount of force is not exceeded regardless of the force applied to the knob actuator 350 or small size variations of components of the instrument or implant. Thus, the spring pack automatically adjusts for variations in parts due to machining tolerances, reducing the time and cost required for manufacture and assembly of the instrument.

Returning the knob actuator 350 and cam device 351 to their initial positions reduces the force applied by the lower shaft member 328 to the implant member, permitting the implant member to pivot relative to the gripping mechanism 316.

When the lower shaft member 328 is retracted away from the distal end 314 of the instrument, a trigger mechanism 380 may be used to induce pivoting of the implant held by the gripping mechanism 316. The illustrated trigger mechanism includes a trigger lever 381 that pivots to shift a steering block 385. An elongate steering shaft may be connected to either side of the steering block 385 so that shifting of the trigger lever 381 advances the steering shaft toward the gripping mechanism 316 and into abutment with an implant secured by the gripping mechanism, steering the implant away from the side contacted by the steering shaft. Although both steering shafts are shown secured to the steering block 385 in FIGS. 33-34 and 36, only one steering shaft would be connected to the steering block at any given time in order to effectively steer the implant in one direction or the other. If desired, clip members 386 may be provided to quickly secure and release the elongate steering shafts 388.

Figure 37:
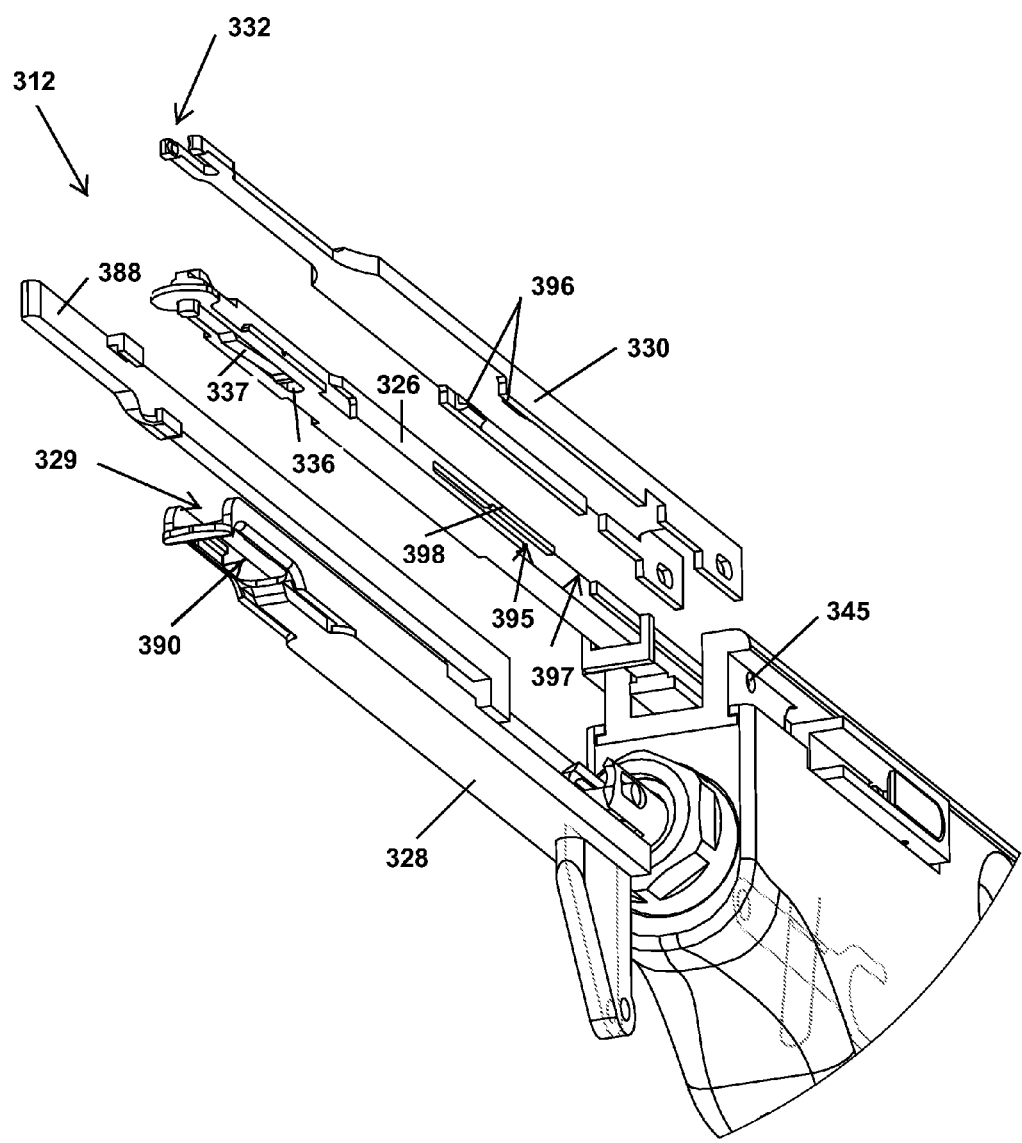
FIG. 37 is an exploded view of the shaft assembly of the instrument from FIG. 33.
Figure 40:
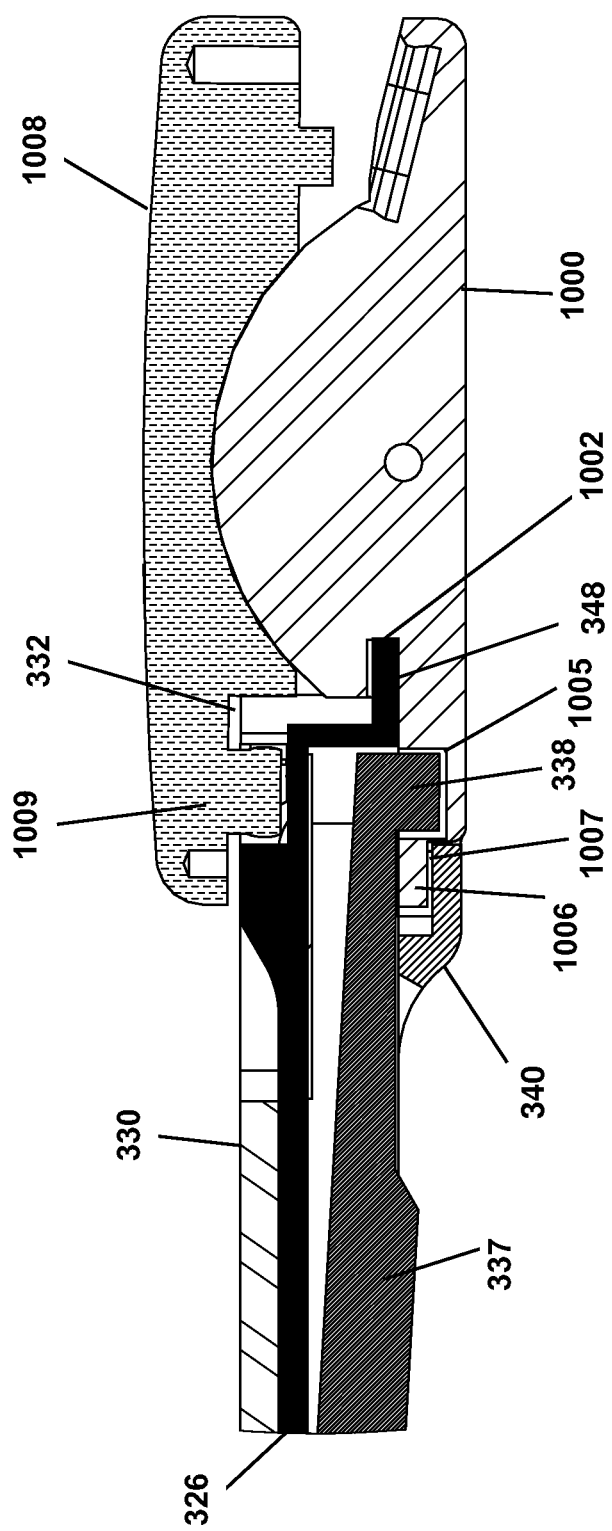
FIG. 40 is a detailed side cross-sectional view of the shaft assembly securing an implant.

Details of the shaft members that make up the elongate shaft assembly 312 can be seen from the partially exploded view of the in FIG. 37. The upper shaft 330 is configured with a grasping claw 332 at its distal end that engages a post or similar structure of an upper implant member (as shown in FIG. 40). Unlike the central shaft member 326, the upper shaft member 330 does not translate significantly along the axis of the elongate shaft assembly, although the upper shaft member 330 may be partially or wholly flexible so that the grasping claw 332 at the end of the upper shaft 330 maintains its positioning relative to the gripping mechanism 316 of the central shaft member 326, similar to the upper shaft member shown in FIGS. 22-24. The upper shaft member 330 also is pivotably connected to the fixed handle portion 318 of the instrument through pins 345 that are disposed in openings at the proximal end of the upper shaft member 330 and in the fixed handle 318. Pivoting of the upper shaft member 330 away from the rest of the shaft assembly 312 allows an upper implant portion to be more easily loaded into the grasping claw 332 portion of the upper shaft member 330.

Pivotability of the upper shaft member 330 is controlled by interaction between the upper shaft member and central shaft member 326. Inwardly directed tabs 396 on the lower portion of the upper shaft member 330 are configured to slide within lateral guide tracks 395 formed on the sides of the central shaft member 326, maintaining a relatively parallel relationship between the central shaft member 326 and the upper shaft member 330. Ledges or flanges 398 at the top of the guide tracks 295 interact with the tabs 396 of the upper shaft member 330 to prevent the upper shaft member 330 from pivoting away from the rest of the shaft assembly 312 when the central shaft member 326 is in its retracted position. When the central shaft member 326 is shifted forward, the upper shaft member remains coupled thereto until the tabs 396 of the upper shaft member 330 become aligned with an upward opening 397 in the central shaft guide track 395, releasing the upper shaft member 330 from the central shaft member 326 and permitting the upper shaft member 330 to pivot upward (as in FIG. 39).

Advantageously, the tabs 396 of the upper shaft member 330 may be sloped inward on their lower surfaces so that the upper shaft member 330 may be re-engaged with the central shaft member 326 irrespective of the positioning of the central shaft. In other words, the tabs 396 may be configured with one-way locking lower camming surfaces so that applying a downward force to the upper shaft member 330 cams the tabs outward slightly so that they slide into a snap-fit past the upper ledge 398 of the central shaft member 326. Without sloped camming surfaces on the upper side of the tabs 396 or the lower side of the upper ledge 398 of the central shaft member, the tabs 396 cannot escape the guide track 395 and the upper shaft member 330 will be held generally parallel to the central shaft member 326 until the tabs 396 again become aligned with the upward opening 397 of the guide track 395.

As can also be seen from the partially exploded view of FIG. 37, the central shaft 326 includes a cavity 336 opening at its lower side which pivotably receives a latch member 337 that pivots to secure and release an implant engaged by the distal end of the central shaft. The central shaft 326 is also slidably disposed through an axial channel 329 formed through a portion of the lower shaft member 328. An opening 390 in the bottom of the lower shaft allows the latch 337 held by the central shaft member 326 to pivot when the central shaft member 326 is shifted to particular positions relative to the lower shaft member 328.

Figure 38:
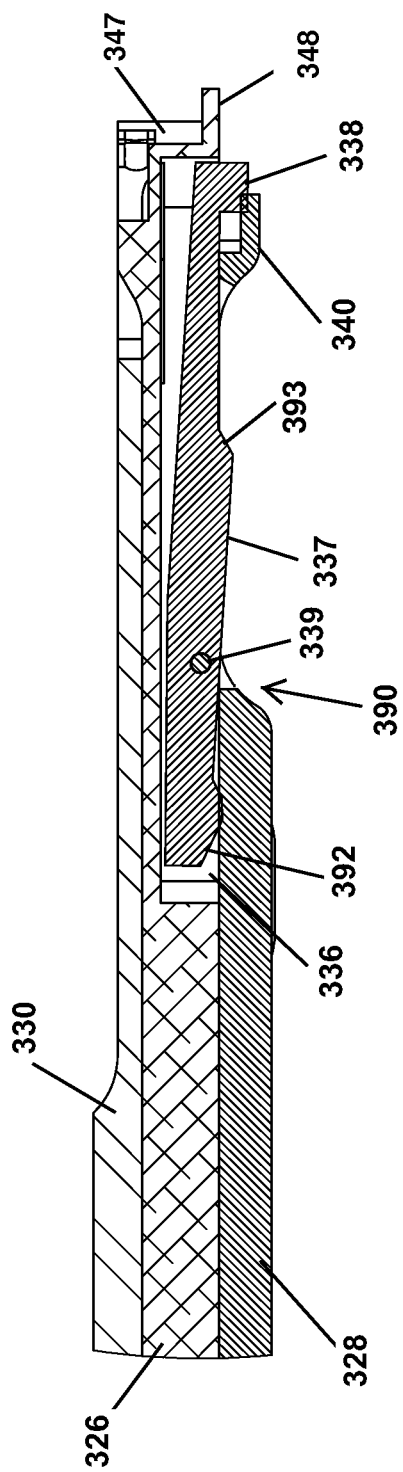
FIG. 38 is a detailed side cross-sectional view of the shaft assembly of the instrument shown in FIG. 33, including detail of the latch member and other structures used to secure an implant to the tip of the instrument.
Figure 39:
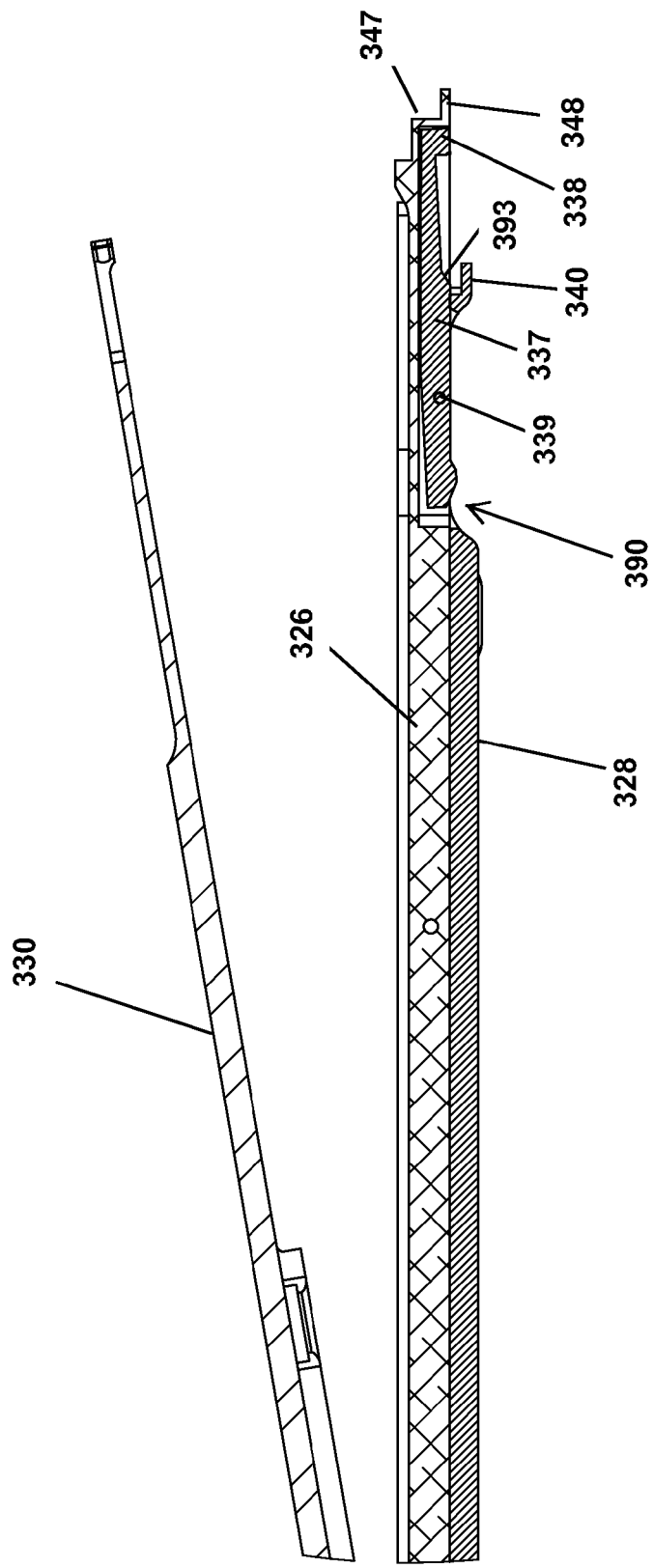
FIG. 39 is a detailed side cross-sectional view of the shaft assembly as in FIG. 38 with the central shaft member shifted forward and the latch member pivoted to a release position for releasing or receiving an implant.

The relationship between the central shaft member 326 and lower shaft member 328 is shown in cross-section in FIGS. 38 and 39. In FIG. 38, the central shaft member 326 is shown in a retracted position. The latch member 337 is shown disposed in the cavity 336 of the central shaft member 326, and is pivotably mounted to the shaft member by a post 339 that couples the latch member 337 to the central shaft member 326. When the central shaft member 326 is in the retracted position, the lower shaft member 328 forces the rear camming portion 392 of the latch member upward into the central shaft cavity 336, so that the post 338 of the latch member 337 is pivoted downward for engaging an implant. The hook end 340 of the lower shaft member 328 and post 338 of the latch member 337 can cooperate to grasp and stabilize an implant member disposed therebetween.

When the central shaft member 326 is shifted forward by the squeezing of the handle actuator (320 in FIGS. 33-36), the rear camming portion 392 of the latch shifts into the lower opening 390 in the lower shaft member, allowing the latch member 337 to pivot so that the post 338 of the latch member shifts upward in order to receive an implant member or release an implant member held by the instrument, as illustrated in FIG. 39. When the central shaft member 326 is in the forward position, the post 338 of the latch member 337 is easily shifted out of the way as an implant portion is received by or removed from the gripping mechanism 316. This allows the implant portion to be lightly held by the latch member 337. However, the upward pivoting of the post 338 of the latch member 337 may also be assisted by a forward camming surface of the latch member. For instance, the lower shaft 328 may be configured so that the hook end 340 at the distal end of the lower opening 390 abuts a forward chamfered surface 393 of the latch member 337, forcing the latch member to pivot.

FIG. 40 shows a cross-sectional view of a disc device inferior member 1000 and superior member 1008 secured to the instrument in a manner similar to that shown in FIGS. 19-21. The flange 348 at the tip of the central shaft member 326 is positioned in an undercut slot 1002 of the inferior implant member 1000. The positioning of the central shaft 326 forces the latch post 338 coupled thereto downward into a hole 1005 defined in the inferior implant member 1000. The lower shaft 328 is positioned so that the hook end 340 thereof abuts an outer edge 1006 of the inferior implant member 1000, and preferably abuts an undercut groove 1007 below the implant outer edge 1006. The profile of the hook end 340 of the lower shaft member may be configured to engage the undercut groove 1007 below the outer edge of the implant in a manner that prevents the inferior implant member 1000 from swiveling with respect to the instrument when sufficient forward force is applied to the lower shaft member, holding the inferior implant member 1000 rigidly to the instrument. An actuator may be supplied to shift the lower shaft member between a bracing configuration, where it applies a significant force against the lower implant member 1000 to brace it against movement, and a free configuration where the lower shaft lightly contacts the lower implant member 1000 or is retracted away therefrom. Releasing the forward force on the lower shaft member 328 then allows the inferior implant member to be steered to the left or right.

Figure 41:
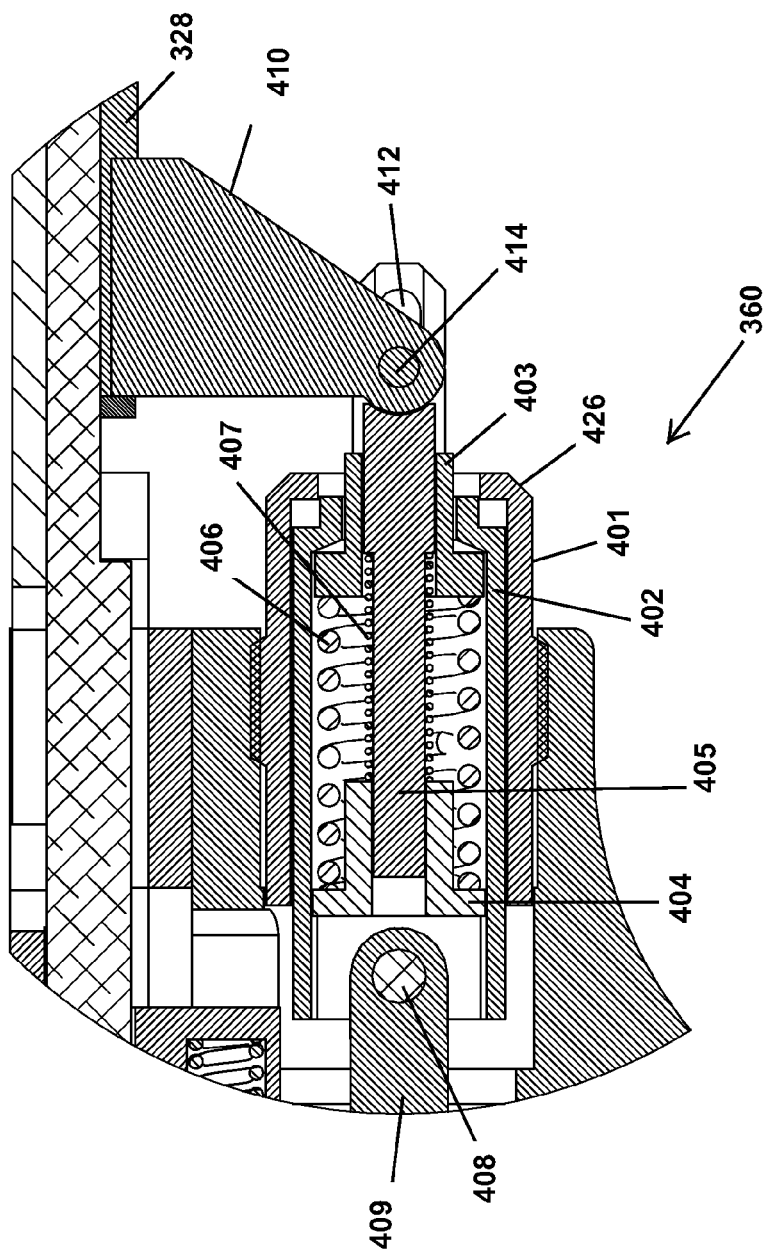
FIG. 41 is a detailed side cross-sectional view of the spring pack of the instrument shown in FIG. 33 that provides a resilient coupling between an actuator and a moveable lower shaft member.
Figure 42:
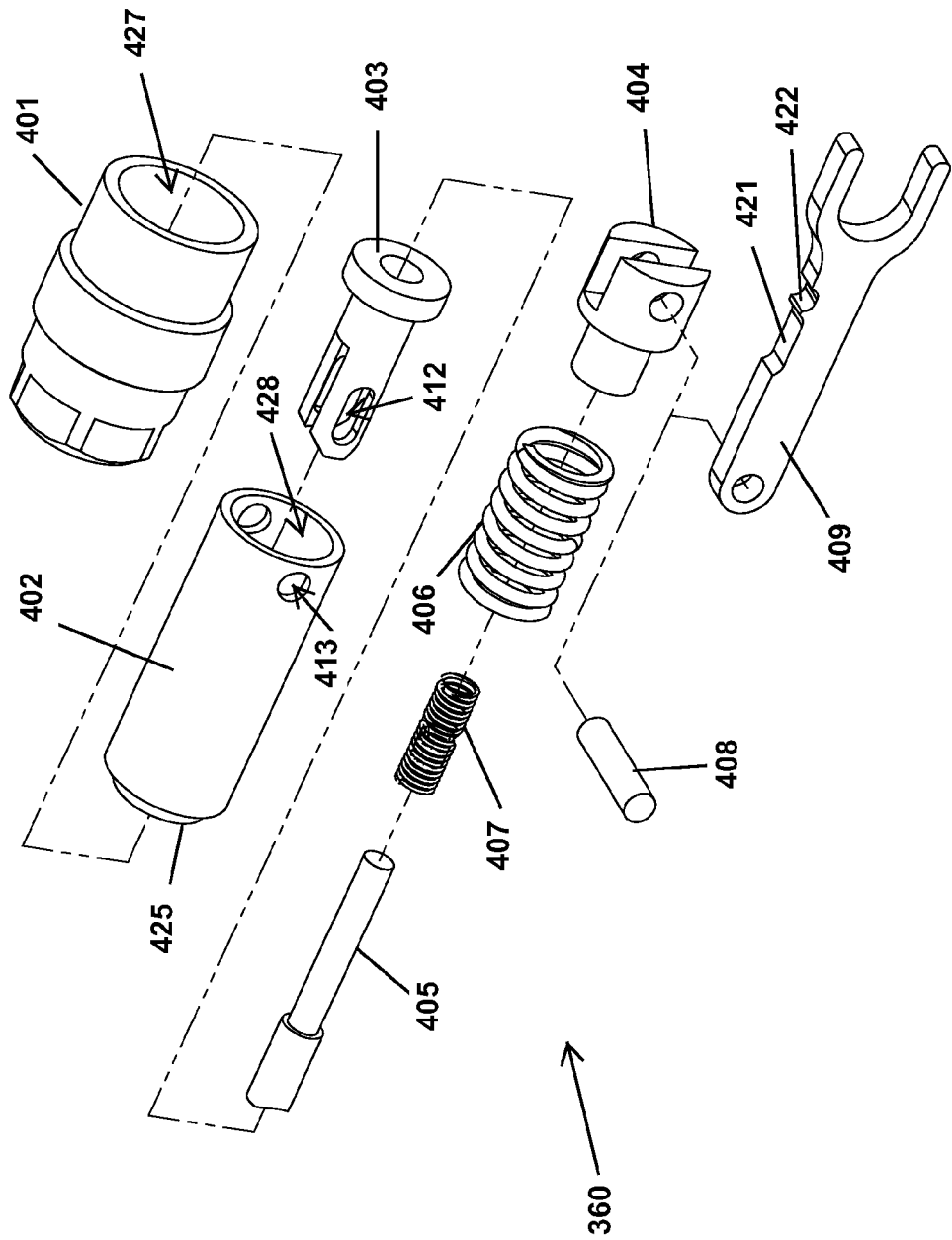
FIG. 42 is an exploded view of the spring pack shown in FIG. 41.
Figure 43:
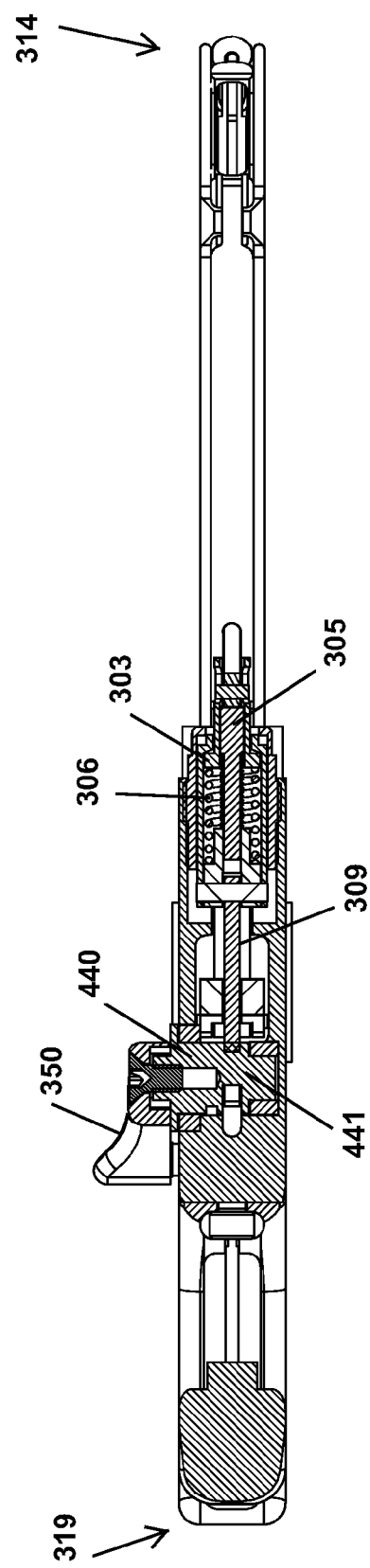
FIG. 43 is a top cross-sectional view of the instrument shown in FIG. 33, showing details of a cam actuator and the spring pack of FIG. 41.

FIGS. 41-43 illustrate details of the spring pack 360, which provides a resilient coupling between the knob actuator 350 and the lower shaft member 328. Although the knob actuator 350 is shown as a crank mechanism with a single arm (FIG. 33), the actuator may have multiple arms or lobes, or may take the form of a dial or other suitable mechanism. If desired, the actuator associated with the lower shaft member may be configured to operate without rotation, such as through a sliding switch mechanism.

The resilient coupling between the knob actuator 350 and the lower shaft member 328 reduces the movement of the lower shaft as the load applied increases, reducing or preventing the application of excessive force on the implant by the lower shaft member 328. When the lower shaft member 328 contacts an implant held by the instrument's gripping mechanism, springs contained in the spring pack 360 begin to compress so that forward travel of the lower shaft member 328 is reduced even as the actuator continues to move. The spring pack 360 also can automatically account for tolerances in the machining of the parts associated with movement of the lower shaft member 328, and the springs of the spring pack compress when too great a load is applied or when the actuator 350 is shifted too far in a forward direction.

The spring pack 360 includes an exterior housing 401 having a bore 427 in which a hollow barrel 402 is slidably disposed. The barrel includes an axial bore 428 in which a spring base 404, inner plunger 405, outer plunger 403, outer coil spring 406, and inner coil spring 407 are disposed. The spring pack 360 is coupled to a lower extension 410 that connects the spring pack to the lower shaft member 328. The spring base 404 is linked to the barrel 402 by a pin 408, which also serves to couple the spring base 404 to an arm or drive fork 409 that is coupled to the knob actuator 350 of FIG. 33. Operation of the knob actuator 350 rotates a cam cylinder that shifts the drive fork 409 back and forth. Shifting the drive fork 409 simultaneously shifts the barrel 402 and spring base 404. The outer plunger 403 and inner plunger 405 are also shifted forward by the drive fork 409 due to the outer coil spring 406 and inner coil spring 407, respectively, disposed within the barrel 402 between the spring base 404 and the plunger members. Forward movement of the barrel 402 is limited by the end wall 426 of the spring pack housing 401, but movement of the lower shaft member 328 may be limited before maximum forward travel of the barrel 402 due to the resilient coupling created by the outer spring member 406 and inner spring member 407, as further explained below.

The outer plunger 403 includes an elongate opening 413 that receives a pin 411 through the lower extension 410. The elongate opening 413 permits a small amount of travel of the outer plunger 403 without travel of the lower shaft member 328. The outer spring member 406 biases the outer plunger 403 in the forward direction, and positions the outer plunger 403 at the front end of the barrel 402 when the spring pack is not under a significant load. The inner plunger 405 is similarly biased forward by the inner spring 407, exerting a forwardly directed force upon the lower extension 410 that couples the lower shaft member 328 to the spring pack 360.

The forward force of the inner plunger 405 biases the lower extension 410 and the pin 411 coupling the outer plunger 403 thereto toward the front end of the elongate opening 412 of the outer plunger 403. Feedback on the lower shaft member 328 will gradually increase as it is shifted forward, eventually exerting sufficient rearward force to begin compressing the relatively weak inner spring 407, allowing the pin 411 securing the lower extension 410 to slide gradually toward the rear end of the elongate opening 412 of the outer plunger 403. When the pin 411 abuts the rear end of the elongate slot 412, the force of the large outer spring 406 that biases the outer plunger 403 forward applies a forwardly directed force on the lower extension 410 for shifting the lower shaft member 328 forward. Eventually, the force exerted by the outer spring member 406 may be overcome by feedback on the lower shaft member 328, causing compression of the outer spring member 406 to gradually reduce the travel of the lower shaft member 328 despite forward motion of the drive fork 409 and spring base 404.

Figure 44:
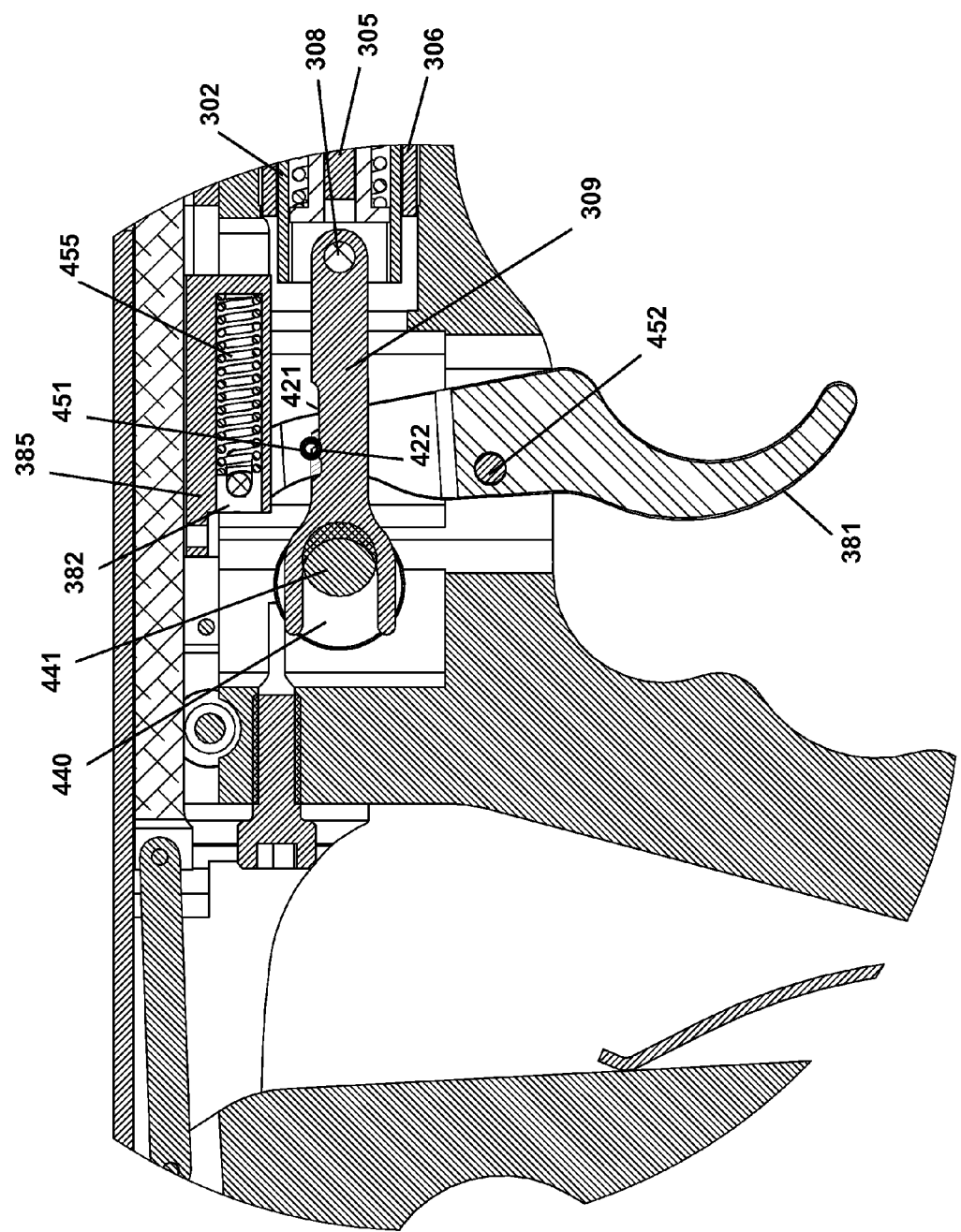
FIG. 44 is a detailed cross-sectional view of a steering mechanism of the instrument shown in FIG. 33.

Details of the coupling between the knob actuator 350 and the drive fork 409 are shown in FIGS. 43 and 44. The knob actuator 350 is fastened to an asymmetrical cam drum 440 having a cylindrical offset cam portion 441 sized to be disposed in the open end of the drive fork 309. The cam drum is held in place in the housing with bushings 442 and 443 (FIG. 36). Rotation of the cam drum 440 shifts the offset cam portion 441 in an arc, and the coupling between the offset cam portion 441 and the drive fork 309 converts the arcuate travel of the offset cam portion 441 to reciprocating motion of the spring base 404 pivotably linked to the drive fork 309. When the actuator 350 and cam drum 440 are rotated so that the offset cam portion 441 is positioned forward (toward the distal end 314 of the instrument), the drive fork 309 is pushed forward and applies a forwardly directed force upon the lower shaft member 328 through both the outer spring 406 and inner spring 407 so that the lower shaft member 328 is in a bracing configuration and braces against the implant member secured by the central shaft. Rotation of the offset cam portion 441 rearward (toward the proximal end 319 of the instrument) releases the force exerted on the lower shaft member 328 by the larger outer spring 406, so that the lower shaft member 328 is in a free configuration wherein only the inner spring 407 biases the lower shaft member 328 into light contact with the implant member.

FIG. 44 also shows additional detail of the mechanism used to steer an implant secured to the instrument, including the trigger lever 381 coupled to the steering block 385. The trigger lever 381 pivots about a trigger pin 452, which pivots the upper portion 382 of the trigger lever forward. A trigger spring 455 provides a resilient coupling between the trigger lever 381 and steering block 385, causing forward shifting of the trigger block 385 upon pulling the trigger but reducing the travel of the steering block 385 when significant resistance is encountered in order to limit the force applied by the steering block to the implant secured by the instrument. This resilient coupling provides similar advantages to the spring pack 360 described above.

The instrument also may include a locking feature that prevents manipulation of the trigger lever 381 when the lower shaft member is braced against an implant. For instance, when the drive fork 309 coupled to the spring pack 360 is in an advanced position, so that the lower shaft member 328 is pushed forward to prevent steering of the implant, the trigger mechanism for the steering block may be locked in place by components linked to the lower shaft actuator. In the illustrated instrument, a locking pin 451 on the trigger is positioned in a locking recess 422 of the drive arm 309 when the drive arm is in the forward position, as shown in FIG. 44, but rotation of the cam drum 440 swings the drive arm 309 downward and then rearward so that the locking pin 451 is positioned in a much longer steering recess 421 of the drive arm 309 that allows movement of the trigger lever 381 to operate the steering block 385.

Figure 45:
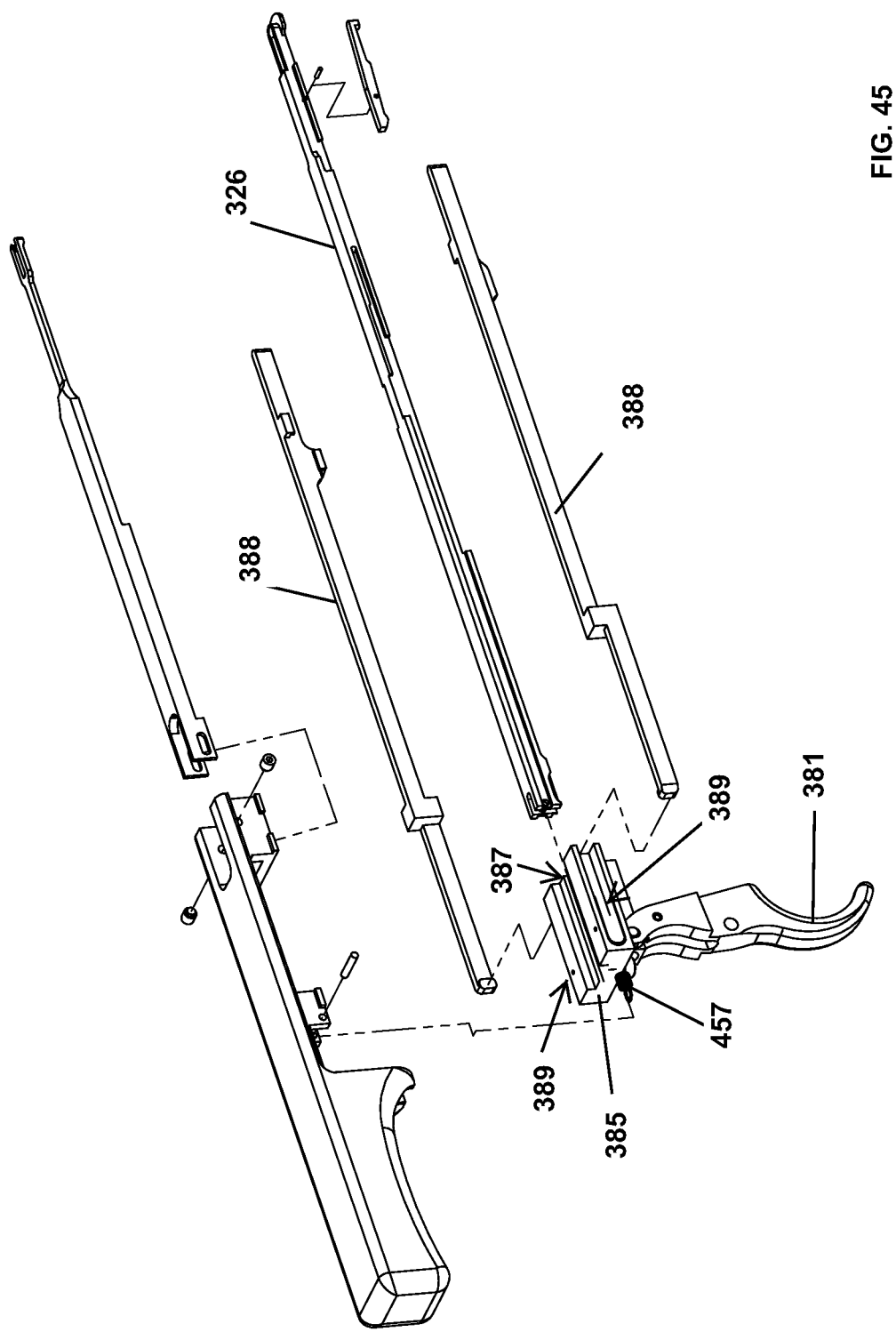
FIGS. 45 and 46 are exploded views of the steering mechanism shown in FIG. 44 and used to steer an implant to the left or right while the implant is mounted to the instrument.

The steering block 385 and associated components are shown in a perspective view in FIG. 45. The steering block couples the trigger lever 381 to a steering shaft 388 to steer than implant. A steering shaft 388 may be positioned in one of the two lateral slots 389 on either side of the steering block, depending on whether the user wishes to steer the implant to the left or right. A steering shaft may be permanently mounted to the steering block 385 if desired, but releasably coupling the steering shafts 388 to the instrument allows the user to select an approach from either side of the posterior spine. A guide slot 387 along the center of the steering block 385 permits the central shaft member 326 to pass therethrough, so that the central shaft member 326 and steering block 385 each may be shifted back and forth without movement of the other. A return spring 457 couples the steering block 385 to the instrument body and biases the steering block 385 slightly rearward so that release of the trigger lever 381 returns the steering block 385 to its initial rearward position, retracting any steering shaft 388 coupled thereto and pivoting the lower portion of the trigger lever 381 forward to its initial position.

Figure 46:
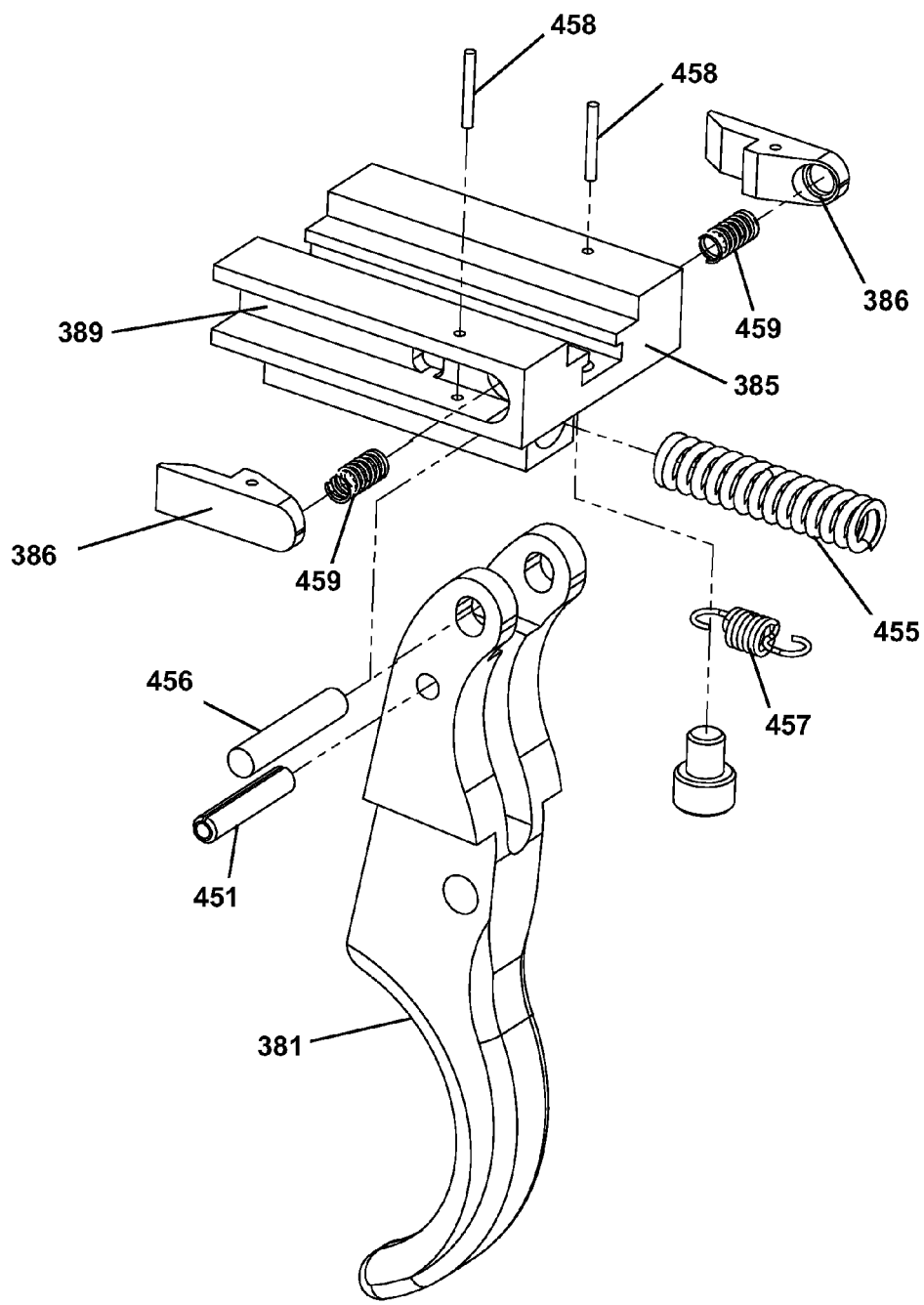

Further detail of the steering block 385 is shown in the exploded view of FIG. 46. Clip members 386 are positioned in the lateral slots 389 of the steering block and secured pivotably thereto with pins 458. Springs 459 bias the clip members 386 into a clamping orientation so that a steering shaft 388 may be easily inserted into the slots and clamped in place and then later removed without undue manipulation of parts. As previously described, pulling the trigger lever 381 pivots an upper end thereof forward to push a spring 455 associated with the steering block 385 forward, advancing the steering block through a resilient connection. A pin 456 or other structure associated with the trigger lever 381 may exert force on the spring 455. A return spring 457 returns the steering block 385 and trigger lever 381 to their original positions by pulling the steering block 385 rearward when the trigger lever 381 is released.

Figure 47:
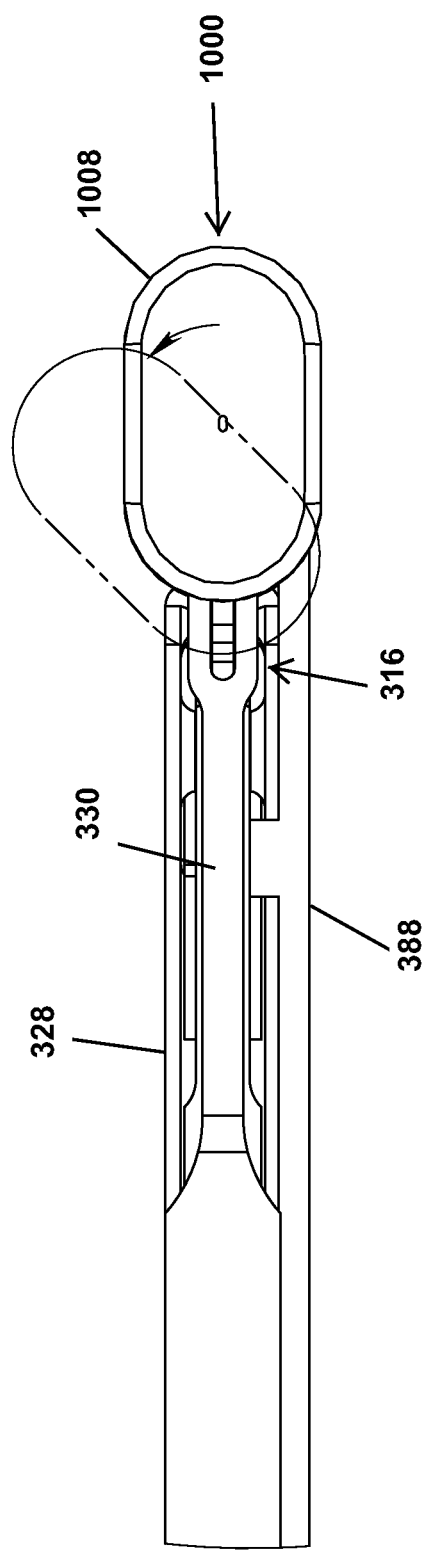
FIG. 47 illustrates the pivoting or steering of an implant using the steering mechanism shown in FIGS. 44-46.
Figure 48A:
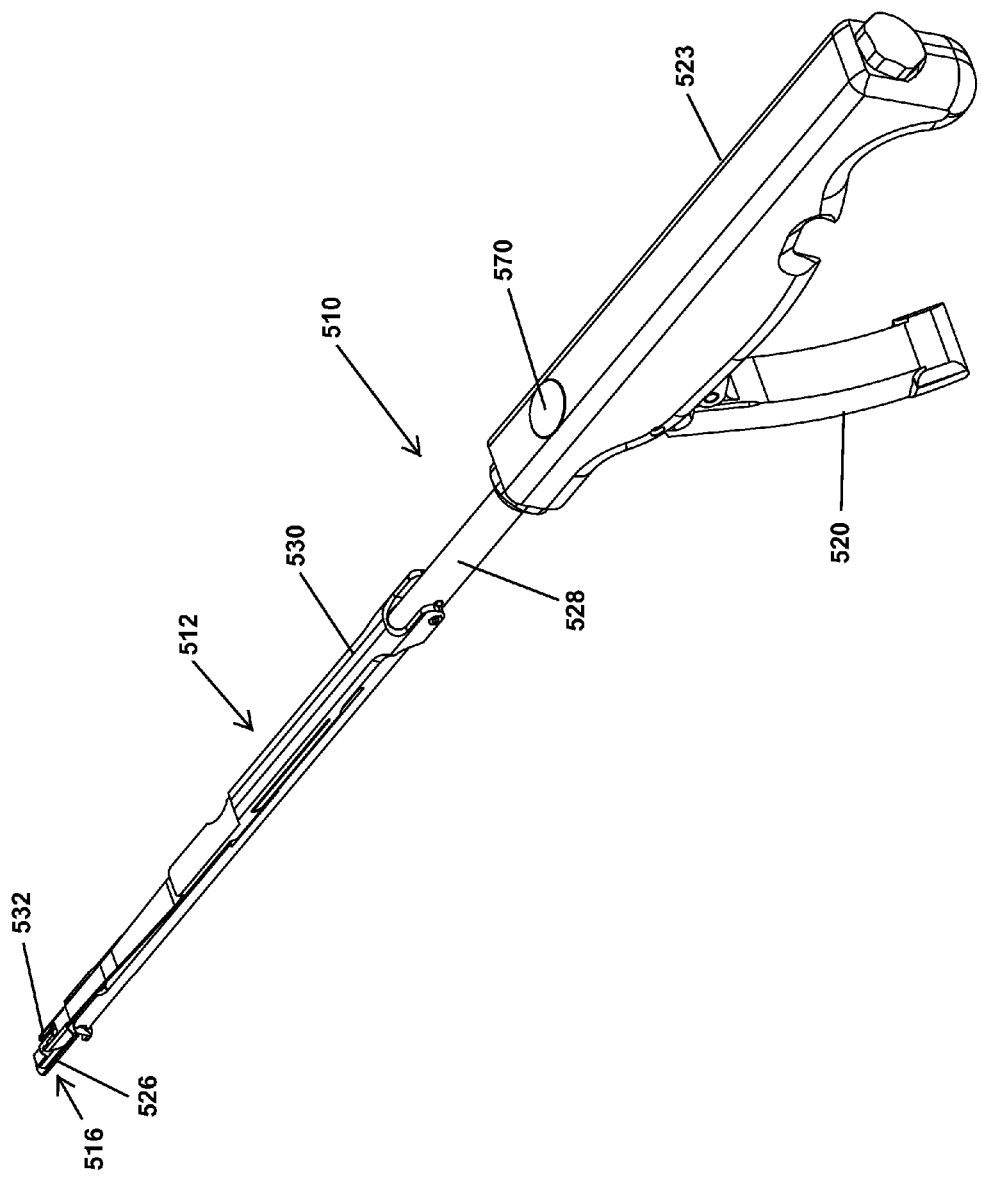
FIGS. 48A and 48B are perspective views of another instrument according to the invention described herein.
Figure 48B:
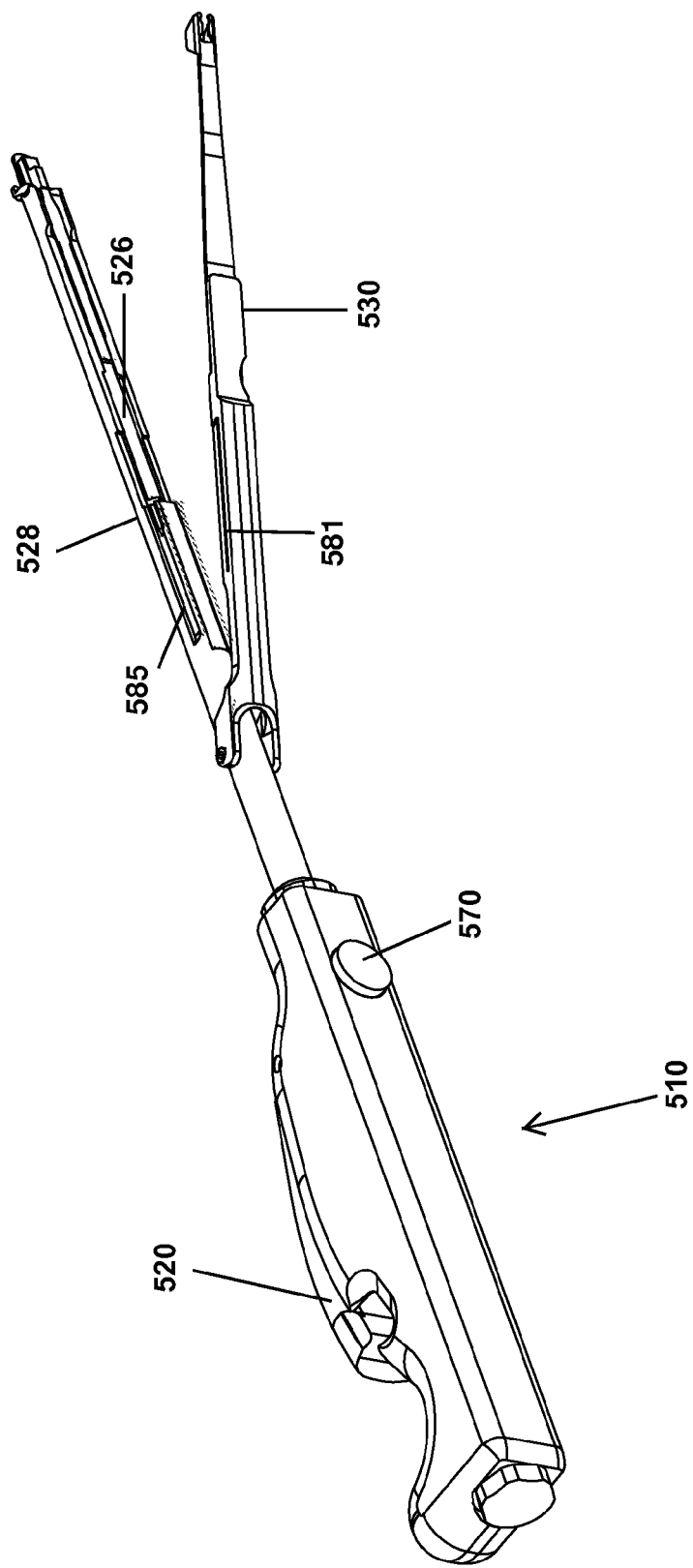

FIG. 47 illustrates the steering of an implant by forward advancement of a steering shaft 388 coupled to one side of the instrument. By abutting one side of the implant with a steering shaft 388 positioned alongside the gripping mechanism 316, the implant is directed toward the side opposite the steering shaft 388. The steering shaft may be configured to pivot the implant a desired amount. Although the user will usually wish to pivot the implant so that its length is aligned in a lateral direction, pivoting the implant only partway (for instance, about 20 degrees) will ordinarily suffice because beginning the steering process allows the anatomy of the body to continue to align the implant as it is inserted.

A separate insertion instrument 510 for inserting a disc device is shown in FIGS. 48-53. The instrument 510 has an elongate shaft assembly 512 that functions in a similar manner to the shaft assembly 312 of the instrument 310 in FIG. 33. As shown in the perspective view of FIG. 48A, the elongate shaft assembly 512 includes a main or central shaft member 526 that forms a gripping mechanism 516 for gripping an inferior implant member, an outer shaft member 528 that partially encloses the central shaft member 526, and an upper shaft member 530 pivotably coupled to the outer shaft member 528 for gripping a superior implant member. FIG. 48B shows the upper shaft member 530 pivoted upward to an open position. The insertion instrument 510 has a simplified manner of operation, and is best suited for use in a lateral approach of the annulus.

Figure 49:
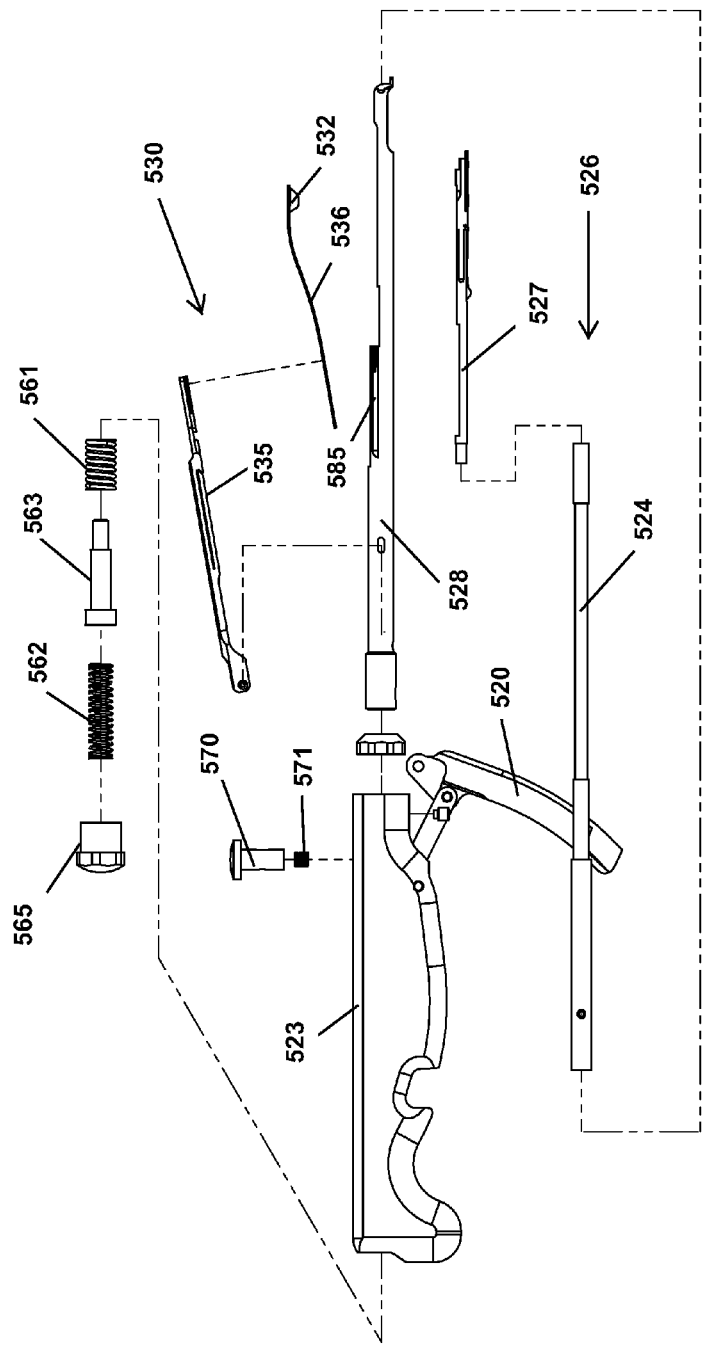
FIG. 49 is an exploded view of the instrument in FIG. 48.
Figure 50A:
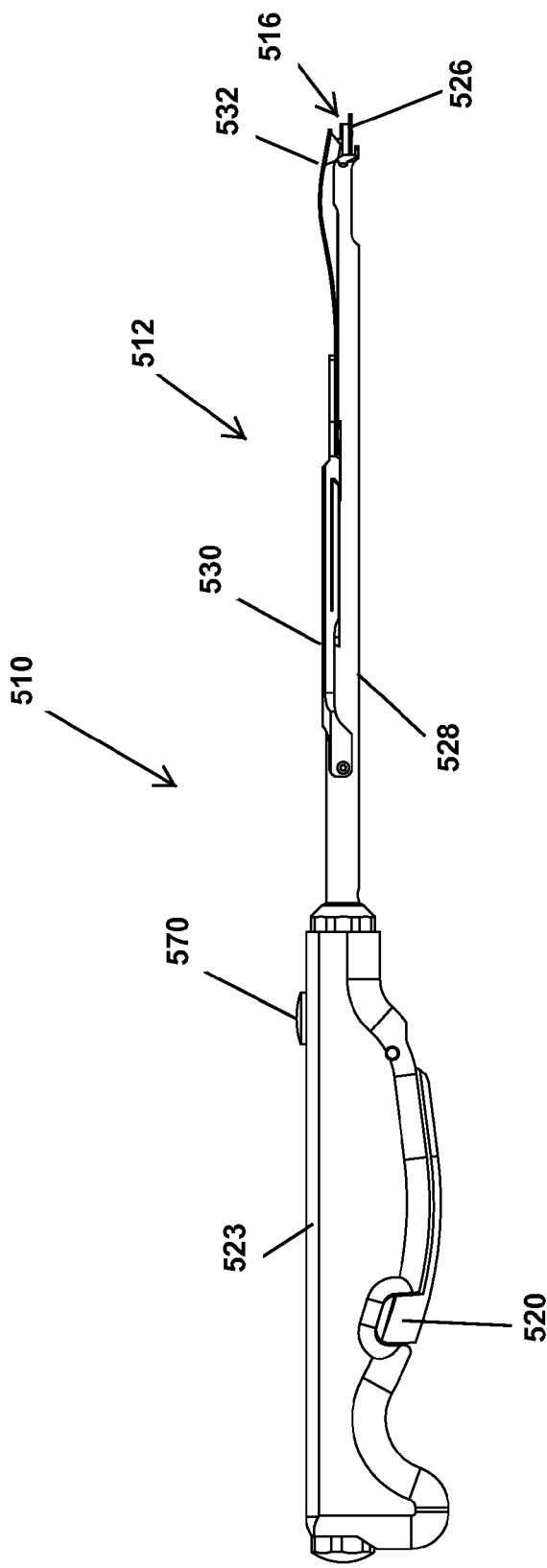
FIGS. 50A and 50B are side views of the instrument in FIG. 48.
Figure 50B:
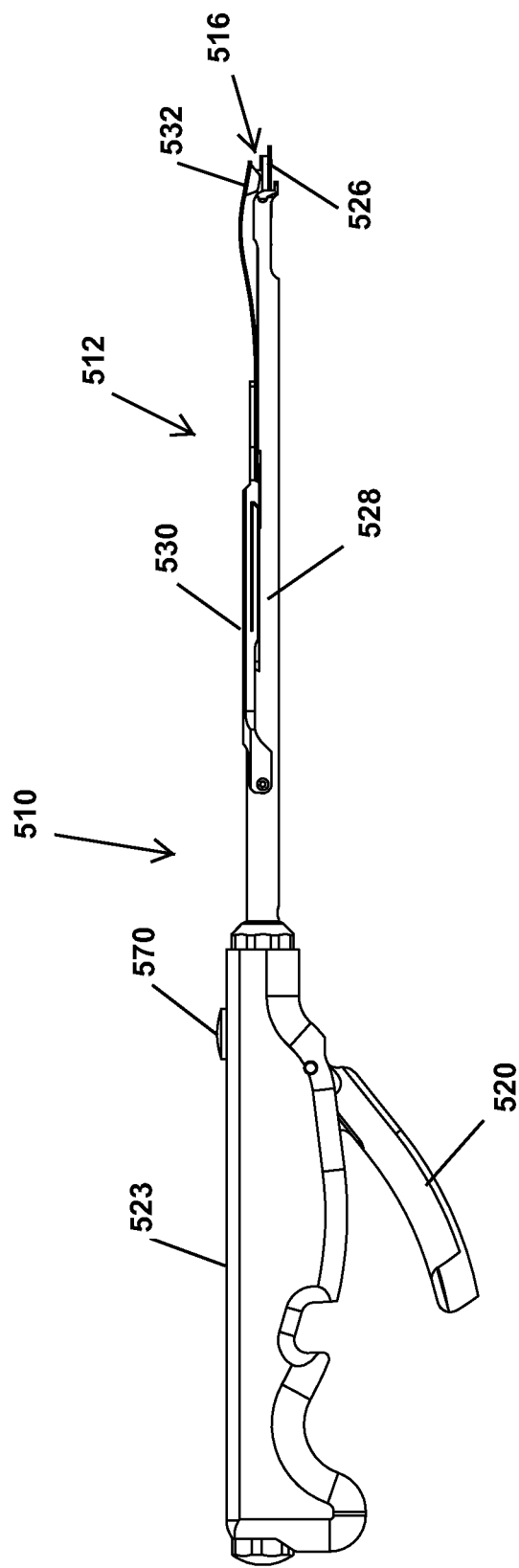
Figure 51A:
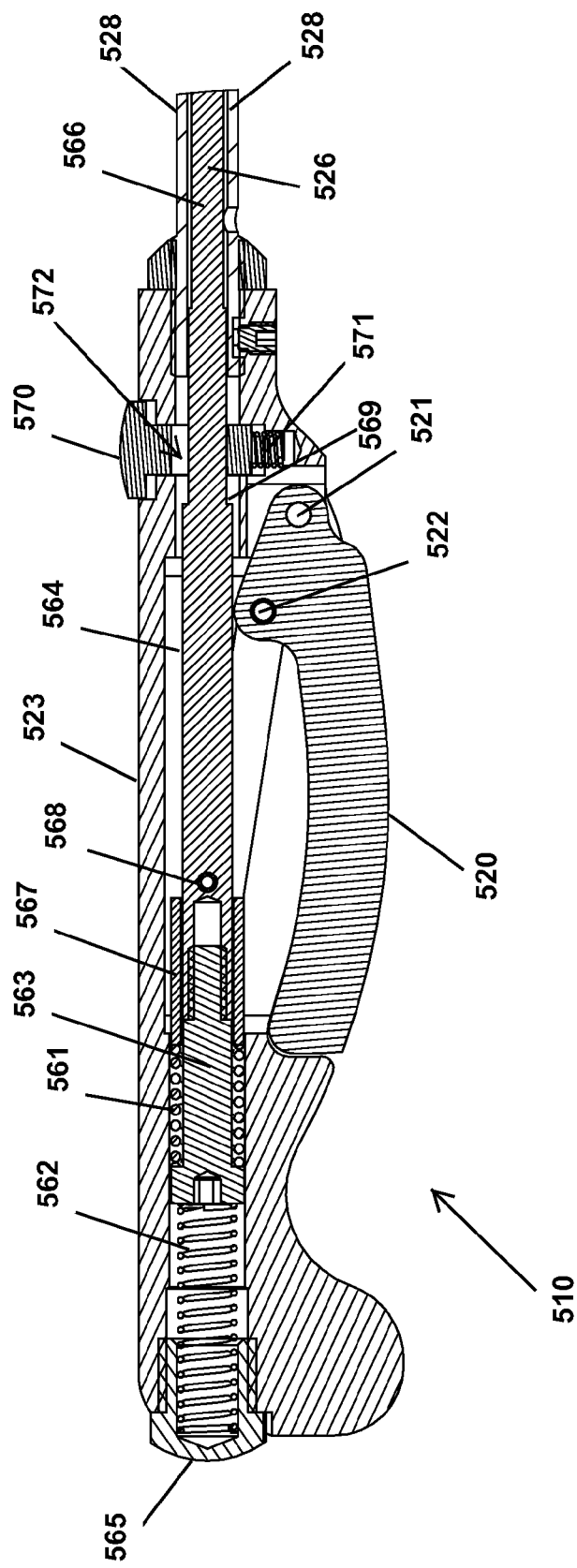
FIGS. 51A-C are sequential side cross-sectional views illustrating the manipulation of an actuator to shift the central shaft member forward to receive or release an implant.
Figure 51B:
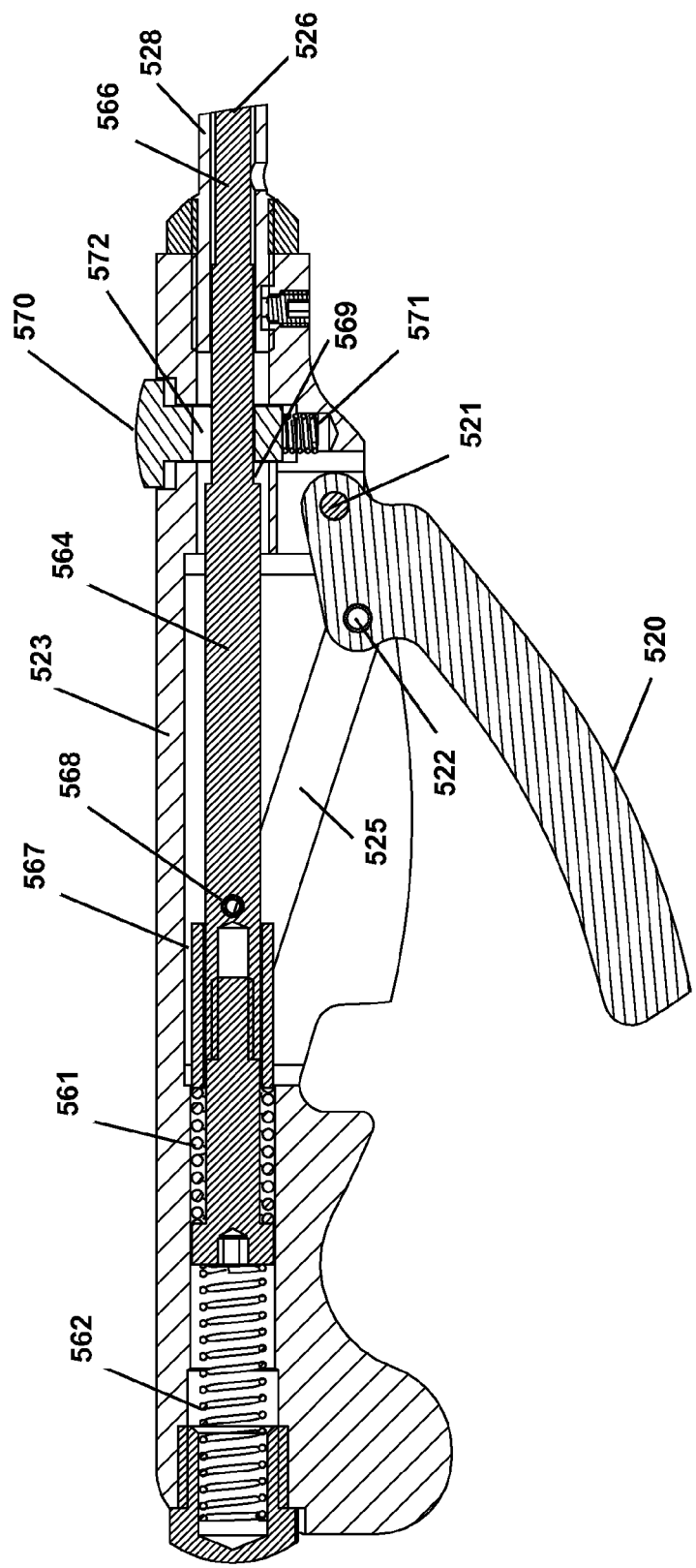
Figure 51C:
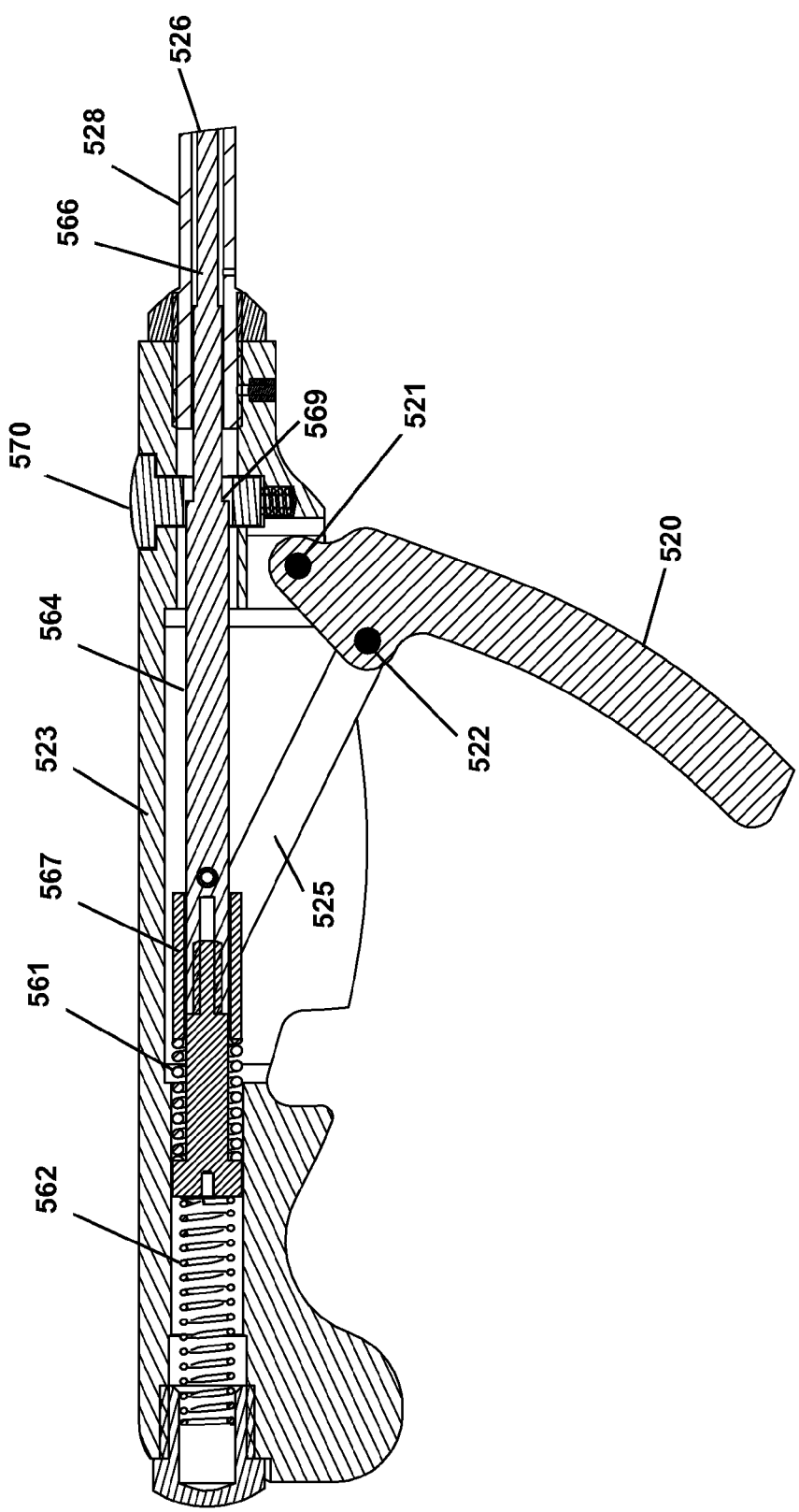

An exploded view of the instrument is shown in FIG. 49. The central shaft member 526 includes an elongate neck 524 assembled with a head portion 527 and slidably disposed in the outer shaft member 528 and body or handle portion 523. A button 570 crosses the path of the central shaft member 526 through the body. Springs 561 and 562 are disposed in the handle 523 to act on the central shaft member 526, and an end cap 565 closes the rear of the handle. The upper shaft member 523 has a rigid portion 535 and a flexible portion 536 with a grasping claw 532 that is mounted to the rigid portion 535.

The instrument 510 captures and releases an implant member when an actuator lever 520 is pivoted relative to the instrument body 523. The actuator lever 520 is shown in the closed position in FIGS. 50A and 51A. In this position, an implant is held tightly to the instrument for insertion into the patient. Pivoting the actuator lever 520 outward as in FIGS. 50B, 51B, and 51C shifts the central shaft member 526 forward relative to the outer shaft 528 to release the implant or allow an implant to be coupled to the central shaft member 526. The central shaft member 526 and outer shaft member 528 operate in essentially the same manner as the central shaft member 326 and lower shaft member 328, respectively, of the instrument 310 in FIGS. 38-40, except that the outer shaft member 528 is completely stationary so that retracting the central shaft member 526 pulls an inferior implant member secured thereto tightly against the hook end 540 of the outer shaft member 528 without separate manipulation of the outer shaft member. As a result, the outer shaft member 528 cannot be disengaged to allow steering of the implant. However, if desired, an additional actuator for control of the outer shaft member 528 may be provided in order to allow for shifting of the outer member and steering of the implant.

The actuator lever 520 shifts a pivot link 525 that is pivotably coupled between the actuator lever 520 and an actuator sleeve 567 that surrounds a portion of the central shaft member 526. The actuator sleeve 567 is coupled to the central shaft member 526 by a drive pin 568 or similar structure and a resilient member (such as the coil spring 561) which hold the sleeve 567 therebetween. When the actuator lever 520 is pulled outward so that it pivots away from the instrument body 523, the pivot link 525 pulls the actuator sleeve 567 forward so that it pushes against the drive pin 568 and advances the central shaft member 526, activating a latch of the central shaft member 526 as further described below in order to grip an implant.

In the illustrated form, the instrument 510 has a motion limiter in the form of a button 570 that selectively prevents the central shaft member 526 from moving forward once it has reached the implant release position. Forward travel of the central shaft member 526 is limited by abutment between a shoulder portion 569 of the central shaft member 526 and a button 570 through which the central shaft member 526 must pass. The button 570 is biased upward by a spring 571 so that the opening 572 through the button 570 is aligned so as to allow passage for a narrower portion 566 of the central shaft member 526 but to prevent passage of a wider portion 564 of the central shaft. Pushing downward on the button 570 as in FIG. 51C permits passage of the wider portion 564 of the central shaft, allowing for release of the upper shaft 530 as further discussed below.

Pivoting the actuator lever 520 toward the instrument body 523 shifts the actuator sleeve 567 rearward, exerting a force against the coil spring 561 disposed about the central shaft, which in turn exerts a force against a shoulder bolt 563 connected to the back end of the central shaft member 526. The coil spring 561 provides a resilient coupling between the actuator and the moveable central shaft 526, preventing the user from exceeding a predetermined level of force in securing the implant, similar to the spring pack 360 of the previous instrument 310 described in connection with FIGS. 41-43. In this case, pivoting the actuator lever 520 toward the instrument body 523 causes rearward shifting of the central shaft member 526 to retract the central shaft and secure an implant member against the outer shaft 528. If the force required to engage the implant with the outer shaft member 528 is too great, the coil spring 51 will begin to compress, reducing the amount that the central shaft member travels as the actuator lever 520 pivots. This not only provides a limit to the force exerted against the implant, but also accounts for variations in parts caused by machining tolerances.

An additional spring 562 may be provided to bias the central shaft member 526 slightly forward in order to hold the actuator lever 520 in either an open or closed position. Without some forward bias of the central shaft 526, the actuator lever 520 will pivot freely whenever not held in place by the surgeon. The presence of the spring 562 holds the actuator 520 in the closed position of FIG. 51A whenever the actuator is pivoted far enough inward that the pivot link 525 moves past its center position.

Figure 52:
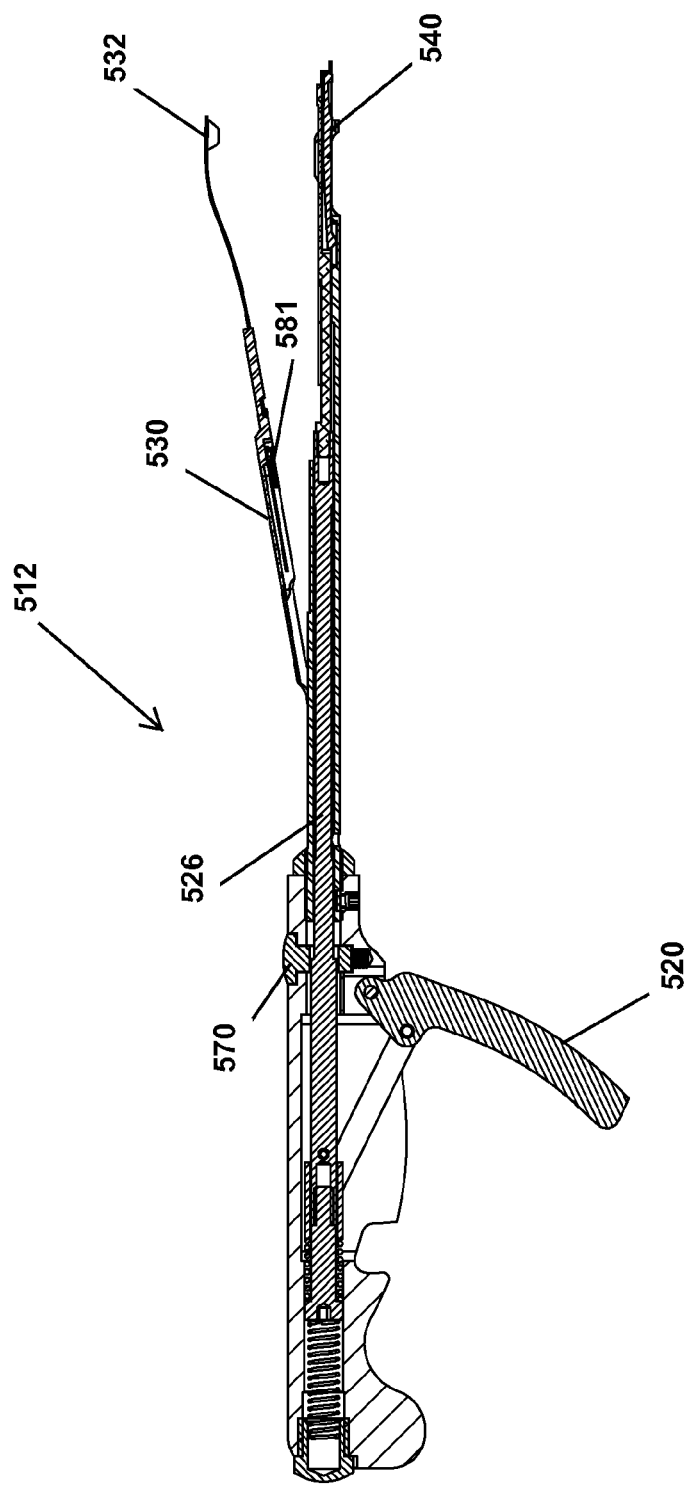
FIG. 52 is a side cross-sectional view of the instrument shown in FIG. 48 with the upper shaft member pivoted to an open position.
Figure 53:
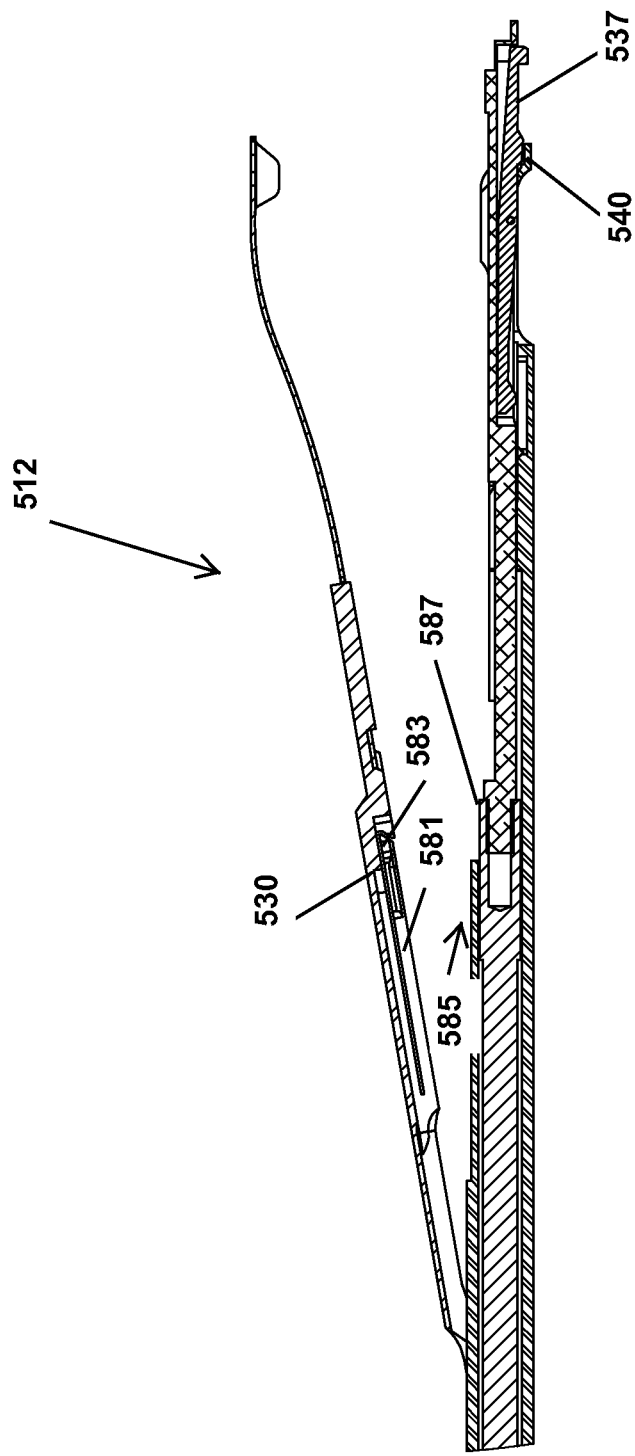
FIG. 53 is a detailed side cross-sectional view of the shaft assembly of the instrument shown in FIG. 53.
Figure 54:
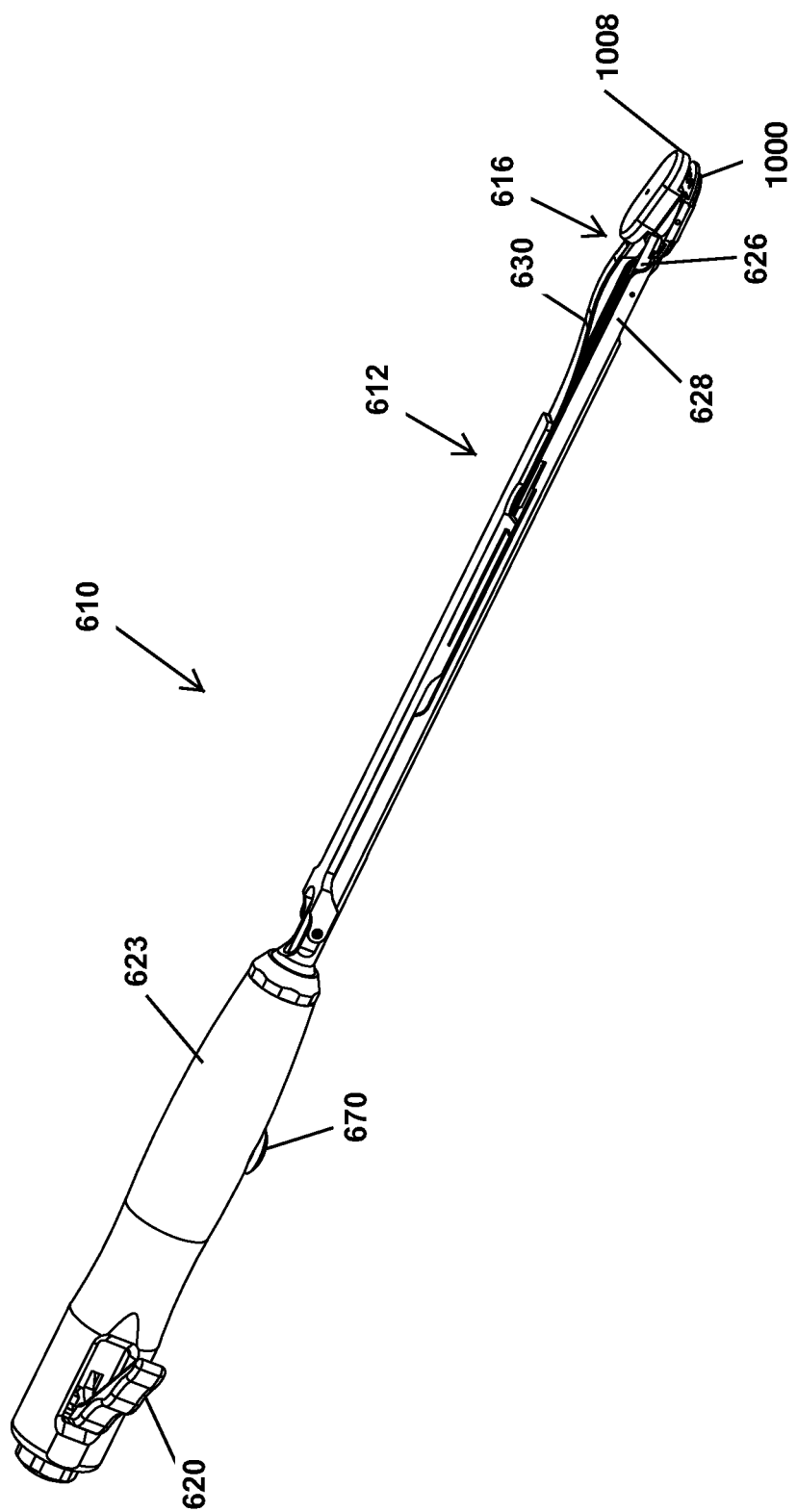
FIG. 54 is a perspective view of another instrument according to the invention described herein.

FIGS. 52 and 53 show additional detail of the shaft assembly 512, including the pivotability of the upper shaft member 530 away from the central shaft 526 and outer shaft 528 when the central shaft is shifted forward. The central shaft 526, outer shaft 528, and upper shaft 530 of the illustrated instrument are configured to secure an implant in the same manner described in connection with FIGS. 38-40, including the pivoting of a latch member 537 as the central shaft member 526 is shifted back and forth.

Release of the upper shaft member 530 to allow pivoting thereof is also controlled by shifting of the central shaft member 526. The sides of the upper shaft member 530 are equipped with flexible tabs 581 with inwardly directed flanges 583 that ride in lateral grooves 585 of the outer shaft member 528 (see FIGS. 48B and 49). Forward travel of the central shaft member 526 causes an enlarged shoulder portion 587 thereof to contact the inwardly directed flanges 583 of the upper shaft member 530, splaying the resilient tabs 581 of the upper shaft member outward to release them from the grooves 585 of the outer shaft member 528 (as shown in FIG. 53). Forcing the upper shaft member 530 downward when the central shaft member 526 is retracted snaps the flanges 583 back into the slots 585 of the outer shaft member 528, re-coupling the upper shaft member 530 with the rest of the elongate shaft assembly 512.

Figure 55:
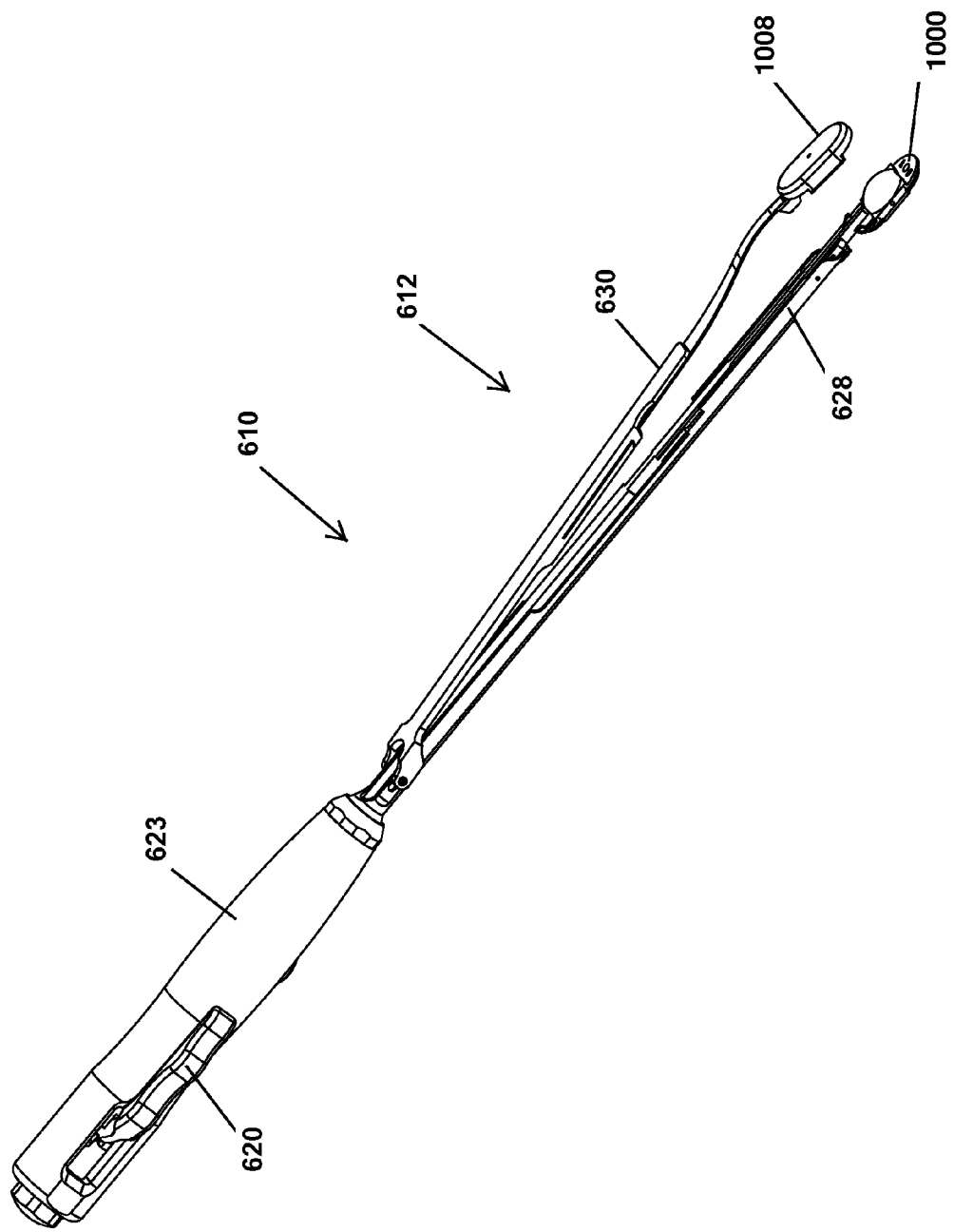
FIG. 55 is a perspective view of the instrument shown in FIG. 54 with the upper shaft member pivoted to an open position.

Another example of an insertion instrument 610 is shown in FIGS. 54-62. The instrument 610 has an elongate shaft assembly 612 that functions in a similar manner to the shaft assembly 312 of the instrument 310 in FIG. 33 and the shaft assembly 512 of the instrument 510 in FIGS. 52 and 53. As shown in the perspective view of FIG. 54, the elongate shaft assembly 612 includes a main or central shaft member 626 that forms a gripping mechanism 616 for gripping an inferior implant member, an outer shaft member 628 that partially encloses the central shaft member 626, and an upper shaft member 630 pivotably coupled to the outer shaft member 628 for gripping a superior implant member. FIG. 55 shows the upper shaft member 630 pivoted upward. The insertion instrument 610 has a simplified manner of operation, and is best suited for use in a lateral approach of the annulus.

Figure 56:
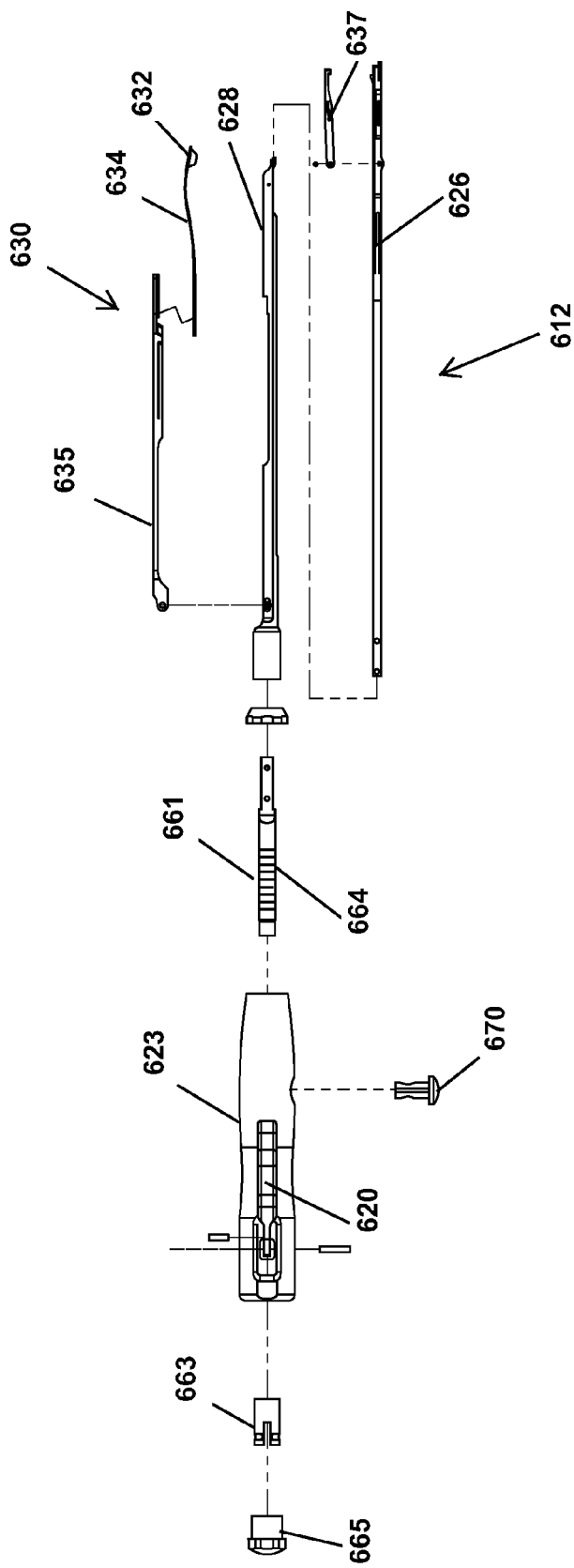
FIG. 56 is an exploded view of the instrument shown in FIG. 54.

The components of the instrument 610 are shown disassembled in the exploded view of FIG. 56. A moveable latch member 637 is pivotably disposed in the central shaft member 626, and the central shaft member is slidably disposed in the outer shaft member 628. The upper shaft member 630 is pivotably mounted to the outer shaft member 628 and includes a rigid portion, a flexible portion 634, and a grasping claw 632. The elongate shaft assembly 612 is mounted to the body portion 623 of the instrument 610, and the central shaft member 626 is coupled to a pivoting actuator 620 through a linkage or drive shaft 664 that has a coil spring 661 disposed thereabout and a trigger mount 663 coupled to the drive shaft. An end cap 665 covers the end of the body member 623.

Figure 57:
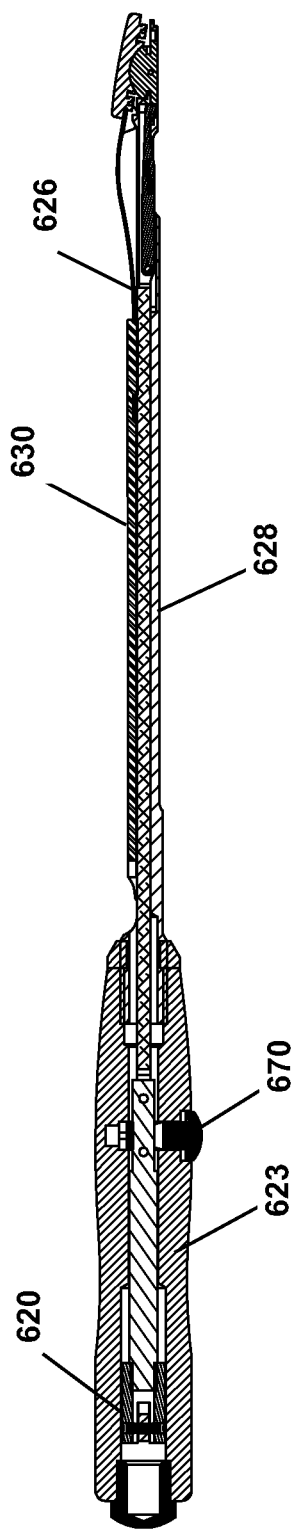
FIG. 57 is a side cross-sectional view of the instrument shown in FIG. 54.
Figure 58:
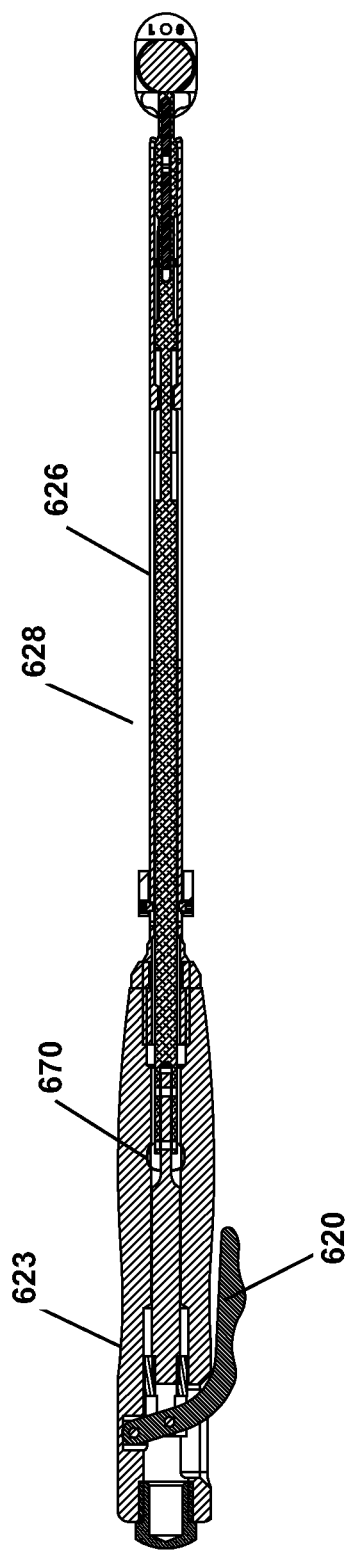
FIG. 58 is a top cross-sectional view of the instrument shown in FIG. 54.

The instrument 610 is shown from a side cross-sectional view in FIG. 57 and from a top cross-sectional view in FIG. 58, showing the relationship of the various parts in the assembled instrument. Similar to the previously described instrument 510 of FIG. 51, the instrument 610 captures and releases an inferior implant member when the actuator lever 620 is pivoted relative to the instrument body 623. In the illustrated embodiment of FIGS. 57-58, however, the actuator lever 620 is pivoted toward the instrument body 623 to advance the central shaft 626, and a motion limiter in the form of a button 670 is positioned transverse to the trigger 620 and selectively limits the action of the trigger.

Figure 59:
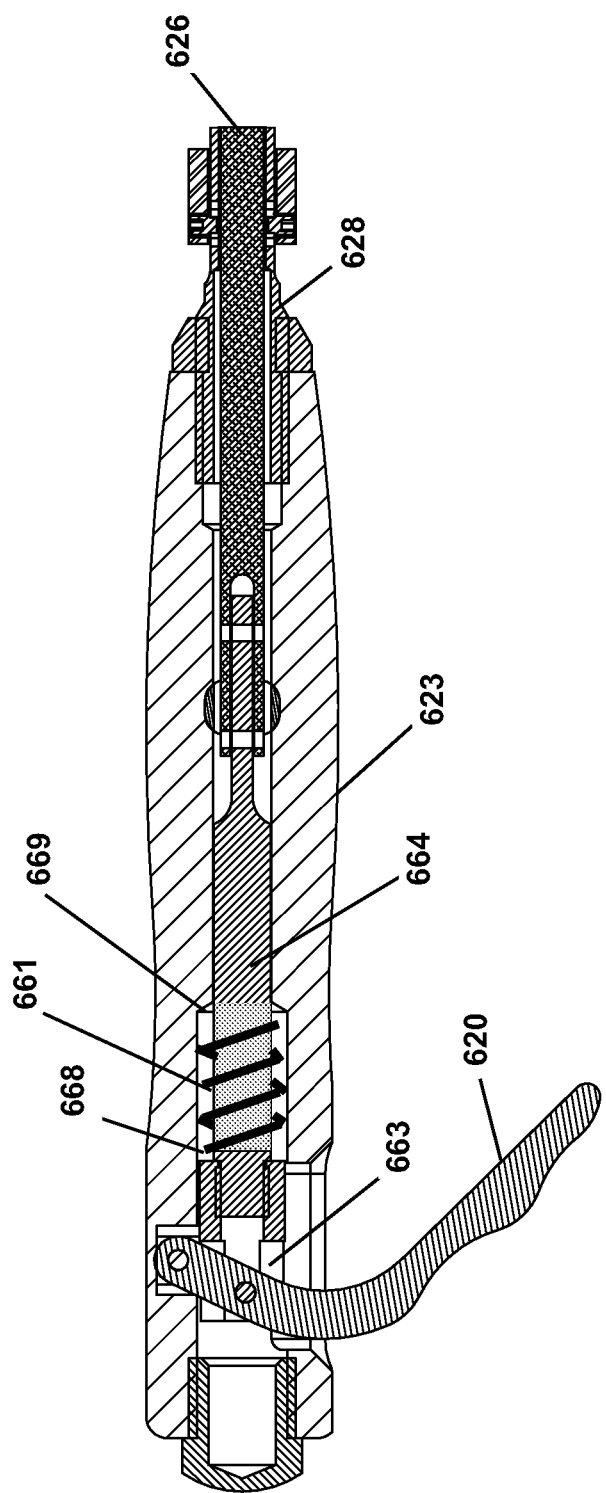
FIG. 59 is a detailed cross-sectional view of the actuator and instrument body of the instrument shown in FIG. 54 with the actuator released.
Figure 60:
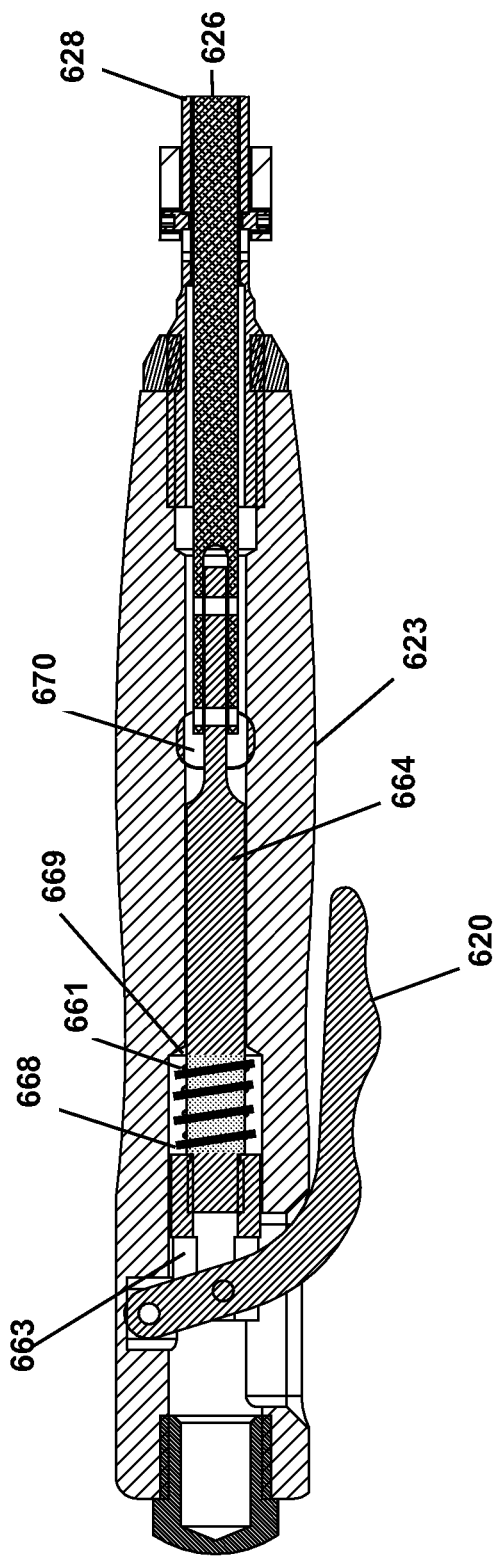
FIG. 60 is a detailed cross-sectional view of the actuator and instrument body of the instrument shown in FIG. 54 with the actuator pivoted to shift the central shaft member forward.

The actuator lever 620 is shown in an initial position in FIG. 59. When the instrument is in this position, with the trigger 620 released, the central shaft 626 is retracted in order to hold an implant against the instrument. Pivoting the actuator lever 620 toward the instrument body 623 as in FIG. 60 shifts the central shaft member 626 forward relative to the outer shaft 628 to release tan implant or allow an implant to be coupled to the central shaft member 626. The central shaft member 626 and outer shaft member 628 operate in essentially the same manner as the central shaft member 526 and outer shaft member 528, respectively, of the instrument 510 in FIGS. 52-53, as discussed above.

The actuator lever 620 is coupled to the central shaft member 526 by a trigger mount 663 that is coaxially connected to an elongate drive shaft 664 that is in turn coupled to the central shaft member 626. A coil spring is located in an interior pocket 668 of the instrument body 623 and surrounds a portion of the drive shaft 664. The trigger mount 663 is wider than the drive shaft 664, and therefore advancement of the trigger mount 663 when pivoting the trigger lever compresses the spring 669 against the far wall 669 of the pocket 668. Upon release of the trigger lever 620, the spring 661 forces the trigger mount 663 backward, returning the central shaft 626 and the trigger lever 620 back to their initial positions. The coil spring 661 is preloaded to exert a set amount of force to hold the implant in place.

Figure 61:
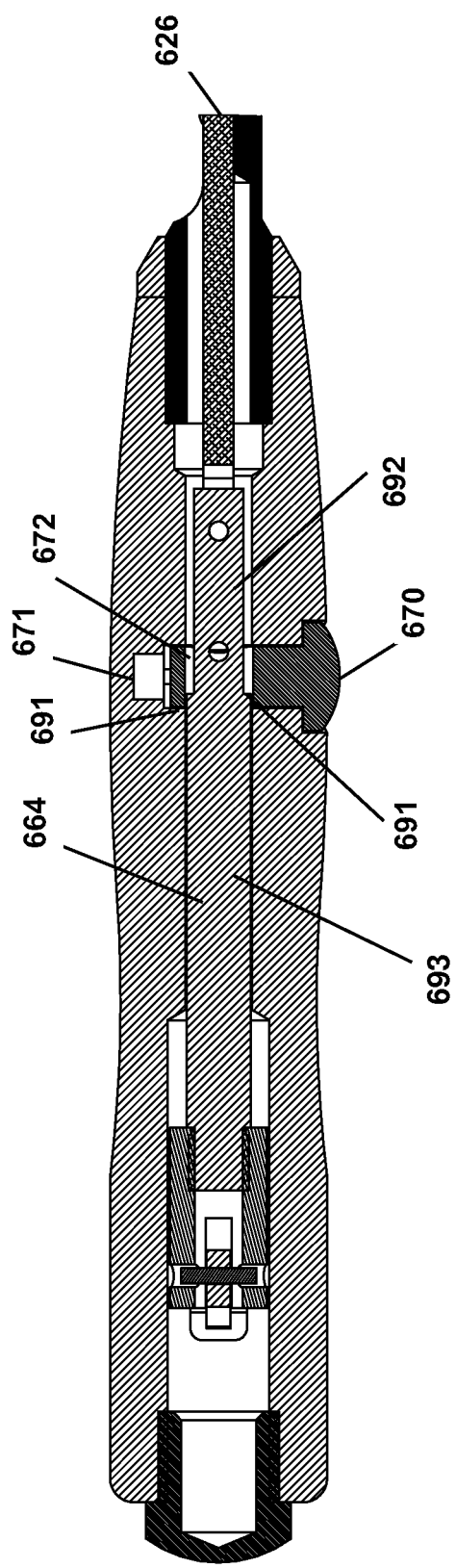
FIG. 61 is a detailed cross-sectional view of the motion limiting mechanism of the instrument shown in FIG. 54.

Forward travel of the central shaft member 626 is selectively limited by abutment between a shoulder portion 691 of the drive shaft 664 and a button 670 through which the drive shaft 664 must pass, as shown in FIG. 61. The button 570 is biased upward by a spring 671 so that the opening 672 through the button 670 is aligned so as to allow passage for a narrower portion 692 of the drive shaft 664 but prevents passage of a wider portion 693 of the central shaft. Pushing downward on the button 670 as in FIG. 61 permits passage of the wider portion 693 of the central shaft, allowing for release of the upper shaft 630 as further discussed below.

Figure 62:
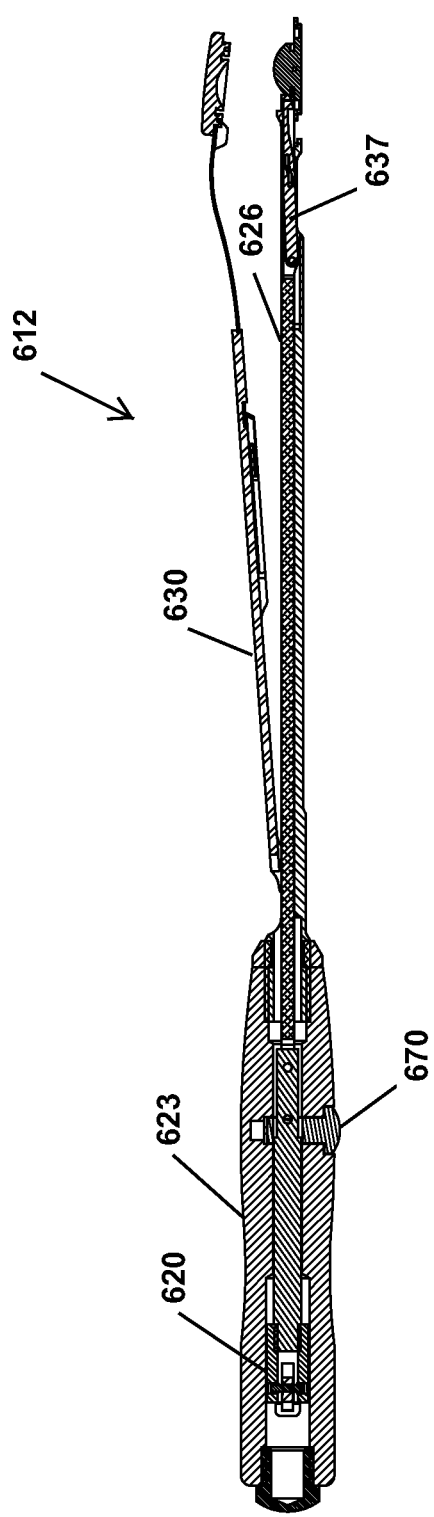
FIG. 62 is a cross-sectional view of the instrument shown in FIG. 54 with the upper shaft member pivoted to an open position.
Figure 63:
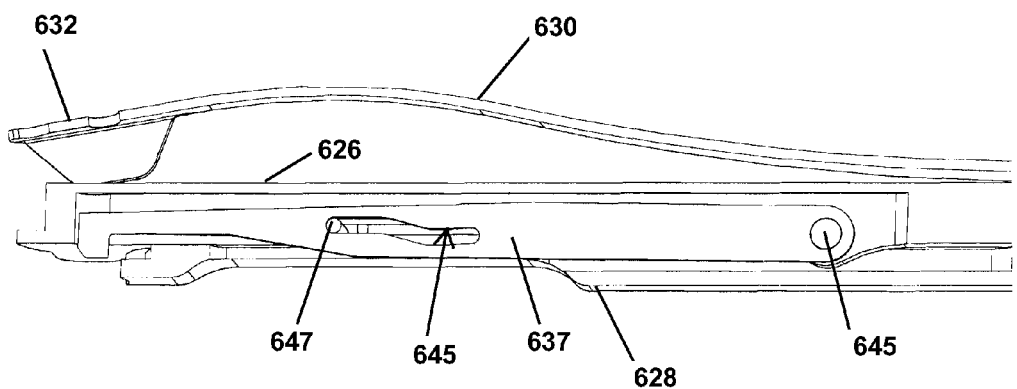
FIG. 63 is a detailed side view of the latch member of the instrument shown in FIG. 54.

FIG. 62 shows additional detail of the shaft assembly 612, including the pivotability of the upper shaft member 630 away from the central shaft 626 and outer shaft 628 when the button 670 is depressed and the central shaft 626 is shifted fully forward. The central shaft 626, outer shaft 628, and upper shaft 630 of the illustrated instrument are configured to secure an implant in a similar manner to that described in connection with FIGS. 38-40, including the pivoting of a latch member 637 as the central shaft member 626 is shifted back and forth. However, the operation of the latch member 637 differs from the operation of the latch members described above. FIG. 63 shows a more detailed view of the latch member 637 that is disposed in the central shaft member 626. The latch member 637 is pivotably mounted to the central shaft member 626 at its rear end by a pivot pin 645. An elongate guide track 645 is formed in the latch, and a pin connected to the lower shaft member 628 is disposed in the guide slot. Shifting of the central shaft member 626 back and forth causes the pin 647 to ride through the contoured guide slot 645, forcing the latch member 637 to pivot upward and downward to secure and release an implant.

Release of the upper shaft member 630 to allow pivoting thereof as shown in FIG. 62 is also controlled by shifting of the central shaft member 626, in a manner substantially similar to that described in connection with FIG. 37. The sides of the upper shaft member 630 are equipped with flexible tabs 681 with inwardly directed flanges that ride in lateral grooves or guide tracks 695 of the central shaft member 626 (see FIG. 55). Ledges or flanges 698 at the top of the guide tracks 695 interact with the tabs 681 of the upper shaft member 630 to prevent the upper shaft member 630 from pivoting away from the rest of the shaft assembly 612 when the central shaft member 626 is in its retracted position. When the central shaft member 626 is shifted forward, the upper shaft member 630 remains relatively stationary until the tabs 681 of the upper shaft member 630 become aligned with an upward opening 697 in the central shaft guide track 695, releasing the upper shaft member 630 from the central shaft member 626 and permitting the upper shaft member 630 to pivot upward. Advantageously, the tabs 681 of the upper shaft member 630 may be sloped inward on their lower surfaces so that the upper shaft member 630 may be re-engaged with the central shaft member 626 through a snap-lock type connection when the central shaft is retracted.

While there have been illustrated and described particular embodiments of the insertion device, it will be appreciated that numerous changes and modifications are possible to those skilled in the art, and it is intended in the appended claims to cover all those changes and modifications which fall within the true spirit and scope of the present device.

What is claimed is:

1. An insertion instrument for inserting an artificial disc device in an intervertebral space, the insertion instrument comprising:
   a handle having a body;
   a first actuator lever operably connected to the handle body;
   a main shaft member operably connected to the handle body having a distal end for securing a portion of the artificial disc device, with the main shaft member configured to be shifted into a receiving and releasing configuration upon pivoting of the first actuator lever and to be shifted to a holding configuration upon release of the first actuator lever;
   a second actuator operably connected to the handle body;
   a brace member shiftable by operation of the second actuator between a bracing configuration that braces the artificial disc device to keep the artificial disc device from moving relative to the brace member and a free configuration that allows the artificial disc device to move relative to the brace member;
   a third actuator operably connected to the handle body; and
   a steering member operated by the third actuator to change the orientation of the artificial disc device only when the brace member is in the free configuration, with the brace member keeping the artificial disc device from moving relative to the steering member when the brace member is in the bracing configuration so that the steering member cannot chance the orientation of the artificial disc device.

2. The instrument of claim 1 wherein the second actuator is resiliently coupled to the brace member so that the brace member applies a preset amount of force to the artificial disc device when in the bracing configuration.

3. The instrument of claim 1 wherein the third actuator is resiliently coupled to the steering member to apply a preset amount of force for steering the artificial disc device.

4. The instrument of claim 1 wherein the second actuator also shifts a locking member that locks the third actuator when the brace member is in the bracing configuration so that the steering member is operated only when the brace member is in the free configuration.

5. The instrument of claim 1 wherein the main shaft member is coupled to a pivotable latch member that engages with the portion of the artificial disc device, the latch member configured to cam against a portion of the brace member to pivot between the receiving and releasing configurations when the main shaft member is shifted relative to the brace member.

6. The instrument of claim 1, wherein the second actuator is coupled to the brace member through a resilient coupling.

7. The instrument of claim 6, wherein the resilient coupling comprises a preloaded spring that applies a set amount of force on the brace member when the brace member is shifted to the bracing configuration.

8. The instrument of claim 6 wherein the resilient coupling comprises a plurality of springs that combine to apply a first amount of force on the brace member when the brace member is in the bracing configuration and to apply a second amount of force on the brace member when the brace member is in the free configuration.

9. The instrument of claim 1, further comprising a locking mechanism for the first actuator, the locking mechanism configured for being shifted from a locked configuration for blocking the first actuator from shifting toward the handle to keep the main shaft member from being shifted between receiving and releasing configurations, to an unlocked configuration for permitting shifting of the first actuator with respect to the handle to allow the main shaft member to be shifted into the receiving and releasing configurations.

10. The instrument of claim 1, wherein the steering member comprises a steering shaft having an engagement portion, the steering shaft being shiftable to cause the engagement portion thereof to contact and shift the disc device to change the orientation of the disc device relative to the distal end of the main shaft member.

11. The instrument of claim 10, wherein the steering shaft extends along a longitudinal axis and is shiftable therealong, and wherein the steering shaft is configured such that shifting the steering shaft towards the distal end of the main shaft member causes the engagement portion of the steering shaft to engage the disc device and cause the disc device to pivot with respect to the instrument.

12. The instrument of claim 10, wherein the handle body comprises a relaseable coupling configured for releasably coupling the steering shaft to the handle body such that the steering shaft may be coupled to and uncoupled from the handle body without use of a separate tool.

13. The instrument of claim 12, wherein the handle body includes a longitudinal axis and has opposite lateral sides spaced laterally from the longitudinal axis and the handle body is configured such that the steering shaft may be mounted to either of the opposite lateral sides for pivoting the disc device in opposite directions respectively relative to the distal end of the main shaft member for allowing the disc device to be inserted into the intervertebral space from a plurality of surgical approaches.

\* \* \* \* \*